US011034961B2

(12) United States Patent
Saragovi et al.

(10) Patent No.: US 11,034,961 B2
(45) Date of Patent: Jun. 15, 2021

(54) TREATMENT USING TRUNCATED TRK B AND TRK C ANTAGONISTS

(71) Applicants: Otonomy, Inc., San Diego, CA (US); Horacio Uri Saragovi, Montreal (CA)

(72) Inventors: Horacio Uri Saragovi, Montreal (CA); Fabrice Piu, San Diego, CA (US)

(73) Assignee: OTONOMY, INC., San Diego, CA (US)

( * ) Notice: Subject to any disclaimer, the term of this patent is extended or adjusted under 35 U.S.C. 154(b) by 21 days.

(21) Appl. No.: 16/041,638

(22) Filed: Jul. 20, 2018

(65) Prior Publication Data
US 2019/0017053 A1    Jan. 17, 2019

Related U.S. Application Data

(63) Continuation of application No. 15/222,710, filed on Jul. 28, 2016, now Pat. No. 10,066,229.

(60) Provisional application No. 62/198,062, filed on Jul. 28, 2015.

(51) Int. Cl.

| | |
|---|---|
| *C12N 15/113* | (2010.01) |
| *A61K 31/7088* | (2006.01) |
| *C12N 15/86* | (2006.01) |
| *A61K 9/00* | (2006.01) |
| *A61P 27/16* | (2006.01) |
| *C12N 7/00* | (2006.01) |
| *A61K 9/06* | (2006.01) |
| *A61K 48/00* | (2006.01) |

(52) U.S. Cl.
CPC ........ *C12N 15/1138* (2013.01); *A61K 9/0046* (2013.01); *A61K 9/06* (2013.01); *A61K 31/7088* (2013.01); *A61K 48/00* (2013.01); *A61P 27/16* (2018.01); *C12N 7/00* (2013.01); *C12N 15/86* (2013.01); *C12N 2310/14* (2013.01); *C12N 2310/531* (2013.01); *C12N 2710/10043* (2013.01); *C12N 2740/15043* (2013.01)

(58) Field of Classification Search
None
See application file for complete search history.

(56) References Cited

U.S. PATENT DOCUMENTS

| | | | |
|---|---|---|---|
| 4,476,116 A | 10/1984 | Anik | |
| 4,683,202 A | 7/1987 | Mullis | |
| 4,843,155 A | 6/1989 | Chomczynski | |
| 5,384,261 A | 1/1995 | Winkler et al. | |
| 5,445,934 A | 8/1995 | Fodor et al. | |
| 5,677,195 A | 10/1997 | Winkler et al. | |
| 5,708,153 A | 1/1998 | Dower et al. | |
| 5,744,305 A | 4/1998 | Fodor et al. | |
| 5,770,358 A | 6/1998 | Dower et al. | |
| 5,770,722 A | 6/1998 | Lockhart et al. | |
| 5,789,162 A | 8/1998 | Dower et al. | |
| 5,800,992 A | 9/1998 | Fodor et al. | |
| 5,854,033 A | 12/1998 | Lizardi | |
| 5,874,219 A | 2/1999 | Rava et al. | |
| 6,020,135 A | 2/2000 | Levine et al. | |
| 6,033,860 A | 3/2000 | Lockhart et al. | |
| 6,040,138 A | 3/2000 | Lockhart et al. | |
| 6,040,193 A | 3/2000 | Winkler et al. | |
| 6,344,316 B1 | 2/2002 | Lockhart et al. | |
| 6,391,452 B1 | 5/2002 | Antonsen et al. | |
| 2004/0110711 A1* | 6/2004 | Krueger | A61K 38/185 514/44 A |
| 2005/0095246 A1* | 5/2005 | Shafer | A61K 38/02 424/145.1 |
| 2006/0148749 A1 | 7/2006 | Krueger et al. | |
| 2006/0148769 A1 | 7/2006 | DeLuca et al. | |
| 2008/0113351 A1* | 5/2008 | Naito | A61K 31/713 435/6.11 |
| 2008/0255096 A1 | 10/2008 | Knipper-Breer et al. | |
| 2012/0004310 A1 | 1/2012 | Longo et al. | |
| 2012/0208706 A1 | 8/2012 | Downing et al. | |
| 2015/0025020 A1* | 1/2015 | Garrigue | A61K 47/02 514/20.5 |
| 2017/0029822 A1 | 2/2017 | Saragovi et al. | |

FOREIGN PATENT DOCUMENTS

| | | |
|---|---|---|
| WO | WO-9803546 A1 | 1/1998 |
| WO | WO-03071872 A1 | 9/2003 |
| WO | WO-2006133353 A2 | 12/2006 |
| WO | WO-2009048605 A1 | 4/2009 |
| WO | WO-2014102426 A1 | 7/2014 |
| WO | WO-2017019905 A1 | 2/2017 |

OTHER PUBLICATIONS

Bai et al. In glaucoma the upregulated truncated TrkC.T1 receptor isoform in Glia causes increased TNF-a production, leading to retinal ganglion cell death. Inv. Ophthalm. & Visual Sci. 51(12): 6639-6651 (2010).
Barany. Genetic disease detection and DNA amplification using cloned thermostable ligase. PNAS USA 88:189-193 (1991).
Brahimi et al. A peptidomimetic of NT-3 acts as a TrkC antagonist. Peptides 30(10):1833-1839 (2009).
Brahimi et al. Combinatorial assembly of small molecules into bivalent antagonists of TrkC or TrkA receptors. PLOS One 9(3):e89617 (2014).
Chothia et al. Canonical structures for the hypervariable regions of immunoglobulins. J Mol Biol. 196(4):901-917 (1987).
Enomoto et al. A multifunctional neurotrophin with reduced affinity to p75NTR enhances transplanted Schwann cell survival and axon growth after spinal cord injury. Exp Neurol 248:170-182 (2013).

(Continued)

*Primary Examiner* — Sean McGarry
(74) *Attorney, Agent, or Firm* — Procopio, Cory, Hargreaves & Savitch LLP

(57) ABSTRACT

Disclosed herein are methods, compositions, vectors, and kits comprising an antagonist of a truncated TrkC or a truncated TrkB. Also described herein are methods of treating and/or preventing an otic disease or condition associated with an elevated expression level of a truncated TrkC or truncated TrkB isoform.

21 Claims, 10 Drawing Sheets

Specification includes a Sequence Listing.

(56) References Cited

OTHER PUBLICATIONS

Esteban et al. A kinase-deficient TrkC receptor isoform activates Arf6-Rac1 signaling through the scaffold protein tamalin. J Cell Biol 173:291-299 (2006).
Guatelli et al. Isothermal, in vitro amplification of nucleic acids by a multienzyme reaction modeled after retroviral replication. PNAS USA 87(5):1874-1878 (1990).
Ibanez et al. An extended surface of binding to Trk tyrosine kinase receptors in NGF and BDNF allows the engineering of a multi-functional pan-neurotrophin. EMBO J 12(6):2281-2293 (1993).
Ibanez et al. Chimeric molecules with multiple neurotrophic activities reveal structural elements determining the specificities of NGF and BDNF. EMBO J 10(8):2105-2110 (1991).
Ilag et al. Pan-neurotrophin 1: a genetically engineered neurotrophic factor displaying multiple specificities in peripheral neurons in vitro and in vivo. PNAS USA 92:607-611 (1995).
Kabat et al. Sequences of Proteins of Immunological Interest. NIH Pub. No. 91-3242. Public Health Service, National Institutes of Health. 1:647-669 (1991).
Kwoh et al. Transcription-based amplification system and detection of amplified human immunodeficiency virus type 1 with a bead-based sandwich hybridization format. PNAS USA 86:1173-1177 (1989).
Liu et al. Bivalent diketopiperazine-based tropomysin receptor kinase C (TrkC) antagonists. J. Med. Chem. 53(13):5044-5048 (2010).
Lizardi et al. Exponential amplification of recombinant-RNA hybridization probes. Nature Biotechnology 6:1197-1202 (1988).
Luberg et al. Human TrkB gene: novel alternative transcripts, protein isoforms and expression pattern in the prefrontal cerebral cortex during postnatal development. J. Neurochem. 113:952-964 (2010).
Maussion et al. Regulation of a truncated form of tropomyosin-related kinase B (TrkB) by Hsa-miR-185* in frontal cortex of suicide completers. PLoS One 7(6):e39301 (2012).
Palm et al. V2-vasopressin receptor antagonists-mechanism of effect and clinical implications in hyponatraemia. Nephrol Dial Transplant 14:2559-2562 (1999).

PCT/US2016/044570 International Preliminary Report on Patentability dated Feb. 8, 2018.
PCT/US2016/044570 International Search Report and Written Opinion dated Dec. 16, 2016.
Ryden et al. Binding of neurotrophin-3 to p75LNGFR, TrkA, and TrkB mediated by a single functional epitope distinct from that recognized by trkC. J Bio Chem 271(10):5623-5627 (1996).
Ryden et al. Functional analysis of mutant neurotrophins deficient in low-affinity binding reveals a role for p75LNGFR in NT-4 signalling. EMBO J 14(9):1979-1990 (1995).
Sanghi et al. Vasopressin antagonism: a future treatment option in heart failure. Eur. Heart J. 26:538-543 (2005).
Singh et al. Encyclopedia of Pharmaceutical Technology. 2nd Ed. pp. 754-757 (2002).
Urfer et al. The binding epitopes of neurotrophin-3 to its receptors trkC and gp75 and the design of a multifunctional human neurotrophin. EMBO J 13(24):5896-5909 (1994).
U.S. Appl. No. 15/222,710 Office Action dated Nov. 16, 2017.
Vidaurre et al. Imbalance of neurotrophin receptor isoforms TrkB-FL/TrkB-T1 induces neuronal death in excitotoxicity. Cell Death and Disease 3:e256 (2012).
Zapata et al. Engineering linear F(ab')2 fragments for efficient production in *Escherichia coli* and enhanced antiproliferative activity. Protein Eng. 8(10):1057-1062 (1995).
Brugeaud et al. Control of Hair Cell Excitability by Vestibular Primary Sensory Neurons. The Journal Of Neuroscience 27(13):3503-3511 (2007).
Khalin et al. Targeted delivery of brain-derived neurotrophic factor for the treatment of blindness and deafness. International Journal Of Nanomedicine 10:3245-3267 (2015).
Meltser et al. Differential activation of mitogen-activated protein kinases and brain-derived neurotrophic factor after temporary or permanent damage to a sensory system. Neuroscience 165(4):1439-1446 (2010).
Schimmang et al. Lack of Bdnf and TrkB signalling in the postnatal cochlea leads to a spatial reshaping of innervation along the tonotopic axis and hearing loss. Development 130(19):4741-4750 (2003).
Wong et al. Mechanisms of sensorineural cell damage, death and survival in the cochlea. Frontiers In Aging Neuroscience 7:58 (2015).

\* cited by examiner

2Ca

2Cg

2Cl

2Ai

2Cb

3Cb 1a (SK-IK)
TrkC and TrkA antagonist 1b (IR-IK)
TrkC and TrkA antagonist 2c (GT-EK)
TrkC antagonist 2d (RI-TG)
TrkC antagonist

2e (SM-GK)
TrkC antagonist

3f (KS-KI)
TrkC antagonist

6dh

TREATMENT USING TRUNCATED TRK B AND TRK C ANTAGONISTS

CROSS-REFERENCE

This application is a continuation of U.S. patent application Ser. No. 15/222,710, filed Jul. 28, 2016, which claims the benefit of U.S. Provisional Application No. 62/198,062, filed Jul. 28, 2015, each of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Jul. 28, 2016, is named 37173-832-301_SL.txt and is 97,626 bytes in size.

BACKGROUND OF THE INVENTION

Neuron loss such as sensory neuron loss is the cause of morbidity in many otic related neurodegenerative diseases. In some instances, sensory neurons express Trk family of receptors such as TrkB and/or TrkC. Activity of the Trk family of receptors correlates with sensory neuron survival or death, maintenance of synapses and phenotype, and function.

SUMMARY OF THE INVENTION

Disclosed herein, in certain embodiments, is a method of treating an otic disease or condition or a symptomatic or pre-symptomatic condition with alterations of otic synapses, comprising administering to a patient in need thereof a therapeutic amount of a pharmaceutical composition comprising: (a) an antagonist of truncated TrkC or truncated TrkB, wherein the antagonist induces a decrease in the truncated TrkC or truncated TrkB expression level or activity or impedes the truncated TrkC or truncated TrkB interaction with a truncated TrkC or truncated TrkB binding partner; and (b) a pharmaceutically acceptable excipient and/or a delivery vehicle. Also disclosed herein is a method of preventing an otic disease or condition or reducing the progression of an otic disease or condition, comprising administering to a patient in need thereof a therapeutic amount of a pharmaceutical composition comprising: (a) an antagonist of truncated TrkC or truncated TrkB, wherein the antagonist induces a decrease in the truncated TrkC or truncated TrkB expression level or activity or impedes the truncated TrkC or truncated TrkB interaction with a truncated TrkC or truncated TrkB binding partner; and (b) a pharmaceutically acceptable excipient and/or a delivery vehicle. In some embodiments, the otic disease or condition comprises a disease or condition associated with hearing loss. In some embodiments, the otic disease or condition comprises ototoxicity, chemotherapy induced hearing loss, excitotoxicity, sensorineural hearing loss, noise induced hearing loss, presbycusis, Meniere's Disease/Syndrome, endolymphatic hydrops, labyrinthitis, Ramsay Hunt's Syndrome, vestibular neuronitis, tinnitus, or microvascular compression syndrome. In some embodiments, the antagonist that induces a decrease in the truncated TrkC or truncated TrkB expression level or activity is a nucleic acid polymer, a polypeptide, or a small molecule. In some embodiments, the antagonist that induces a decrease in the truncated TrkC or truncated TrkB expression level or activity is a nucleic acid polymer. In some embodiments, the nucleic acid polymer hybridizes to a target sequence of the truncated TrkC or truncated TrkB mRNA. In some embodiments, the nucleic acid polymer hybridizes to a target sequence that is located at the 3'UTR region of the truncated TrkC or truncated TrkB mRNA. In some embodiments, the nucleic acid polymer hybridizes to a target sequence comprising a binding motif selected from CCAAUC, CUCCAA, or ACUGUG. In some embodiments, the nucleic acid polymer comprises a short hairpin RNA (shRNA) molecule, a microRNA (miRNA) molecule, a siRNA molecule, or a double stranded RNA molecule. In some embodiments, the nucleic acid polymer is a shRNA molecule. In some embodiments, the nucleic acid polymer comprises at least 80%, 85%, 90%, 95%, or 99% sequence identity to a nucleic acid sequence selected from SEQ ID NOs: 1-5 and 114-119. In some embodiments, the nucleic acid polymer comprises 100% sequence identity to a nucleic acid sequence selected from SEQ ID NOs: 1-5 and 114-119. In some embodiments, the nucleic acid polymer consists of a nucleic acid sequence selected from SEQ ID NOs: 1-5 and 114-119. In some embodiments, the nucleic acid polymer comprising at least 80%, 85%, 90%, 95%, or 99% sequence identity to a nucleic acid sequence selected from SEQ ID NOs: 1-5 hybridizes to a target sequence of the truncated TrkC. In some embodiments, the nucleic acid polymer comprising 100% sequence identity to a nucleic acid sequence selected from SEQ ID NOs: 1-5 hybridizes to a target sequence of the truncated TrkC. In some embodiments, the nucleic acid polymer consisting of a nucleic acid sequence selected from SEQ ID NOs: 1-5 hybridizes to a target sequence of the truncated TrkC. In some embodiments, the nucleic acid polymer comprising at least 80%, 85%, 90%, 95%, or 99% sequence identity to a nucleic acid sequence that hybridizes to a target sequence of the truncated TrkB. In some embodiments, the nucleic acid polymer comprising 100% sequence identity to a nucleic acid sequence that hybridizes to a target sequence of the truncated TrkB. In some embodiments, the nucleic acid polymer comprising at least 80%, 85%, 90%, 95%, or 99% sequence identity to a nucleic acid sequence selected from SEQ ID NOs: 114-119 hybridizes to a target sequence of the truncated TrkB. In some embodiments, the nucleic acid polymer comprising 100% sequence identity to a nucleic acid sequence selected from SEQ ID NOs: 114-119 hybridizes to a target sequence of the truncated TrkB. In some embodiments, the nucleic acid polymer consisting of a nucleic acid sequence selected from SEQ ID NOs: 114-119 hybridizes to a target sequence of the truncated TrkB. In some embodiments, the nucleic acid polymer is further modified at the nucleoside moiety, at the phosphate moiety, or a combination thereof. In some embodiments, the nucleic acid polymer further comprises one or more artificial nucleotide bases. In some embodiments, the one or more artificial nucleotide bases comprises 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O—N-methylacetamido (2'-O-NMA) modified, locked nucleic acid (LNA), ethylene nucleic acid (ENA), peptide nucleic acid (PNA), 1', 5'-anhydrohexitol nucleic acids (HNA), morpholino, methylphosphonate nucleotides, thiolphosphonate nucleotides, or 2'-fluoro N3-P5'-phosphoramidites. In some embodiments, the nucleic acid polymer is at most 10, 15, 20, 25, 30, 35, 40, 45, 50, 55, 60, 70, 80, 90, or 100 nucleotides in length. In some embodiments, the pharmaceutical composition comprising the nucleic acid polymer is administered to a patient in need thereof as an intramuscular, intratympanic, intracochlear, intravenous or subcutaneous administration. In some embodiments, the method further comprises a vector comprising the nucleic acid polymer. In some embodiments, the vector is a viral vector. In some embodiments, the viral vector is a lentiviral vector, a retroviral vector, an adenoviral vector, an adeno-associated viral vector, an alphaviral vector, a herpes simplex virus vector, a vaccinia viral vector, or a chimeric viral vector. In some embodiments, the antagonist that impedes the truncated TrkC or truncated TrkB interaction with a truncated TrkC or truncated TrkB binding partner is a small molecule or a polypeptide. In some embodiments, the antagonist that impedes the truncated TrkC or truncated TrkB interaction with a truncated TrkC or truncated TrkB binding partner is a small molecule. In some embodiments, the small molecule is a peptidomimetic. In some embodiments, the small molecule is a small molecule as illustrated in FIG. 2. In some embodiments, the antagonist that impedes the truncated TrkC or truncated TrkB interaction with a truncated TrkC or truncated TrkB binding partner is a polypeptide. In some embodiments, the polypeptide is an antibody or binding fragment thereof. In some embodiments, the antibody or binding fragment thereof comprises a humanized antibody or binding fragment thereof, chimeric antibody or binding fragment thereof, monoclonal antibody or binding fragment thereof, monovalent Fab', divalent Fab2, single-chain variable fragment (scFv), diabody, minibody, single-domain antibody (sdAb), or camelid antibody or binding fragment thereof. In some embodiments, the truncated TrkC is a non-catalytic truncated TrkC. In some embodiments, the truncated TrkC protein comprises at least 80%, 85%, 90%, 95%, or 99% sequence identity to the amino acid sequence of SEQ ID NO: 10 or 113. In some embodiments, the truncated TrkC protein consists of the amino acid sequence of SEQ ID NO: 10 or 113. In some embodiments, the truncated TrkC is TrkC.T1. In some embodiments, the truncated TrkB is a non-catalytic truncated TrkB. In some embodiments, the truncated TrkB protein comprises at least 80%, 85%, 90%, 95%, or 99% sequence identity to an amino acid sequence selected from SEQ ID NOs: 11-12 and 121-123. In some embodiments, the truncated TrkB protein consists of an amino acid sequence selected from SEQ ID NOs: 11-12 and 121-123. In some embodiments, the truncated TrkB is TrkB.T1. In some embodiments, the truncated TrkC binding partner comprises a neurotrophin or a microRNA molecule. In some embodiments, the neurotrophin is neurotrophin-3 (NT-3). In some embodiments, the microRNA molecule comprises miR-128, miR-509, or miR-768-5p. In some embodiments, the truncated TrkB binding partner comprises a neurotrophin. In some embodiments, the neurotrophin is brain derived neurotrophic factor (BDNF), neurotrophin-3 (NT-3), or neurotrophin-4 (NT-4). In some embodiments, the pharmaceutical composition is administered for intramuscular, intratympanic, intracochlear, intravenous or subcutaneous administration.

Disclosed herein, in certain embodiments, is a method of treating an otic disease or condition, comprising administering to a patient in need thereof a therapeutic amount of a pharmaceutical composition comprising: (a) a nucleic acid polymer that hybridizes to a target sequence of truncated TrkC or truncated TrkB, wherein the nucleic acid polymer is capable of decreasing the expression level of the truncated TrkC or truncated TrkB; and (b) a pharmaceutically acceptable excipient and/or a delivery vehicle. Also disclosed herein, in certain embodiments, is a method of preventing an otic disease or condition or reducing the progression of an otic disease or condition, comprising administering to a patient in need thereof a therapeutic amount of a pharmaceutical composition comprising: (a) a nucleic acid polymer that hybridizes to a target sequence of truncated TrkC or truncated TrkB, wherein the nucleic acid polymer is capable of decreasing the expression level of the truncated TrkC or truncated TrkB; and (b) a pharmaceutically acceptable excipient and/or a delivery vehicle. In some embodiments, the otic disease or condition comprises a disease or condition associated with hearing loss. In some embodiments, the otic disease or condition comprises ototoxicity, chemotherapy induced hearing loss, excitotoxicity, sensorineural hearing loss, noise induced hearing loss, presbycusis, Meniere's Disease/Syndrome, endolymphatic hydrops, labyrinthitis, Ramsay Hunt's Syndrome, vestibular neuronitis, tinnitus, or microvascular compression syndrome. In some embodiments, the target sequence is located at the 3'UTR region of the truncated TrkC or truncated TrkB mRNA. In some embodiments, the nucleic acid polymer hybridizes to a target sequence comprising a binding motif selected from CCAAUC, CUCCAA, or ACUGUG. In some embodiments, the nucleic acid polymer comprises a short hairpin RNA (shRNA) molecule, a microRNA (miRNA) molecule, a siRNA molecule, or a double stranded RNA molecule. In some embodiments, the nucleic acid polymer is a shRNA molecule. In some embodiments, the nucleic acid polymer comprises at least 80%, 85%, 90%, 95%, or 99% sequence identity to a nucleic acid sequence selected from SEQ ID NOs: 1-5 and 114-119. In some embodiments, the nucleic acid polymer comprises 100% sequence identity to a nucleic acid sequence selected from SEQ ID NOs: 1-5 and 114-119. In some embodiments, the nucleic acid polymer consists of a nucleic acid sequence selected from SEQ ID NOs: 1-5 and 114-119. In some embodiments, the nucleic acid polymer comprising at least 80%, 85%, 90%, 95%, or 99% sequence identity to a nucleic acid sequence selected from SEQ ID NOs: 1-5 hybridizes to a target sequence of the truncated TrkC. In some embodiments, the nucleic acid polymer comprising 100% sequence identity to a nucleic acid sequence selected from SEQ ID NOs: 1-5 hybridizes to a target sequence of the truncated TrkC. In some embodiments, the nucleic acid polymer consisting of a nucleic acid sequence selected from SEQ ID NOs: 1-5 hybridizes to a target sequence of the truncated TrkC. In some embodiments, the nucleic acid polymer comprising at least 80%, 85%, 90%, 95%, or 99% sequence identity to a nucleic acid sequence that hybridizes to a target sequence of the truncated TrkB. In some embodiments, the nucleic acid polymer comprising 100% sequence identity to a nucleic acid sequence that hybridizes to a target sequence of the truncated TrkB. In some embodiments, the nucleic acid polymer comprising at least 80%, 85%, 90%, 95%, or 99% sequence identity to a nucleic acid sequence selected from SEQ ID NOs: 114-119 hybridizes to a target sequence of the truncated TrkB. In some embodiments, the nucleic acid polymer comprising 100% sequence identity to a nucleic acid sequence selected from SEQ ID NOs: 114-119 hybridizes to a target sequence of the truncated TrkB. In some embodiments, the nucleic acid polymer consisting of a nucleic acid sequence selected from SEQ ID NOs: 114-119 hybridizes to a target sequence of the truncated TrkB. In some embodiments, the nucleic acid polymer is further modified at the nucleoside moiety, at the phosphate moiety, or a combination thereof. In some embodiments, the nucleic acid polymer is administered to a patient in need thereof as an intramuscular, intratympanic, intracochlear, intravenous or subcutaneous administration.

Disclosed herein, in certain embodiments, is a method of treating an otic disease or condition, comprising administering to a patient in need thereof a therapeutic amount of a pharmaceutical composition comprising: (a) a vector comprising a nucleic acid polymer wherein the nucleic acid polymer comprises at least 80% sequence identity to a nucleic acid sequence selected from SEQ ID NOs: 1-5 and 114-119; and (b) a pharmaceutically acceptable excipient and/or a delivery vehicle. Also disclosed herein, in certain embodiments, is a method of preventing an otic disease or condition or reducing the progression of an otic disease or condition, comprising administering to a patient in need thereof a therapeutic amount of a pharmaceutical composition comprising: (a) a vector comprising a nucleic acid polymer wherein the nucleic acid polymer comprises at least 80% sequence identity to a nucleic acid sequence selected from SEQ ID NOs: 1-5 and 114-119; and (b) a pharmaceutically acceptable excipient and/or a delivery vehicle. In some embodiments, the vector comprising a nucleic acid polymer wherein the nucleic acid polymer comprises at least 85%, 90%, 95%, or 99% sequence identity to a nucleic acid sequence selected from SEQ ID NOs: 1-5 and 114-119. In some embodiments, the vector comprises a nucleic acid polymer wherein the nucleic acid polymer consists of a nucleic acid sequence selected from SEQ ID NOs: 1-5 and 114-119. In some embodiments, the vector is a viral vector. In some embodiments, the viral vector is a lentiviral vector, a retroviral vector, an adenoviral vector, an adeno-associated viral vector, an alphaviral vector, a herpes simplex virus vector, a vaccinia viral vector, or a chimeric viral vector. In some embodiments, the vector is delivered through a viral delivery method. In some embodiments, the vector is delivered through electroporation, chemical method, microinjection, gene gun, impalefection, hydrodynamics-based delivery, continuous infusion, or sonication. In some embodiments, the chemical method is lipofection. In some embodiments, the vector is administered to a patient in need thereof as an intramuscular, intratympanic, intracochlear, intravenous or subcutaneous administration.

Disclosed herein, in certain embodiments, is a method of treating an otic disease or condition, comprising administering to a patient in need thereof a therapeutic amount of a pharmaceutical composition comprising: (a) a small molecule antagonist of a truncated TrkC or truncated TrkB; and (b) a pharmaceutically acceptable excipient and/or a delivery vehicle. Also disclosed herein, in certain embodiments, is a method of preventing an otic disease or condition or reducing the progression of an otic disease or condition, comprising administering to a patient in need thereof a therapeutic amount of a pharmaceutical composition comprising: (a) a small molecule antagonist of a truncated TrkC or truncated TrkB; and (b) a pharmaceutically acceptable excipient and/or a delivery vehicle. In some embodiments, the small molecule antagonist impedes the truncated TrkC or truncated TrkB interaction with a truncated TrkC or truncated TrkB binding partner. In some embodiments, the small molecule is a peptidomimetic. In some embodiments, the small molecule is a small molecule as illustrated in FIG. 2. In some embodiments, the truncated TrkC is a non-catalytic truncated TrkC. In some embodiments, the truncated TrkC is TrkC.T1. In some embodiments, the truncated TrkB is a non-catalytic truncated TrkB. In some embodiments, the truncated TrkB is TrkB.T1.

Disclosed herein, in certain embodiments, is a method of stratifying an individual having an otic disease or condition for treatment with a pharmaceutical composition, comprising: (a) determining the expression level of a truncated TrkC or truncated TrkB; and (b) administering to the individual a therapeutically effective amount of the pharmaceutical composition, wherein the pharmaceutical composition comprises an antagonist of truncated TrkC or truncated TrkB, wherein the antagonist induces a decrease in the truncated TrkC or truncated TrkB expression level or impedes the truncated TrkC or truncated TrkB interaction with a truncated TrkC or truncated TrkB binding partner; and a pharmaceutically acceptable excipient and/or a delivery vehicle; if there is an elevated expression level of the truncated TrkC or truncated TrkB. Also disclosed herein is a method of optimizing the therapy of an individual receiving a pharmaceutical composition for treatment of an otic disease or condition, comprising: (a) determining the expression level of a truncated TrkC or truncated TrkB; and (b) modifying, discontinuing, or continuing the treatment with the pharmaceutical composition based on the expression level of the truncated TrkC or truncated TrkB, wherein the pharmaceutical composition comprises an antagonist of truncated TrkC or truncated TrkB, wherein the antagonist induces a decrease in the truncated TrkC or truncated TrkB expression level or impedes the truncated TrkC or truncated TrkB interaction with a truncated TrkC or truncated TrkB binding partner; and a pharmaceutically acceptable excipient and/or a delivery vehicle. In some embodiments, the method further comprises testing a sample containing nucleic acid molecules encoding the truncated TrkC or truncated TrkB obtained from the individual. In some embodiments, the nucleic acid molecule is RNA. In some embodiments, the nucleic acid molecule is DNA. In some embodiments, the DNA is genomic DNA. In some embodiments, testing comprises amplifying the nucleic acid molecules encoding the truncated TrkC or truncated TrkB gene. In some embodiments, amplification is by isothermal amplification or polymerase chain reaction (PCR). In some embodiments, amplification is by PCR. In some embodiments, the sample is a cell sample or a tissue sample. In some embodiments, the otic disease or condition comprises a disease or condition associated with hearing loss. In some embodiments, the otic disease or condition comprises ototoxicity, chemotherapy induced hearing loss, excitotoxicity, sensorineural hearing loss, noise induced hearing loss, presbycusis, Meniere's Disease/Syndrome, endolymphatic hydrops, labyrinthitis, Ramsay Hunt's Syndrome, vestibular neuronitis, tinnitus, or microvascular compression syndrome.

Disclosed herein, in certain embodiments, is a method of stratifying an individual having an otic disease or condition for treatment with a pharmaceutical composition, comprising: (a) determining the expression level of a truncated TrkC or truncated TrkB; and (b) administering to the individual a therapeutically effective amount of the pharmaceutical composition, wherein the pharmaceutical composition comprises a nucleic acid polymer that hybridizes to a target sequence of truncated TrkC or truncated TrkB, wherein the nucleic acid polymer is capable of decreasing the expression level of the truncated TrkC or truncated TrkB; and a pharmaceutically acceptable excipient and/or a delivery vehicle; if there is an elevated expression level of the truncated TrkC or truncated TrkB. Also disclosed herein is a method of optimizing the therapy of an individual receiving a pharmaceutical composition for treatment of an otic disease or condition, comprising: (a) determining the expression level of a truncated TrkC or truncated TrkB; and (b) modifying, discontinuing, or continuing the treatment with the pharmaceutical composition based on the expression level of the truncated TrkC or truncated TrkB, wherein the pharmaceutical composition comprises a nucleic acid polymer that hybridizes to a target sequence of truncated TrkC or truncated TrkB, wherein the nucleic acid polymer is capable of decreasing the expression level of the truncated TrkC or truncated TrkB; and a pharmaceutically acceptable excipient and/or a delivery vehicle. Additional described herein is a method of stratifying an individual having an otic disease or condition for treatment with a pharmaceutical composition, comprising: (a) determining the expression level of a truncated TrkC or truncated TrkB; and (b) administering to the individual a therapeutically effective amount of the pharmaceutical composition, wherein the pharmaceutical composition comprises a small molecule antagonist of a truncated TrkC or truncated TrkB; and a pharmaceutically acceptable excipient and/or a delivery vehicle; if there is an elevated expression level of the truncated TrkC or truncated TrkB. Further disclosed herein is a method of optimizing the therapy of an individual receiving a pharmaceutical composition for treatment of an otic disease or condition, comprising: (a) determining the expression level of a truncated TrkC or truncated TrkB; and (b) modifying, discontinuing, or continuing the treatment with the pharmaceutical composition based on the expression level of the truncated TrkC or truncated TrkB, wherein the pharmaceutical composition comprises a small molecule antagonist of a truncated TrkC or truncated TrkB; and a pharmaceutically acceptable excipient and/or a delivery vehicle. In some embodiments, the otic disease or condition comprises a disease or condition associated with hearing loss. In some embodiments, the otic disease or condition comprises ototoxicity, chemotherapy induced hearing loss, excitotoxicity, sensorineural hearing loss, noise induced hearing loss, presbycusis, Meniere's Disease/Syndrome, endolymphatic hydrops, labyrinthitis, Ramsay Hunt's Syndrome, vestibular neuronitis, tinnitus, or microvascular compression syndrome.

Disclosed herein, in certain embodiments, is a method of stratifying an individual having an otic disease or condition for treatment with a pharmaceutical composition, comprising (a) determining the expression level of a truncated TrkC or truncated TrkB; and (b) administering to the individual a therapeutically effective amount of the pharmaceutical composition, wherein the pharmaceutical composition comprises (i) a nucleic acid polymer that hybridizes to a target sequence of truncated TrkC or truncated TrkB, wherein the nucleic acid polymer is capable of decreasing the expression level of the truncated TrkC or truncated TrkB; and (ii) a pharmaceutically acceptable excipient and/or a delivery vehicle; if there is an elevated expression level of the truncated TrkC or truncated TrkB.

Disclosed herein, in certain embodiments, is a method of optimizing the therapy of an individual receiving a pharmaceutical composition for treatment of an otic disease or condition, comprising (a) determining the expression level of a truncated TrkC or truncated TrkB; and (b) modifying, discontinuing, or continuing the treatment with the pharmaceutical composition based on the expression level of the truncated TrkC or truncated TrkB, wherein the pharmaceutical composition comprises (ii) a nucleic acid polymer that hybridizes to a target sequence of truncated TrkC or truncated TrkB, wherein the nucleic acid polymer is capable of decreasing the expression level of the truncated TrkC or truncated TrkB; and (ii) a pharmaceutically acceptable excipient and/or a delivery vehicle.

Disclosed herein, in certain embodiments, is an isolated and purified nucleic acid polymer comprising at least 80%, 85%, 90%, 95%, 99% or 100% sequence identity to a nucleic acid sequence selected from SEQ ID NOs: 1-5 and 114-119. In some embodiments, the isolated and purified nucleic acid polymer is further modified at the nucleoside moiety, at the phosphate moiety, or a combination thereof.

Disclosed herein, in certain embodiments, is a pharmaceutical composition comprising an isolated and purified nucleic acid polymer comprising at least 80%, 85%, 90%, 95%, 99% or 100% sequence identity to a nucleic acid sequence selected from SEQ ID NOs: 1-5 and 114-119; and a pharmaceutically acceptable excipient and/or a delivery vehicle. In some embodiments, the pharmaceutical composition further comprises a poloxamer. In some embodiments, the pharmaceutical composition has between about 14% to about 21% by weight of the poloxamer. In some embodiments, the pharmaceutical composition has between about 15% to about 17% by weight of the poloxamer. In some embodiments, the poloxamer is poloxamer 407.

BRIEF DESCRIPTION OF THE DRAWINGS

Various aspects of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A is adapted from Esteban et al. *J Cell Biol* 2006; 173:291-299. FIG. 1B is adapted from Luberg et al. J. Neurochem. 2010; 113:952-964.

DETAILED DESCRIPTION OF THE INVENTION

Figure 1A:
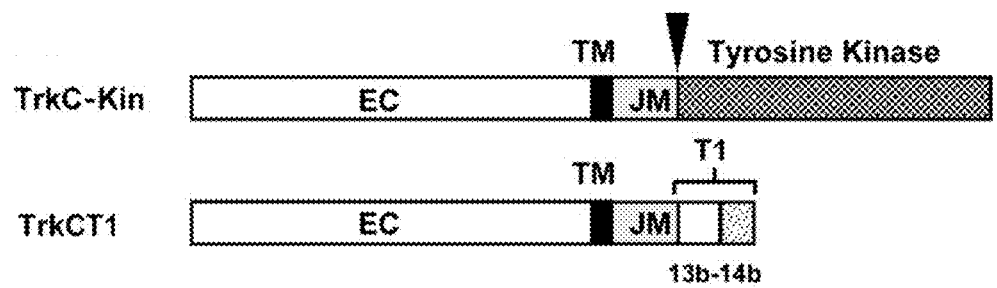
FIG. 1A and FIG. 1B illustrate the full length TrkC and TrkB and their respective isoforms.

Neurotrophins are dimeric polypeptide growth factors that regulate the peripheral and central nervous systems and other tissues and promote functions such as neuronal survival and regulation of synaptic plasticity. In some instances, the family of neurotrophins includes nerve growth factor (NGF), brain-derived neurotrophic factor (BDNF), neurotrophin-3 (NT-3), and neurotrophin-4 (NT-4). In some instances, neurotrophins mediate their effects through interaction with either the Trk family of receptors or with the p75 neurotrophin receptor which belongs to the tumor necrosis factor receptor superfamily. In some cases, interaction with the Trk family of receptors activates several signaling cascades, such as the phosphatidylinositol-3-kinase, phospholipase C, SN T, and Ras/mitogen-activated protein kinase pathways, which mediate growth and survival responses of the neurotrophins.

The Trk family of receptors comprises three homologs, TrkA (NTRK1), TrkB (NTRK2), and TrkC (NTRK3). Tropomyosin receptor kinase C (TrkC), also known as NT-3 growth factor receptor, neurotrophic tyrosine kinase receptor type 3, or TrkC tyrosine kinase, is the receptor for neurotrophin-3 (NT-3). Tropomyosin receptor kinase B (TrkB), also known as Tyrosine receptor kinase B, BDNF/NT-3 growth factors receptor, or neurotrophic tyrosine kinase receptor type 2, is the receptor for BDNF, NT-4, and in some instances, to NT-3 but at a reduced affinity.

In some embodiments, TrkC and TrkB comprise both full-length and truncated isoforms. In some instances, the truncated isoforms of TrkC and TrkB serve as dominant-negative regulators of their full-length counterparts. In some embodiments, the full-length TrkC and full-length TrkB are associated with neuroprotection. However in some cases, truncated TrkC and TrkB isoforms are associated with neurodegeneration. As such in some embodiments, elevated expression levels or activity of truncated TrkC or truncated TrkB are associated with an otic disease or condition.

Described herein, in certain embodiments, are methods, pharmaceutical compositions, vectors, and kits comprising an antagonist of a truncated TrkC or a truncated TrkB. In some embodiments, described herein is a method of treating an otic disease or condition comprising administering to a patient in need thereof a therapeutic amount of a pharmaceutical composition comprising an antagonist of truncated TrkC or truncated TrkB, wherein the antagonist induces a decrease in the truncated TrkC or truncated TrkB expression level or activity or impedes the truncated TrkC or truncated TrkB interaction with a truncated TrkC or truncated TrkB binding partner. In some embodiments, also described herein include a method of preventing an otic disease or condition or reducing the progression of an otic disease or condition comprising administering to a patient in need thereof a therapeutic amount of a pharmaceutical composition comprising an antagonist of truncated TrkC or truncated TrkB, wherein the antagonist induces a decrease in the truncated TrkC or truncated TrkB expression level or activity or impedes the truncated TrkC or truncated TrkB interaction with a truncated TrkC or truncated TrkB binding partner.

Truncated TrkC and Truncated TrkB Isoforms

In some embodiments, TrkC comprises about 20 exons. In some instances, a truncated TrkC isoform lacks one or more of the 20 exons or comprises one or more altered exons. In some embodiments, a truncated TrkC is a non-catalytic truncated TrkC. In some embodiments, a truncated TrkC protein comprises at least 80%, 85%, 90%, 95%, or 99% sequence identity to the amino acid sequence of SEQ ID NO: 10 or 113. In some instances, a truncated TrkC protein consists of the amino acid sequence of SEQ ID NO: 10 or 113. In some cases, a truncated TrkC is TrkC.T1. In some instances, a truncated TrkC is a truncated TrkC as illustrated in FIG. 1A. In some instances, a full-length TrkC is a TrkC comprising at least 80%, 85%, 90%, 95%, 99% or 100% sequence identity to the amino acid sequence of SEQ ID NOs: 9 and 110-112.

Figure 1B:
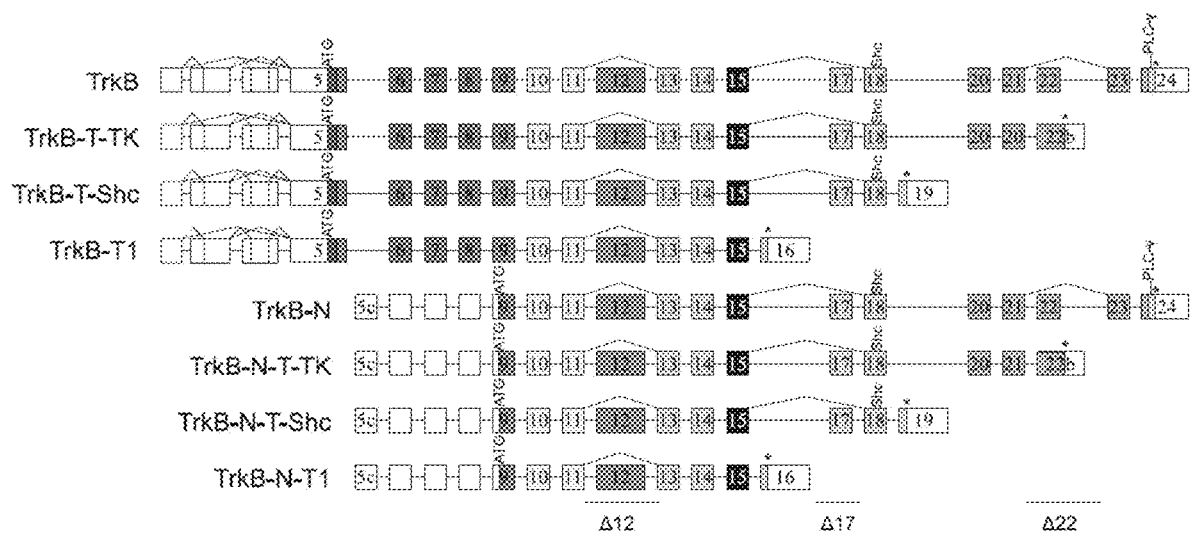

In some instances, TrkB comprises about 24 exons. In some instances, a truncated TrkB isoform lacks one or more of the 24 exons or comprises one or more altered exons. In some instances, truncated TrkB comprises TrkB-T-TK, TrkB-T Shc, TrkB.T1 (or TrkB-T1), TrkB.T2 (or TrkB-T2), TrkB-N, TrkB-N-T-TK, TrkB-N-T-Shc, or TrkB-N-T1. In some embodiments, truncated TrkB is a truncated TrkB as illustrated in FIG. 1B.

In some embodiments, the truncated TrkB is a non-catalytic truncated TrkB. In some instances, a truncated TrkB protein comprises at least 80%, 85%, 90%, 95%, or 99% sequence identity to an amino acid sequence selected from SEQ ID NOs: 11-12 and 121-123. In some cases, a truncated TrkB protein consists of an amino acid sequence selected from SEQ ID NOs: 11-12 and 121-123. In some cases, a truncated TrkB is TrkB.T1 (or TrkB-T1). In some cases, a full-length TrkB is a TrkB comprising at least 80%, 85%, 90%, 95%, 99% or 100% sequence identity to the amino acid sequence of SEQ ID NO: 120.

Nucleic Acid Polymer Antagonists

Disclosed herein, in certain embodiments, is a method of treating an otic disease or condition, preventing an otic disease or condition or reducing the progression of an otic disease or condition comprising administering to a patient in need thereof a therapeutic amount of a pharmaceutical composition which comprises a nucleic acid polymer. In some embodiments, the pharmaceutical composition comprises a nucleic acid polymer that comprises at least 80% sequence identity to a nucleic acid sequence selected from SEQ ID NOs: 1-5 and 114-119, and wherein the nucleic acid polymer is at most 100 nucleotides in length; and a pharmaceutically acceptable excipient and/or a delivery vehicle. In some instances, the nucleic acid polymer comprises at least 81%, 82%, 83%, 84%, 85%, 86%, 87%, 88%, 89%, 90%, 91%, 92%, 93%, 94%, 95%, 96%, 97%, 98%, or 99% sequence identity to a nucleic acid sequence selected from SEQ ID NOs: 1-5 and 114-119. In some instances, the nucleic acid polymer comprises 100% sequence identity to a nucleic acid sequence selected from SEQ ID NOs: 1-5 and 114-119. In some instances, the nucleic acid polymer consists of a nucleic acid sequence selected from SEQ ID NOs: 1-5 and 114-119.

In some cases, the nucleic acid polymer hybridizes to a target sequence of the truncated TrkC or truncated TrkB mRNA. In some cases, the nucleic acid polymer induces a decrease in a truncated TrkC or truncated TrkB expression level. In some cases, the nucleic acid polymer comprising at least 81%, 82%, 83%, 84%, 85%, 86%, 87%, 88%, 89%, 90%, 91%, 92%, 93%, 94%, 95%, 96%, 97%, 98%, or 99% sequence identity to a nucleic acid sequence selected from SEQ ID NOs: 1-5 hybridizes to a target sequence of the truncated TrkC. In some cases, the nucleic acid polymer comprising at least 81% sequence identity to a nucleic acid sequence selected from SEQ ID NOs: 1-5 hybridizes to a target sequence of the truncated TrkC. In some cases, the nucleic acid polymer comprising at least 82% sequence identity to a nucleic acid sequence selected from SEQ ID NOs: 1-5 hybridizes to a target sequence of the truncated TrkC. In some cases, the nucleic acid polymer comprising at least 83% sequence identity to a nucleic acid sequence selected from SEQ ID NOs: 1-5 hybridizes to a target sequence of the truncated TrkC. In some cases, the nucleic acid polymer comprising at least 84% sequence identity to a nucleic acid sequence selected from SEQ ID NOs: 1-5 hybridizes to a target sequence of the truncated TrkC. In some cases, the nucleic acid polymer comprising at least 85% sequence identity to a nucleic acid sequence selected from SEQ ID NOs: 1-5 hybridizes to a target sequence of the truncated TrkC. In some cases, the nucleic acid polymer comprising at least 86% sequence identity to a nucleic acid sequence selected from SEQ ID NOs: 1-5 hybridizes to a target sequence of the truncated TrkC. In some cases, the nucleic acid polymer comprising at least 87% sequence identity to a nucleic acid sequence selected from SEQ ID NOs: 1-5 hybridizes to a target sequence of the truncated TrkC. In some cases, the nucleic acid polymer comprising at least 88% sequence identity to a nucleic acid sequence selected from SEQ ID NOs: 1-5 hybridizes to a target sequence of the truncated TrkC. In some cases, the nucleic acid polymer comprising at least 89% sequence identity to a nucleic acid sequence selected from SEQ ID NOs: 1-5 hybridizes to a target sequence of the truncated TrkC. In some cases, the nucleic acid polymer comprising at least 90% sequence identity to a nucleic acid sequence selected from SEQ ID NOs: 1-5 hybridizes to a target sequence of the truncated TrkC. In some cases, the nucleic acid polymer comprising at least 91% sequence identity to a nucleic acid sequence selected from SEQ ID NOs: 1-5 hybridizes to a target sequence of the truncated TrkC. In some cases, the nucleic acid polymer comprising at least 92% sequence identity to a nucleic acid sequence selected from SEQ ID NOs: 1-5 hybridizes to a target sequence of the truncated TrkC. In some cases, the nucleic acid polymer comprising at least 93% sequence identity to a nucleic acid sequence selected from SEQ ID NOs: 1-5 hybridizes to a target sequence of the truncated TrkC. In some cases, the nucleic acid polymer comprising at least 94% sequence identity to a nucleic acid sequence selected from SEQ ID NOs: 1-5 hybridizes to a target sequence of the truncated TrkC. In some cases, the nucleic acid polymer comprising at least 95% sequence identity to a nucleic acid sequence selected from SEQ ID NOs: 1-5 hybridizes to a target sequence of the truncated TrkC. In some cases, the nucleic acid polymer comprising at least 96% sequence identity to a nucleic acid sequence selected from SEQ ID NOs: 1-5 hybridizes to a target sequence of the truncated TrkC. In some cases, the nucleic acid polymer comprising at least 97% sequence identity to a nucleic acid sequence selected from SEQ ID NOs: 1-5 hybridizes to a target sequence of the truncated TrkC. In some cases, the nucleic acid polymer comprising at least 98% sequence identity to a nucleic acid sequence selected from SEQ ID NOs: 1-5 hybridizes to a target sequence of the truncated TrkC. In some cases, the nucleic acid polymer comprising at least 99% sequence identity to a nucleic acid sequence selected from SEQ ID NOs: 1-5 hybridizes to a target sequence of the truncated TrkC. In some cases, the nucleic acid polymer comprising 100% sequence identity to a nucleic acid sequence selected from SEQ ID NOs: 1-5 hybridizes to a target sequence of the truncated TrkC. In some cases, the nucleic acid polymer consisting of a nucleic acid sequence selected from SEQ ID NOs: 1-5 hybridizes to a target sequence of the truncated TrkC.

In some instances, the nucleic acid polymer comprising at least 81%, 82%, 83%, 84%, 85%, 86%, 87%, 88%, 89%, 90%, 91%, 92%, 93%, 94%, 95%, 96%, 97%, 98%, or 99% sequence identity to a nucleic acid sequence that hybridizes to a target sequence of the truncated TrkB. In some instances, the nucleic acid polymer comprising 100% sequence identity to a nucleic acid sequence that hybridizes to a target sequence of the truncated TrkB. In some cases, the nucleic acid polymer consisting of a nucleic acid sequence that hybridizes to a target sequence of the truncated TrkB.

In some cases, the nucleic acid polymer comprising at least 81%, 82%, 83%, 84%, 85%, 86%, 87%, 88%, 89%, 90%, 91%, 92%, 93%, 94%, 95%, 96%, 97%, 98%, or 99% sequence identity to a nucleic acid sequence selected from SEQ ID NOs: 114-119 hybridizes to a target sequence of the truncated TrkB. In some cases, the nucleic acid polymer comprising at least 81% sequence identity to a nucleic acid sequence selected from SEQ ID NOs: 114-119 hybridizes to a target sequence of the truncated TrkB. In some cases, the nucleic acid polymer comprising at least 82% sequence identity to a nucleic acid sequence selected from SEQ ID NOs: 114-119 hybridizes to a target sequence of the truncated TrkB. In some cases, the nucleic acid polymer comprising at least 83% sequence identity to a nucleic acid sequence selected from SEQ ID NOs: 114-119 hybridizes to a target sequence of the truncated TrkB. In some cases, the nucleic acid polymer comprising at least 84% sequence identity to a nucleic acid sequence selected from SEQ ID NOs: 114-119 hybridizes to a target sequence of the truncated TrkB. In some cases, the nucleic acid polymer comprising at least 85% sequence identity to a nucleic acid sequence selected from SEQ ID NOs: 114-119 hybridizes to a target sequence of the truncated TrkB. In some cases, the nucleic acid polymer comprising at least 86% sequence identity to a nucleic acid sequence selected from SEQ ID NOs: 114-119 hybridizes to a target sequence of the truncated TrkB. In some cases, the nucleic acid polymer comprising at least 87% sequence identity to a nucleic acid sequence selected from SEQ ID NOs: 114-119 hybridizes to a target sequence of the truncated TrkB. In some cases, the nucleic acid polymer comprising at least 88% sequence identity to a nucleic acid sequence selected from SEQ ID NOs: 114-119 hybridizes to a target sequence of the truncated TrkB. In some cases, the nucleic acid polymer comprising at least 89% sequence identity to a nucleic acid sequence selected from SEQ ID NOs: 114-119 hybridizes to a target sequence of the truncated TrkB. In some cases, the nucleic acid polymer comprising at least 90% sequence identity to a nucleic acid sequence selected from SEQ ID NOs: 114-119 hybridizes to a target sequence of the truncated TrkB. In some cases, the nucleic acid polymer comprising at least 91% sequence identity to a nucleic acid sequence selected from SEQ ID NOs: 114-119 hybridizes to a target sequence of the truncated TrkB. In some cases, the nucleic acid polymer comprising at least 92% sequence identity to a nucleic acid sequence selected from SEQ ID NOs: 114-119 hybridizes to a target sequence of the truncated TrkB. In some cases, the nucleic acid polymer comprising at least 93% sequence identity to a nucleic acid sequence selected from SEQ ID NOs: 114-119 hybridizes to a target sequence of the truncated TrkB. In some cases, the nucleic acid polymer comprising at least 94% sequence identity to a nucleic acid sequence selected from SEQ ID NOs: 114-119 hybridizes to a target sequence of the truncated TrkB. In some cases, the nucleic acid polymer comprising at least 95% sequence identity to a nucleic acid sequence selected from SEQ ID NOs: 114-119 hybridizes to a target sequence of the truncated TrkB. In some cases, the nucleic acid polymer comprising at least 96% sequence identity to a nucleic acid sequence selected from SEQ ID NOs: 114-119 hybridizes to a target sequence of the truncated TrkB. In some cases, the nucleic acid polymer comprising at least 97% sequence identity to a nucleic acid sequence selected from SEQ ID NOs: 114-119 hybridizes to a target sequence of the truncated TrkB. In some cases, the nucleic acid polymer comprising at least 98% sequence identity to a nucleic acid sequence selected from SEQ ID NOs: 114-119 hybridizes to a target sequence of the truncated TrkB. In some cases, the nucleic acid polymer comprising at least 99% sequence identity to a nucleic acid sequence selected from SEQ ID NOs: 114-119 hybridizes to a target sequence of the truncated TrkB. In some cases, the nucleic acid polymer comprising 100% sequence identity to a nucleic acid sequence selected from SEQ ID NOs: 114-119 hybridizes to a target sequence of the truncated TrkB. In some cases, the nucleic acid polymer consisting of a nucleic acid sequence selected from SEQ ID NOs: 114-119 hybridizes to a target sequence of the truncated TrkB.

In some instances, described herein also includes a pharmaceutical composition that comprises a nucleic acid polymer that hybridizes to a target sequence comprising a binding motif selected from CCAAUC, CUCCAA, or ACUGUG, wherein the binding motif is located in a sequence encoding a truncated TrkC. In some instances, the nucleic acid polymer hybridizes to a target sequence that is located at the 3'UTR region of the truncated TrkC mRNA. In some cases, the nucleic acid polymer comprises a short hairpin RNA (shRNA) molecule, a microRNA (miRNA) molecule, a siRNA molecule, or a double stranded RNA molecule. In some cases, the nucleic acid polymer is a shRNA molecule.

In some embodiments, further described herein includes a pharmaceutical composition that comprises a nucleic acid polymer that hybridizes to a target sequence on truncated TrkC or truncated TrkB that is recognized by a microRNA (miRNA). In some instances, the miRNA comprises let-7b-3p (SEQ ID NO: 13), let-7b-5p (SEQ ID NO: 14), miR-1-3p (SEQ ID NO: 15), miR-1-5p (SEQ ID NO: 16), miR-9-3p (SEQ ID NO: 17), miR-9-5p (SEQ ID NO: 18), miR-10a-3p (SEQ ID NO: 19), miR-10a-5p (SEQ ID NO: 20), miR-15a-3p (SEQ ID NO: 21), miR-15a-5p (SEQ ID NO: 22), miR-16-1-3p (SEQ ID NO: 23), miR-16-2-3p (SEQ ID NO: 24), miR-16-5p (SEQ ID NO: 25), miR-17-3p (SEQ ID NO: 26), miR-17-5p (SEQ ID NO: 27), miR-18a-3p (SEQ ID NO: 28), miR-18a-5p (SEQ ID NO: 29), miR-20a-3p (SEQ ID NO: 30), miR-20a-5p (SEQ ID NO: 31), miR-24-3p (SEQ ID NO: 32), miR-24-1-5p (SEQ ID NO: 33), miR-24-2-5p (SEQ ID NO: 34), miR-30e-3p (SEQ ID NO: 35), miR-30e-5p (SEQ ID NO: 36), miR-93-3p (SEQ ID NO: 37), miR-93-5p (SEQ ID NO: 38), miR-103a-3p (SEQ ID NO: 39), miR-103a-2-5p (SEQ ID NO: 40), miR-103b (SEQ ID NO: 41), miR-106a-3p (SEQ ID NO: 42), miR-106a-5p (SEQ ID NO: 43), miR-106b-3p (SEQ ID NO: 44), miR-106b-5p (SEQ ID NO: 45), miR-107 (SEQ ID NO: 46), miR-125a-3p (SEQ ID NO: 47), miR-125a-5p (SEQ ID NO: 48), miR-125b-1-3p (SEQ ID NO: 49), miR-125b-2-3p (SEQ ID NO: 50), miR-125b-5p (SEQ ID NO: 51), miR-128-3p (SEQ ID NO: 52), miR-128-1-5p (SEQ ID NO: 53), miR-128-2-5p (SEQ ID NO: 54), miR-133a-3p (SEQ ID NO: 55), miR-133a-5p (SEQ ID NO: 56), miR-133b (SEQ ID NO: 57), miR-141-3p (SEQ ID NO: 58), miR-141-5p (SEQ ID NO: 59), miR-149-3p (SEQ ID NO: 60), miR-149-5p (SEQ ID NO: 61), miR-182-3p (SEQ ID NO: 62), miR-182-5p (SEQ ID NO: 63), miR-188-3p (SEQ ID NO: 64), miR-188-5p (SEQ ID NO: 65), miR-198 (SEQ ID NO: 66), miR-200a-3p (SEQ ID NO: 67), miR-200a-5p (SEQ ID NO: 68), miR-200b-3p (SEQ ID NO: 69), miR-200b-5p (SEQ ID NO: 70), miR-204-3p (SEQ ID NO: 71), miR-204-5p (SEQ ID NO: 72), miR-206 (SEQ ID NO: 73), miR-221-3p (SEQ ID NO: 74), miR-221-5p (SEQ ID NO: 75), miR-296-3p (SEQ ID NO: 76), miR-296-5p (SEQ ID NO: 77), miR-324-5p (SEQ ID NO: 78), miR-326 (SEQ ID NO: 79), miR-330-3p (SEQ ID NO: 80), miR-331-3p (SEQ ID NO: 81), miR-331-5p (SEQ ID NO: 82), miR-340-3p (SEQ ID NO: 83), miR-340-5p (SEQ ID NO: 84), miR-345-3p (SEQ ID NO: 85), miR-345-5p (SEQ ID NO: 86), miR-374a-3p (SEQ ID NO: 87), miR-374a-5p (SEQ ID NO: 88), miR-374b-3p (SEQ ID NO: 89), miR-374b-5p (SEQ ID NO: 90), miR-374c-3p (SEQ ID NO: 91), miR-374c-5p (SEQ ID NO: 92), miR-384 (SEQ ID NO: 93), miR-412-3p (SEQ ID NO: 94), miR-412-5p (SEQ ID NO: 95), miR-422a (SEQ ID NO: 96), miR-449a (SEQ ID NO: 97), miR-449b-3p (SEQ ID NO: 98), miR-449b-5p (SEQ ID NO: 99), miR-449c-3p (SEQ ID NO: 100), miR-449c-5p (SEQ ID NO: 101), miR-485-3p (SEQ ID NO: 102), miR-509-3p (SEQ ID NO: 103), miR-509-5p (SEQ ID NO: 104), miR-509-3-5p (SEQ ID NO: 105), miR-617 (SEQ ID NO: 106), miR-625-3p (SEQ ID NO: 107), miR-625-5p (SEQ ID NO: 108), miR-765 (SEQ ID NO: 109), miR-768-5p, Hsa-miR-185* or Hsa-miR-491-3p. In some cases, the nucleic acid polymer hybridizes to a target sequence on truncated TrkC or truncated TrkB that is recognized by let-7b-3p (SEQ ID NO: 13), let-7b-5p (SEQ ID NO: 14), miR-1-3p (SEQ ID NO: 15), miR-1-5p (SEQ ID NO: 16), miR-9-3p (SEQ ID NO: 17), miR-9-5p (SEQ ID NO: 18), miR-10a-3p (SEQ ID NO: 19), miR-10a-5p (SEQ ID NO: 20), miR-15a-3p (SEQ ID NO: 21), miR-15a-5p (SEQ ID NO: 22), miR-16-1-3p (SEQ ID NO: 23), miR-16-2-3p (SEQ ID NO: 24), miR-16-5p (SEQ ID NO: 25), miR-17-3p (SEQ ID NO: 26), miR-17-5p (SEQ ID NO: 27), miR-18a-3p (SEQ ID NO: 28), miR-18a-5p (SEQ ID NO: 29), miR-20a-3p (SEQ ID NO: 30), miR-20a-5p (SEQ ID NO: 31), miR-24-3p (SEQ ID NO: 32), miR-24-1-5p (SEQ ID NO: 33), miR-24-2-5p (SEQ ID NO: 34), miR-30e-3p (SEQ ID NO: 35), miR-30e-5p (SEQ ID NO: 36), miR-93-3p (SEQ ID NO: 37), miR-93-5p (SEQ ID NO: 38), miR-103a-3p (SEQ ID NO: 39), miR-103a-2-5p (SEQ ID NO: 40), miR-103b (SEQ ID NO: 41), miR-106a-3p (SEQ ID NO: 42), miR-106a-5p (SEQ ID NO: 43), miR-106b-3p (SEQ ID NO: 44), miR-106b-5p (SEQ ID NO: 45), miR-107 (SEQ ID NO: 46), miR-125a-3p (SEQ ID NO: 47), miR-125a-5p (SEQ ID NO: 48), miR-125b-1-3p (SEQ ID NO: 49), miR-125b-2-3p (SEQ ID NO: 50), miR-125b-5p (SEQ ID NO: 51), miR-128-3p (SEQ ID NO: 52), miR-128-1-5p (SEQ ID NO: 53), miR-128-2-5p (SEQ ID NO: 54), miR-133a-3p (SEQ ID NO: 55), miR-133a-5p (SEQ ID NO: 56), miR-133b (SEQ ID NO: 57), miR-141-3p (SEQ ID NO: 58), miR-141-5p (SEQ ID NO: 59), miR-149-3p (SEQ ID NO: 60), miR-149-5p (SEQ ID NO: 61), miR-182-3p (SEQ ID NO: 62), miR-182-5p (SEQ ID NO: 63), miR-188-3p (SEQ ID NO: 64), miR-188-5p (SEQ ID NO: 65), miR-198 (SEQ ID NO: 66), miR-200a-3p (SEQ ID NO: 67), miR-200a-5p (SEQ ID NO: 68), miR-200b-3p (SEQ ID NO: 69), miR-200b-5p (SEQ ID NO: 70), miR-204-3p (SEQ ID NO: 71), miR-204-5p (SEQ ID NO: 72), miR-206 (SEQ ID NO: 73), miR-221-3p (SEQ ID NO: 74), miR-221-5p (SEQ ID NO: 75), miR-296-3p (SEQ ID NO: 76), miR-296-5p (SEQ ID NO: 77), miR-324-5p (SEQ ID NO: 78), miR-326 (SEQ ID NO: 79), miR-330-3p (SEQ ID NO: 80), miR-331-3p (SEQ ID NO: 81), miR-331-5p (SEQ ID NO: 82), miR-340-3p (SEQ ID NO: 83), miR-340-5p (SEQ ID NO: 84), miR-345-3p (SEQ ID NO: 85), miR-345-5p (SEQ ID NO: 86), miR-374a-3p (SEQ ID NO: 87), miR-374a-5p (SEQ ID NO: 88), miR-374b-3p (SEQ ID NO: 89), miR-374b-5p (SEQ ID NO: 90), miR-374c-3p (SEQ ID NO: 91), miR-374c-5p (SEQ ID NO: 92), miR-384 (SEQ ID NO: 93), miR-412-3p (SEQ ID NO: 94), miR-412-5p (SEQ ID NO: 95), miR-422a (SEQ ID NO: 96), miR-449a (SEQ ID NO: 97), miR-449b-3p (SEQ ID NO: 98), miR-449b-5p (SEQ ID NO: 99), miR-449c-3p (SEQ ID NO: 100), miR-449c-5p (SEQ ID NO: 101), miR-485-3p (SEQ ID NO: 102), miR-509-3p (SEQ ID NO: 103), miR-509-5p (SEQ ID NO: 104), miR-509-3-5p (SEQ ID NO: 105), miR-617 (SEQ ID NO: 106), miR-625-3p (SEQ ID NO: 107), miR-625-5p (SEQ ID NO: 108), miR-765 (SEQ ID NO: 109), miR-768-5p, Hsa-miR-185* or Hsa-miR-491-3p. In some cases, the nucleic acid polymer hybridizes to a target sequence on truncated TrkC or truncated TrkB that is recognized by miR-128-3p (SEQ ID NO: 52), miR-128-1-5p (SEQ ID NO: 53), miR-128-2-5p (SEQ ID NO: 54), miR-509-3p (SEQ ID NO: 103), miR-509-5p (SEQ ID NO: 104), miR-509-3-5p (SEQ ID NO: 105), miR-768-5p, Hsa-miR-185* or Hsa-miR-491-3p. In some cases, the nucleic acid polymer hybridizes to a target sequence on truncated TrkC or truncated TrkB that is recognized by miR-128-3p (SEQ ID NO: 52), miR-128-1-5p (SEQ ID NO: 53), miR-128-2-5p (SEQ ID NO: 54). In some cases, the nucleic acid polymer hybridizes to a target sequence on truncated TrkC or truncated TrkB that is recognized by miR-509-3p (SEQ ID NO: 103), miR-509-5p (SEQ ID NO: 104), miR-509-3-5p (SEQ ID NO: 105). In some cases, the nucleic acid polymer hybridizes to a target sequence on truncated TrkC or truncated TrkB that is recognized by miR-768-5p. In some cases, the nucleic acid polymer hybridizes to a target sequence on truncated TrkC or truncated TrkB that is recognized by Hsa-miR-185*. In some cases, the nucleic acid polymer hybridizes to a target sequence on truncated TrkC or truncated TrkB that is recognized by Hsa-miR-491-3p. In some instances, Hsa-miR-185* and Hsa-miR-491-3p are as described in Maussion, et al., "Regulation of a truncated form of tropomyosin-related kinase B (TrkB) by Hsa-miR-185* in frontal cortex of suicide completers," PLoS One 7(6): e39301 (2012).

In some embodiments, the nucleic acid polymer is at most 100 nucleotides in length. In some embodiments, the nucleic acid polymer is at most 5, 10, 11, 12, 13, 14, 15, 16, 17, 18, 19, 20, 21, 22, 23, 24, 25, 26, 27, 28, 29, 30, 31, 32, 33, 34, 35, 40, 45, 50, 55, 60, 70, 80, 90, or 100 nucleotides in length. In some embodiments, the nucleic acid polymer is about 10 nucleotides in length. In some embodiments, the nucleic acid polymer is about 11 nucleotides in length. In some embodiments, the nucleic acid polymer is about 12 nucleotides in length. In some embodiments, the nucleic acid polymer is about 13 nucleotides in length. In some embodiments, the nucleic acid polymer is about 14 nucleotides in length. In some embodiments, the nucleic acid polymer is about 15 nucleotides in length. In some embodiments, the nucleic acid polymer is about 16 nucleotides in length. In some embodiments, the nucleic acid polymer is about 17 nucleotides in length. In some embodiments, the nucleic acid polymer is about 18 nucleotides in length. In some embodiments, the nucleic acid polymer is about 19 nucleotides in length. In some embodiments, the nucleic acid polymer is about 20 nucleotides in length. In some embodiments, the nucleic acid polymer is about 21 nucleotides in length. In some embodiments, the nucleic acid polymer is about 22 nucleotides in length. In some embodiments, the nucleic acid polymer is about 23 nucleotides in length. In some embodiments, the nucleic acid polymer is about 24 nucleotides in length. In some embodiments, the nucleic acid polymer is about 25 nucleotides in length. In some embodiments, the nucleic acid polymer is about 26 nucleotides in length. In some embodiments, the nucleic acid polymer is about 27 nucleotides in length. In some embodiments, the nucleic acid polymer is about 28 nucleotides in length. In some embodiments, the nucleic acid polymer is about 29 nucleotides in length. In some embodiments, the nucleic acid polymer is about 30 nucleotides in length. In some embodiments, the nucleic acid polymer is about 31 nucleotides in length. In some embodiments, the nucleic acid polymer is about 32 nucleotides in length. In some embodiments, the nucleic acid polymer is about 33 nucleotides in length. In some embodiments, the nucleic acid polymer is about 34 nucleotides in length. In some embodiments, the nucleic acid polymer is about 35 nucleotides in length. In some embodiments, the nucleic acid polymer is about 36 nucleotides in length. In some embodiments, the nucleic acid polymer is about 37 nucleotides in length. In some embodiments, the nucleic acid polymer is about 38 nucleotides in length. In some embodiments, the nucleic acid polymer is about 39 nucleotides in length. In some embodiments, the nucleic acid polymer is about 40 nucleotides in length. In some embodiments, the nucleic acid polymer is about 45 nucleotides in length. In some embodiments, the nucleic acid polymer is about 50 nucleotides in length. In some embodiments, the nucleic acid polymer is about 55 nucleotides in length. In some embodiments, the nucleic acid polymer is about 60 nucleotides in length. In some embodiments, the nucleic acid polymer is about 70 nucleotides in length. In some embodiments, the nucleic acid polymer is about 80 nucleotides in length.

In some embodiments, the nucleic acid polymer is between about 10 and about 80 nucleotides in length. In some embodiments, the nucleic acid polymer is between about 10 and about 70 nucleotides in length. In some embodiments, the nucleic acid polymer is between about 10 and about 60 nucleotides in length. In some embodiments, the nucleic acid polymer is between about 10 and about 55 nucleotides in length. In some embodiments, the nucleic acid polymer is between about 10 and about 50 nucleotides in length. In some embodiments, the nucleic acid polymer is between about 10 and about 45 nucleotides in length. In some embodiments, the nucleic acid polymer is between about 10 and about 40 nucleotides in length. In some embodiments, the nucleic acid polymer is between about 10 and about 35 nucleotides in length. In some embodiments, the nucleic acid polymer is between about 10 and about 30 nucleotides in length. In some embodiments, the nucleic acid polymer is between about 10 and about 25 nucleotides in length. In some embodiments, the nucleic acid polymer is between about 10 and about 20 nucleotides in length.

In some embodiments, the nucleic acid polymer comprises a short hairpin RNA (shRNA) molecule, a microRNA (miRNA) molecule, or a siRNA molecule. In some embodiments, the nucleic acid polymer further comprises a complement nucleic acid polymer to form a double stranded RNA molecule.

In some embodiments, the nucleic acid polymer is a shRNA molecule. In some embodiments, the shRNA molecule comprises at least 80% sequence identity to a nucleic acid sequence selected from SEQ ID NOs: 1-5 and 114-119. In some instances, the shRNA molecule comprises at least 85%, 90%, 91%, 92%, 93%, 94%, 95%, 96%, 97%, 98%, or 99% sequence identity to a nucleic acid sequence selected from SEQ ID NOs: 1-5 and 114-119. In some instances, the shRNA molecule comprises at least 85% sequence identity to a nucleic acid sequence selected from SEQ ID NOs: 1-5 and 114-119. In some instances, the shRNA molecule comprises at least 90% sequence identity to a nucleic acid sequence selected from SEQ ID NOs: 1-5 and 114-119. In some instances, the shRNA molecule comprises at least 91% sequence identity to a nucleic acid sequence selected from SEQ ID NOs: 1-5 and 114-119. In some instances, the shRNA molecule comprises at least 92% sequence identity to a nucleic acid sequence selected from SEQ ID NOs: 1-5 and 114-119. In some instances, the shRNA molecule comprises at least 93% sequence identity to a nucleic acid sequence selected from SEQ ID NOs: 1-5 and 114-119. In some instances, the shRNA molecule comprises at least 94% sequence identity to a nucleic acid sequence selected from SEQ ID NOs: 1-5 and 114-119. In some instances, the shRNA molecule comprises at least 95% sequence identity to a nucleic acid sequence selected from SEQ ID NOs: 1-5 and 114-119. In some instances, the shRNA molecule comprises at least 96% sequence identity to a nucleic acid sequence selected from SEQ ID NOs: 1-5 and 114-119. In some instances, the shRNA molecule comprises at least 97% sequence identity to a nucleic acid sequence selected from SEQ ID NOs: 1-5 and 114-119. In some instances, the shRNA molecule comprises at least 98% sequence identity to a nucleic acid sequence selected from SEQ ID NOs: 1-5 and 114-119. In some instances, the shRNA molecule comprises at least 99% sequence identity to a nucleic acid sequence selected from SEQ ID NOs: 1-5 and 114-119. In some instances, the shRNA molecule comprises 100% sequence identity to a nucleic acid sequence selected from SEQ ID NOs: 1-5 and 114-119. In some instances, the shRNA molecule consists of a nucleic acid sequence selected from SEQ ID NOs: 1-5 and 114-119.

In some embodiments, the shRNA molecule hybridizes to a target sequence comprising a binding motif selected from CCAAUC, CUCCAA, or ACUGUG, wherein the binding motif is located in a sequence encoding a truncated TrkC. In some instances, the target sequence is located at the 3'UTR region of the truncated TrkC mRNA.

In some instances, the shRNA molecule is at most 100 nucleotides in length. In some embodiments, the shRNA molecule is at most 5, 10, 11, 12, 13, 14, 15, 16, 17, 18, 19, 20, 21, 22, 23, 24, 25, 26, 27, 28, 29, 30, 31, 32, 33, 34, 35, 40, 45, 50, 55, 60, 70, 80, 90, or 100 nucleotides in length. In some embodiments, the shRNA molecule is between about 10 and about 80 nucleotides in length. In some embodiments, the shRNA molecule is between about 10 and about 70 nucleotides in length. In some embodiments, the shRNA molecule is between about 10 and about 60 nucleotides in length. In some embodiments, the shRNA molecule is between about 10 and about 55 nucleotides in length. In some embodiments, the shRNA molecule is between about 10 and about 50 nucleotides in length. In some embodiments, the shRNA molecule is between about 10 and about 45 nucleotides in length. In some embodiments, the shRNA molecule is between about 10 and about 40 nucleotides in length. In some embodiments, the shRNA molecule is between about 10 and about 35 nucleotides in length. In some embodiments, the shRNA molecule is between about 10 and about 30 nucleotides in length. In some embodiments, the shRNA molecule is between about 10 and about 25 nucleotides in length. In some embodiments, the shRNA molecule is between about 10 and about 20 nucleotides in length.

In some embodiments, the nucleic acid polymer described herein comprises RNA, DNA or a combination thereof. In some instances, the nucleic acid polymer is a RNA polymer. In some instances, the nucleic acid polymer is further modified at the nucleoside moiety, at the phosphate moiety, or a combination thereof. In some cases, the nucleic acid polymer further comprises one or more artificial nucleotide bases.

In some instances, the one or more artificial nucleotide bases comprises 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O—N-methylacetamido (2'-O-NMA) modified, locked nucleic acid (LNA), ethylene nucleic acid (ENA), peptide nucleic acid (PNA), 1', 5'-anhydrohexitol nucleic acids (HNA), morpholino, methylphosphonate nucleotides, thiolphosphonate nucleotides, or 2'-fluoro N3-P5'-phosphoramidites.

In some embodiments, the nucleic acid polymer comprises a modification at the nucleoside moiety. In some instances, the modification is at the 2' hydroxyl group of the ribose moiety. In some instances, the modification is a 2'-O-methyl modification or a 2'-O-methoxyethyl (2'-O-MOE) modification. In some instances, the 2'-O-methyl modification adds a methyl group to the 2' hydroxyl group of the ribose moiety whereas the 2'O-methoxyethyl modification add a methoxyethyl group to the 2' hydroxyl group of the ribose moiety. Exemplary chemical structures of a 2'-O-methyl modification of an adenosine molecule and 2'O-methoxyethyl modification of a uridine are illustrated below.

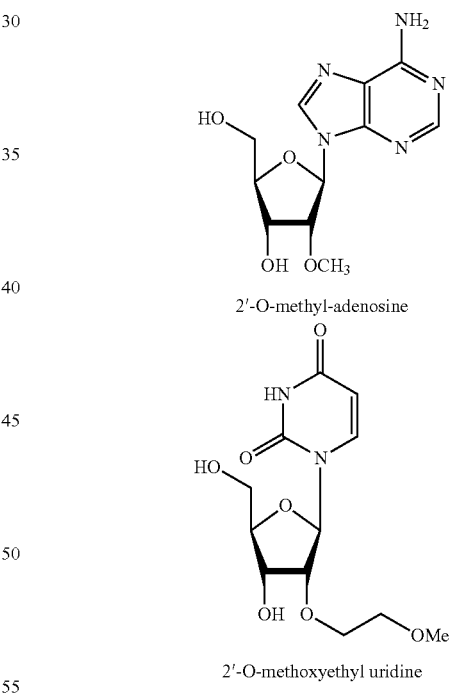

2'-O-methyl-adenosine

2'-O-methoxyethyl uridine

In some embodiments, an additional modification at the 2' hydroxyl group includes a 2'-O-aminopropyl sugar conformation which involves an extended amine group comprising a propyl linker that binds the amine group to the 2' oxygen. In some instances, this modification neutralizes the phosphate derived overall negative charge of the oligonucleotide molecule by introducing one positive charge from the amine group per sugar and thereby improve cellular uptake properties due to its zwitterionic properties. An exemplary chemical structure of a 2'-O-aminopropyl nucleoside phosphoramidite is illustrated below.

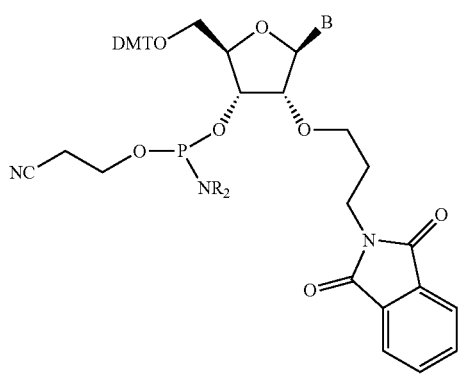

2'-O-aminopropyl nucleoside phosphoramidite

In some embodiments, the modification at the 2' hydroxyl group includes a locked or bridged ribose conformation (e.g., locked nucleic acid or LNA) where the 4' ribose position is also involved. In some embodiments, the oxygen molecule bound at the 2' carbon is linked to the 4' carbon by a methylene group, thus forming a 2'-C,4'-C-oxy-methylene-linked bicyclic ribonucleotide monomer. Exemplary representations of the chemical structure of LNA are illustrated below. The representation shown to the left highlights the chemical connectivities of an LNA monomer. The representation shown to the right highlights the locked 3'-endo ($^3$E) conformation of the furanose ring of an LNA monomer.

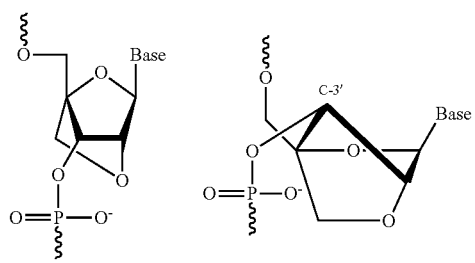

LNA (Locked Nucleic Acids)

In some embodiments, a further modification at the 2' hydroxyl group comprises ethylene nucleic acids (ENA) such as for example 2'-4'-ethylene-bridged nucleic acid, which locks the sugar conformation into a $C_3$'-endo sugar puckering conformation. In some instances, ENAs are part of the bridged nucleic acids class of modified nucleic acids that also comprises LNA. Exemplary chemical structures of the ENA and bridged nucleic acids are illustrated below.

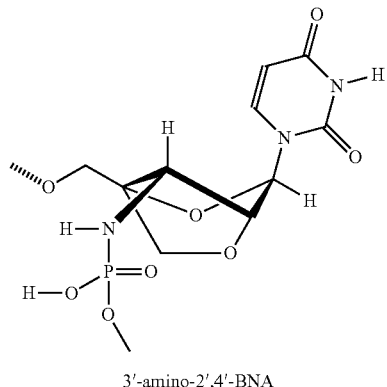

3'-amino-2',4'-BNA

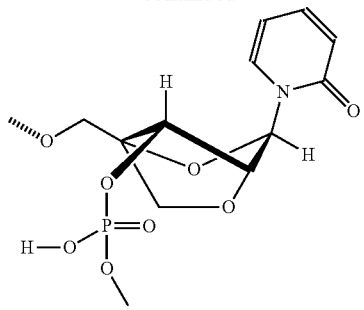

2',4'-BNA-2-pyridone

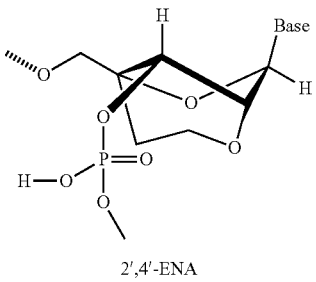

2',4'-ENA

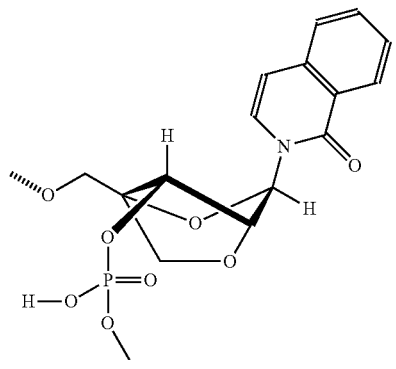

2',4'-BNA-1-isoquinolone

In some embodiments, still other modifications at the 2' hydroxyl group include 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O—N-methylacetamido (2'-O-NMA).

In some embodiments, nucleotide analogues further comprise Morpholinos, peptide nucleic acids (PNAs), methylphosphonate nucleotides, thiolphosphonate nucleotides, 2'-fluoro N3-P5'-phosphoramidites, 1', 5'-anhydrohexitol nucleic acids (HNAs), or a combination thereof. In some instances, morpholino or phosphorodiamidate morpholino oligo (PMO) comprises synthetic molecules whose structure mimics natural nucleic acid structure by deviates from the normal sugar and phosphate structures. Instead, the five member ribose ring in some instances is substituted with a six member morpholino ring containing four carbons, one nitrogen and one oxygen. In some cases, the ribose monomers are linked by a phosphordiamidate group instead of a phosphate group. In some cases, these backbone alterations remove all positive and negative charges making morpholinos neutral molecules that cross cellular membranes without the aid of cellular delivery agents such as those used by charged oligonucleotides.

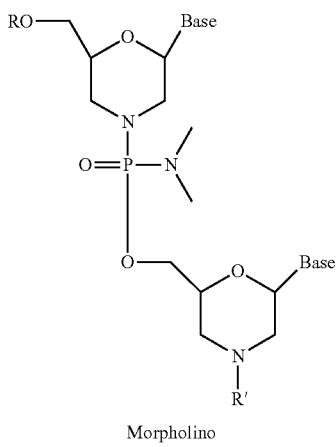

Morpholino

In some embodiments, peptide nucleic acid (PNA) does not contain sugar ring or phosphate linkage. Instead, the bases in some instances are attached and appropriately spaced by oligoglycine-like molecules, therefore, eliminating a backbone charge.

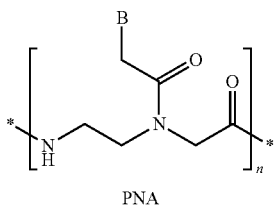

PNA

In some embodiments, modification of the phosphate backbone also comprise methyl or thiol modifications such as thiolphosphonate and methylphosphonate nucleotide. Exemplary thiolphosphonate nucleotide (left) and methylphosphonate nucleotide (right) are illustrated below.

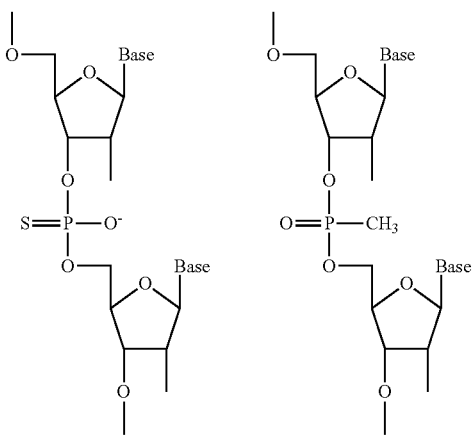

Furthermore, exemplary 2'-fluoro N3-P5'-phosphoramidites is illustrated as:

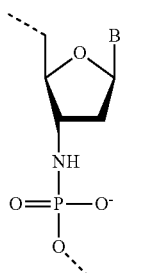

N3'-P5' Phosphoroamidate

And exemplary hexitol nucleic acid (or 1', 5'-anhydrohexitol nucleic acids (HNA)) is illustrated as:

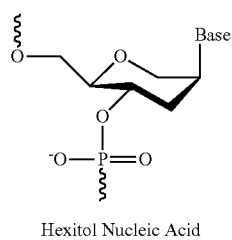

Hexitol Nucleic Acid

In some embodiments, also disclosed herein include a vector which comprises a nucleic acid polymer described herein and methods of treatment. In some embodiments, the vector comprises a nucleic acid polymer wherein the nucleic acid polymer comprises at least 80%, 85%, 90%, 95%, or 99% sequence identity to a nucleic acid sequence selected from SEQ ID NOs: 1-5 and 114-119. In some instances, the vector comprises a nucleic acid polymer wherein the nucleic acid polymer consists of a nucleic acid sequence selected from SEQ ID NOs: 1-5 and 114-119.

In some instances, the vector is a viral vector. In some instances, the viral vector is a lentiviral vector. In some instances, the viral vector is an adenoviral vector. In some cases, the vector is delivered through a viral delivery method.

In some cases, the vector is delivered through electroporation, chemical method, microinjection, gene gun, impalefection, hydrodynamics-based delivery, continuous infusion, or sonication. In some cases, the chemical method is lipofection. In some cases, the method is infection, or adsorption or transcytosis.

Small Molecule Antagonists

Disclosed herein, in certain embodiments, also includes a method of treating an otic disease or condition, preventing an otic disease or condition or reducing the progression of an otic disease or condition comprising administering to a patient in need thereof a therapeutic amount of a pharmaceutical composition comprising a small molecule antagonists of a truncated TrkC or truncated TrkB; and a pharmaceutically acceptable excipient and/or a delivery vehicle. In some embodiments, the small molecule antagonist impedes the truncated TrkC or truncated TrkB interaction with a truncated TrkC or truncated TrkB binding partner.

Figure 2:
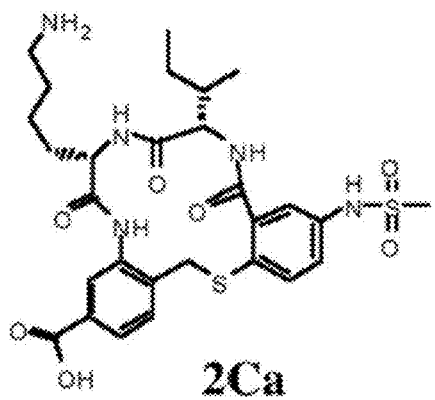
FIG. 2 illustrates exemplary small molecule antagonists of truncated TrkC. The structures of the exemplary small molecule antagonists are adapted from, for example, Brahimi et al (2014), PlosOne 9:e89617.
Figure 2:
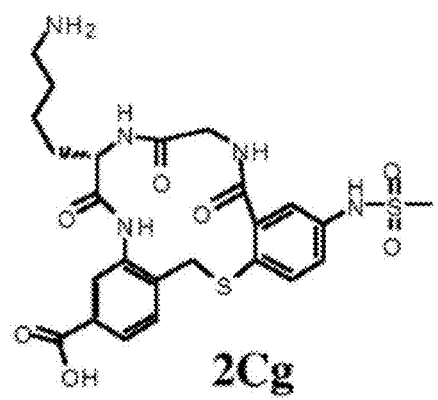
Figure 2:
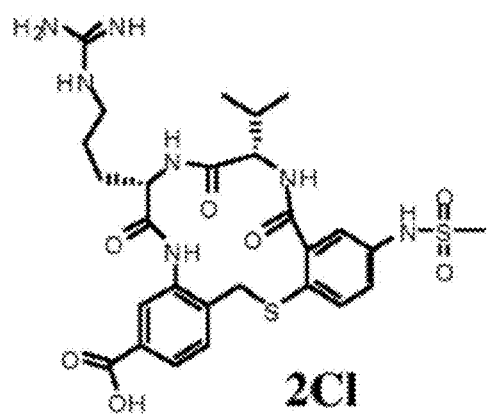
Figure 2:
Figure 2:
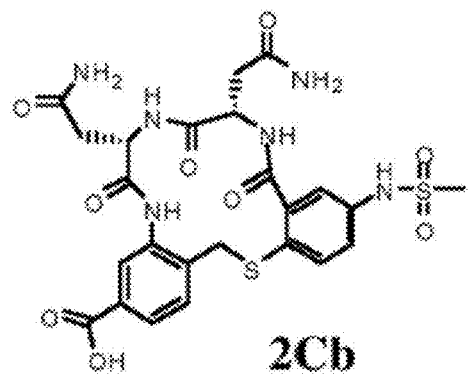
Figure 2:
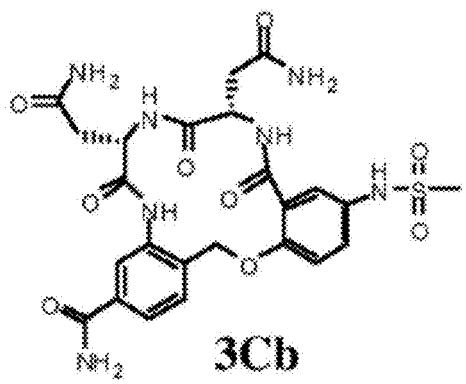
Figure 2:
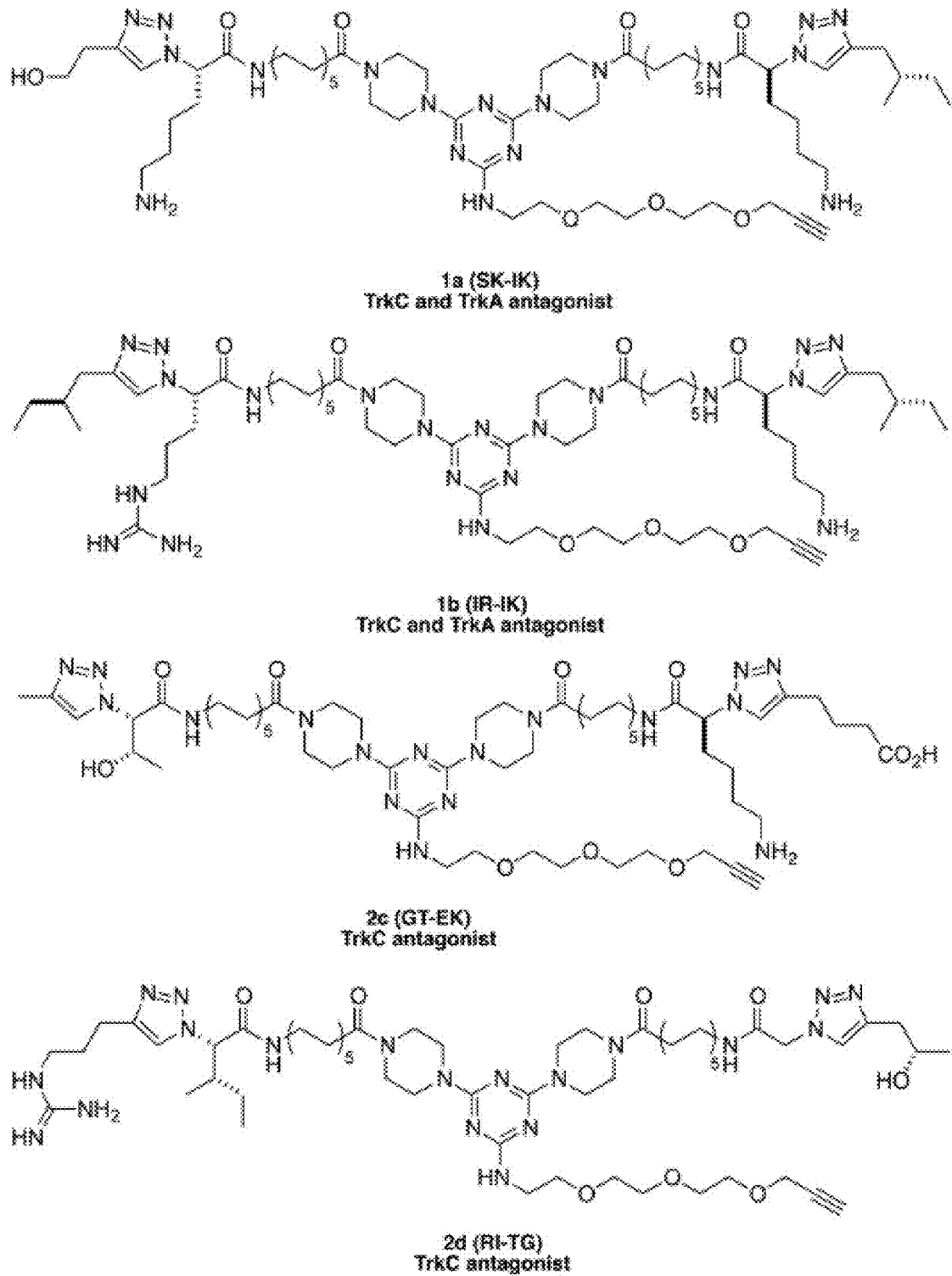
Figure 2:
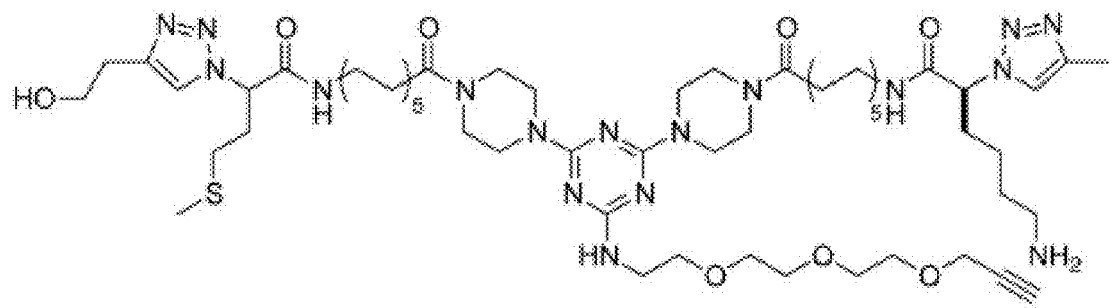
Figure 2:
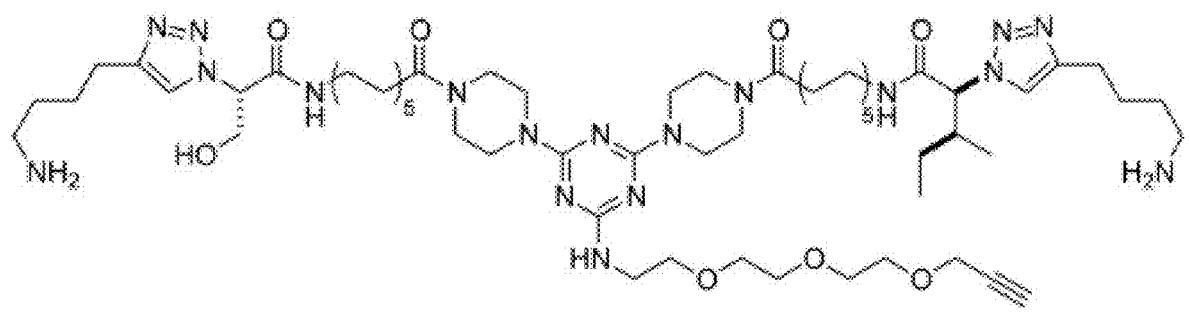
Figure 2:
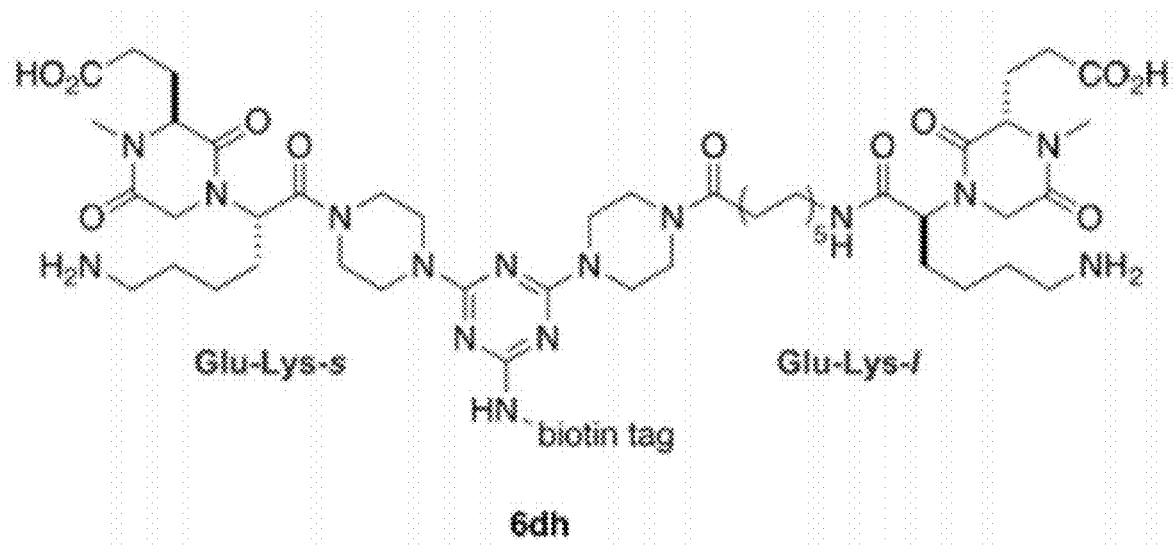

In some instances, the small molecule is a peptidomimetic. In some cases, the small molecule is a small molecule as illustrated in FIG. 2. In some embodiments, the small molecule is a small molecule antagonist described in: Brahimi et al., "A peptidomimetic of NT-3 acts as a TrkC antagonist," *Peptides* 30(10):1833-1839 (2009); Liu et al., "Bivalent diketopiperazine-based tropomysin receptor kinase C (TrkC) antagonists," *J. Med. Chem.* 53(13): 5044-5048 (2010); Bai et al., "In glaucoma the upregulated truncated TrkC.T1 receptor isoform in Glia causes increased TNF-α production, leading to retinal ganglion cell death," Inv. Ophthalm. & Visual Sci. 51(12): 6639-6651 (2010); or Brahimi et al., "Combinatorial assembly of small molecules into bivalent antagonists of TrkC or TrkA receptors," *PLOS One* 9(3): e89617 (2014).

In some embodiments, the small molecule antagonist is a truncated TrkC antagonist. In some embodiments, the truncated TrkC antagonist is a small molecule as illustrated in FIG. 2. In some embodiments, the truncated TrkC antagonists is a small molecule as described in: Brahimi et al., "A peptidomimetic of NT-3 acts as a TrkC antagonist," *Peptides* 30(10):1833-1839 (2009); Liu et al., "Bivalent diketopiperazine-based tropomysin receptor kinase C (TrkC) antagonists," *J. Med. Chem.* 53(13): 5044-5048 (2010); Bai et al., "In glaucoma the upregulated truncated TrkC.T1 receptor isoform in Glia causes increased TNF-α production, leading to retinal ganglion cell death," Inv. Ophthalm. & Visual Sci. 51(12): 6639-6651 (2010); or Brahimi et al., "Combinatorial assembly of small molecules into bivalent antagonists of TrkC or TrkA receptors," *PLOS One* 9(3): e89617 (2014).

In some instances, the truncated TrkC is a non-catalytic truncated TrkC. As described elsewhere herein, the non-catalytic truncated TrkC protein comprises at least 80%, 85%, 90%, 95%, or 99% sequence identity to the amino acid sequence of SEQ ID NO: 10 or 113. In some instances, the truncated TrkC protein consists of the amino acid sequence of SEQ ID NO: 10 or 113. In some instances, the truncated TrkC is TrkC.T1.

In some embodiments, the truncated TrkB is a non-catalytic truncated TrkB. As described elsewhere herein, the non-catalytic truncated TrkB protein comprises at least 80%, 85%, 90%, 95%, or 99% sequence identity to an amino acid sequence selected from SEQ ID NOs: 11-12 and 121-123. In some instances, the truncated TrkB protein consists of an amino acid sequence selected from SEQ ID NOs: 11-12 and 121-123. In some instances, the truncated TrkB is TrkB.T1.

In some embodiments, the truncated TrkC binding partner comprises a neurotropic factor or a microRNA molecule. In some embodiments, the neurotropic factor is neurotrophin-3 (NT-3). In some embodiments, the microRNA molecule comprises miR-128, miR-509, or miR-768-5p. In some embodiments, the truncated TrkB binding partner comprises a neurotropic factor. In some embodiments, the neurotropic factor is brain derived neurotrophic factor (BDNF), neurotrophin-3 (NT-3), or neurotrophin-4 (NT-4).

Polypeptide Antagonists

Disclosed herein, in certain embodiments, further includes a method of treating an otic disease or condition, preventing an otic disease or condition or reducing the progression of an otic disease or condition comprising administering to a patient in need thereof a therapeutic amount of a pharmaceutical composition comprising a polypeptide antagonist of a truncated TrkC or truncated TrkB; and a pharmaceutical acceptable excipient and/or a delivery vehicle.

In some embodiments, the polypeptide antagonist is an antibody or binding fragment thereof. In some instances, the antibody or binding fragment thereof comprises a humanized antibody or binding fragment thereof, chimeric antibody or binding fragment thereof, monoclonal antibody or binding fragment thereof, a linear antibody, a single-chain antibody, a bi-specific antibody, a multispecific antibody formed from antibody fragments, a tandem antibody, a veneered antibody, monovalent Fab', divalent Fab2, single-chain variable fragment (scFv), diabody, minibody, single-domain antibody (sdAb), a rIgG fragment, or camelid antibody or binding fragment thereof.

In some embodiments, the antibody or binding fragment thereof recognizes one or more of the epitopes of the truncated TrkC or truncated TrkB. In some embodiments, the epitopes on the truncated TrkC comprise a region within the ectodomain of the truncated TrkC. In some instances, the ectodomain of the truncated TrkC comprises the leucine-rich repeat regions and the Ig-like domain that is involved in ligand interaction. In some instances, the epitope region within the ectodomain of the truncated TrkC comprises one or more cysteine residues. In some instances, the epitope region within the ectodomain of the truncated TrkC comprises one or more cysteine residues that is capable of forming disulfide bond. In some embodiments, the antibody or binding fragment thereof recognizes one or more of the epitopes that comprises one or more of the cysteine residues.

In some embodiments, the epitopes on the truncated TrkB comprise a region within the ectodomain of the truncated TrkB. In some instances, the ectodomain of the truncated TrkB comprises the leucine-rich repeat regions and the Ig-like domain that is involved in ligand interaction. In some instances, the epitope region within the ectodomain of the truncated TrkB comprises one or more cysteine residues. In some instances, the epitope region within the ectodomain of the truncated TrkB comprises one or more cysteine residues that is capable of forming disulfide bond. In some embodiments, the antibody or binding fragment thereof recognizes one or more of the epitopes that comprises one or more of the cysteine residues.

In some embodiments, the polypeptide antagonist comprises an antibody or binding fragment thereof that recognizes one or more of the epitopes of the truncated TrkC or truncated TrkB. In some instances, the polypeptide antagonist comprises an antibody or binding fragment thereof that recognizes one or more of the epitopes from the ectodomain of either truncated TrkC or truncated TrkB that comprises one or more of the cysteine residues.

In some embodiments, the polypeptide antagonist comprises an antibody or binding fragment thereof that recognizes one or more of the epitopes of the truncated TrkC or truncated TrkB but not one or more of the epitopes of the full-length TrkC or full-length TrkB. In some embodiments, the polypeptide antagonist comprises an antibody or binding fragment thereof that recognizes one or more of the epitopes from the ectodomain of the truncated TrkC or truncated TrkB but not one or more of the epitopes from the ectodomain of the full-length TrkC or full-length TrkB.

In some instances, the truncated TrkC is a non-catalytic truncated TrkC. As described elsewhere herein, the non-catalytic truncated TrkC protein comprises at least 80%, 85%, 90%, 95%, or 99% sequence identity to the amino acid sequence of SEQ ID NO: 10 or 113. In some instances, the truncated TrkC protein consists of the amino acid sequence of SEQ ID NO: 10 or 113. In some instances, the truncated TrkC is TrkC.T1.

In some embodiments, the truncated TrkB is a non-catalytic truncated TrkB. As described elsewhere herein, the non-catalytic truncated TrkB protein comprises at least 80%, 85%, 90%, 95%, or 99% sequence identity to an amino acid sequence selected from SEQ ID NOs: 11-12 and 121-123. In some instances, the truncated TrkB protein consists of an amino acid sequence selected from SEQ ID NOs: 11-12 and 121-123. In some instances, the truncated TrkB is TrkB.T1.

As used herein, the term "antibody" is used in the broadest sense and covers fully assembled antibodies, antibody fragments that bind antigen (e.g., Fab, F(ab')$_2$, Fv, single chain antibodies such as single-chain variable fragment (scFv), diabodies, minibodies, single-domain antibodies (sdAbs) or nanobodies, antibody chimeras, hybrid antibodies, bispecific antibodies, humanized antibodies, and the like), and recombinant peptides comprising the forgoing.

As used herein, the terms "monoclonal antibody" and "mAb" as used herein refer to an antibody obtained from a substantially homogeneous population of antibodies, i.e., the individual antibodies comprising the population are identical except for possible naturally occurring mutations that are present in minor amounts.

"Native antibodies" and "native immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy-chain variable domains.

As used herein, the term "variable" refers to the fact that certain portions of the variable domains differ extensively in sequence among antibodies. Variable regions confer antigen-binding specificity. However, the variability is not evenly distributed throughout the variable domains of antibodies. It is concentrated in three segments called complementarity determining regions (CDRs) or hypervariable regions, both in the light chain and the heavy-chain variable domains. The more highly conserved portions of variable domains are celled in the framework (FR) regions. The variable domains of native heavy and light chains each comprise four FR regions, largely adopting a 13-pleated-sheet configuration, connected by three CDRs, which form loops connecting, and in some cases forming part of, the f3-pleated-sheet structure. The CDRs in each chain are held together in close proximity by the FR regions and, with the CDRs from the other chain, contribute to the formation of the antigen-binding site of antibodies (see, Kabat et al. (1991) NIH PubL. No. 91-3242, Vol. I, pages 647-669). The constant domains are not involved directly in binding an antibody to an antigen, but exhibit various effector functions, such as Fc receptor (FcR) binding, participation of the antibody in antibody-dependent cellular toxicity, initiation of complement dependent cytotoxicity, and mast cell degranulation.

As used herein, the term "hypervariable region," when used herein, refers to the amino acid residues of an antibody that are responsible for antigen-binding. The hypervariable region comprises amino acid residues from a "complementarily determining region" or "CDR" (i.e., residues 24-34 (L1), 5056 (L2), and 89-97 (L3) in the light-chain variable domain and 31-35 (H1), 50-65 (H2), and 95-102 (H3) in the heavy-chain variable domain; Kabat et al. (1991) Sequences of Proteins of Immunological Interest, 5th Ed. Public Health Service, National Institute of Health, Bethesda, Md.) and/or those residues from a "hypervariable loop" (i.e., residues 26-32 (L1), 50-52 (L2), and 91-96 (L3) in the light-chain variable domain and (H1), 53-55 (H2), and 96-101 (13) in the heavy chain variable domain; Clothia and Lesk, (1987) J. Mol. Biol., 196:901-917). "Framework" or "FR" residues are those variable domain residues other than the hypervariable region residues, as herein deemed.

"Antibody fragments" comprise a portion of an intact antibody. In some embodiments, the portion of an intact antibody is an antigen-binding or variable region of the intact antibody. Examples of antibody fragments include Fab, Fab, F(ab')2, and Fv fragments; diabodies; linear antibodies (Zapata et al. (1995) Protein Eng. 10:1057-1062); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen.

"Fv" is the minimum antibody fragment that contains a complete antigen recognition and binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain ($C_{H1}$) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. Fab' fragments are produced by reducing the F(ab')2 fragment's heavy chain disulfide bridge. Other chemical couplings of antibody fragments are also known.

The "light chains" of antibodies (immunoglobulins) from any vertebrate species assigned to one of two clearly distinct types, called kappa (x) and lambda (X), based on the amino acid sequences of their constant domains.

Depending on the amino acid sequence of the constant domain of their heavy chains, immunoglobulins are assigned to different classes. There are five major classes of human immunoglobulins: IgA, IgD, IgE, IgG, and IgM, and several of these are further divided into subclasses (isotypes), e.g., IgG1, IgG2, IgG3, IgG4, IgA1, and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known. Different isotypes have different effector functions. For example, human IgG1 and IgG3 isotypes have ADCC (antibody dependent cell-mediated cytotoxicity) activity.

Methods of Antagonist Delivery

In some embodiments, the pharmaceutical composition comprises a vector in which the vector comprises one or more of the nucleic acid polymer described herein or comprise nucleic acid sequence that encodes a polypeptide described herein. In some embodiments, the nucleic acid polymer comprises at least 80%, 85%, 90%, 95%, or 99% sequence identity to a nucleic acid sequence selected from SEQ ID NOs: 1-5 and 114-119. In some embodiments, the polypeptide is an antibody or binding fragment thereof. In some embodiments, the antibody or binding fragment thereof comprises a humanized antibody or binding fragment thereof, chimeric antibody or binding fragment thereof, monoclonal antibody or binding fragment thereof, monovalent Fab', divalent Fab2, single-chain variable fragment (scFv), diabody, minibody, single-domain antibody (sdAb), or camelid antibody or binding fragment thereof. In some embodiments, the vector is a viral vector.

In some embodiments, the viral vector is obtained from any virus, such as a DNA or an RNA virus. In some embodiments, a DNA virus is a single-stranded (ss) DNA virus, a double-stranded (ds) DNA virus, or a DNA virus that contains both ss and ds DNA regions. In some embodiments, an RNA virus is a single-stranded (ss) RNA virus or a double-stranded (ds) RNA virus. In some embodiments, a ssRNA virus is further classified into a positive-sense RNA virus or a negative-sense RNA virus.

In some instances, the viral vector is obtained from a dsDNA virus of the family: Myoviridae, Podoviridae, Siphoviridae, Alloherpesviridae, Herpesviridae, Malacoherpesviridae, Lipothrixviridae, Rudiviridae, Adenoviridae, Ampullaviridae, Ascoviridae, Asfaviridae, Baculoviridae, Bicaudaviridae, Clavaviridae, Corticoviridae, Fuselloviridae, Globuloviridae, Guttaviridae, Hytrosaviridae, Iridoviridae, Marseilleviridae, Mimiviridae, Nimaviridae, Pandoraviridae, Papillomaviridae, Phycodnaviridae, Plasmaviridae, Polydnaviruses, Polyomaviridae, Poxviridae, Sphaerolipoviridae, and Tectiviridae.

In some cases, the viral vector is obtained from a ssDNA virus of the family: Anelloviridae, Bacillariodnaviridae, Bidnaviridae, Circoviridae, Geminiviridae, Inoviridae, Microviridae, Nanoviridae, Parvoviridae, and Spiraviridae.

In some embodiments, the viral vector is obtained from a DNA virus that contains both ss and ds DNA regions. In some cases, the DNA virus is from the group pleolipoviruses. In some cases, the pleolipoviruses include Haloarcula hispanica pleomorphic virus 1, Halogeometricum pleomorphic virus 1, Halorubrum pleomorphic virus 1, Halorubrum pleomorphic virus 2, Halorubrum pleomorphic virus 3, and Halorubrum pleomorphic virus 6.

In some cases, the viral vector is obtained from a dsRNA virus of the family: Birnaviridae, Chrysoviridae, Cystoviridae, Endornaviridae, Hypoviridae, Megavirnaviridae, Partitiviridae, Picobirnaviridae, Reoviridae, Rotavirus and Totiviridae.

In some instances, the viral vector is obtained from a positive-sense ssRNA virus of the family: Alphaflexiviridae, Alphatetraviridae, Alvernaviridae, Arteriviridae, Astroviridae, Barnaviridae, Betaflexiviridae, Bromoviridae, Caliciviridae, Carmotetraviridae, Closteroviridae, Coronaviridae, Dicistroviridae, Flaviviridae, Gammaflexiviridae, Iflaviridae, Leviviridae, Luteoviridae, Marnaviridae, Mesoniviridae, Narnaviridae, Nodaviridae, Permutotetraviridae, Picornaviridae, Potyviridae, Roniviridae, Secoviridae, Togaviridae, Tombusviridae, Tymoviridae, and Virgaviridae.

In some cases, the viral vector is obtained from a negative-sense ssRNA virus of the family: Bornaviridae, Filoviridae, Paramyxoviridae, Rhabdoviridae, Nyamiviridae, Arenaviridae, Bunyaviridae, Ophioviridae, and Orthomyxoviridae.

In some instances, the viral vector is obtained from oncolytic DNA viruses that comprise capsid symmetry that is isocahedral or complex. In some cases, icosahedral oncolytic DNA viruses are naked or comprise an envelope. Exemplary families of oncolytic DNA viruses include the Adenoviridae (for example, Adenovirus, having a genome size of 36-38 kb), Herpesviridae (for example, HSV1, having a genome size of 120-200 kb) and Poxviridae (for example, Vaccinia virus and myxoma virus, having a genome size of 130-280 kb).

In some cases, the viral vector is obtained from oncolytic RNA viruses include those having icosahedral or helical capsid symmetry. In some cases, icosahedral oncolytic viruses are naked without envelope and include Reoviridae (for example, Reovirus, having a genome of 22-27 kb) and Picornaviridae (for example, Poliovirus, having a genome size of 7.2-8.4 kb). In other cases, helical oncolytic RNA viruses are enveloped and include Rhabdoviridae (for example, VSV, having genome size of 13-16 kb) and Paramyxoviridae (for example MV and NDV, having genome sizes of 16-20 kb).

Exemplary viral vectors include, but are not limited to, retroviral vectors, lentiviral vectors, adenoviral vectors, adeno-associated viral vectors, alphaviral vectors, herpes simplex virus vectors, vaccinia viral vectors, or chimeric viral vectors. In some embodiments, the viral vector is a lentiviral vector. In some embodiments, the lentiviral vector is pLKO.1 vector.

In some instances, a virus comprising one or more of the nucleic acid polymers or polypeptides described herein are generated using methods well known in the art. In some instances, the methods involve one or more transfection steps and one or more infection steps. In some instances, a cell line such as a mammalian cell line, an insect cell line, or a plant cell line is infected with a virus to produce one or more viruses. Exemplary mammalian cell lines include: 293A cell line, 293FT cell line, 293F cells, 293 H cells, CHO DG44 cells, CHO-S cells, CHO-K1 cells, Expi293F™ cells, Flp-In™ T-REx™ 293 cell line, Flp-In™-293 cell line, Flp-In™-3T3 cell line, Flp-In™-BHK cell line, Flp-In™-CHO cell line, Flp-In™-CV-1 cell line, Flp-In™-Jurkat cell line, FreeStyle™ 293-F cells, FreeStyle™ CHO-S cells, GripTite™ 293 MSR cell line, GS-CHO cell line, HepaRG™ cells, T-REx™ Jurkat cell line, Per.C6 cells, T-REx™-293 cell line, T-REx™-CHO cell line, T-REx™-HeLa cell line, 3T6, A549, A9, AtT-20, BALB/3T3, BHK-21, BHL-100, BT, Caco-2, Chang, Clone 9, Clone M-3, COS-1, COS-3, COS-7, CRFK, CV-1, D-17, Daudi, GH1, GH3, H9, HaK, HCT-15, HEp-2, HL-60, HT-1080, HT-29, HUVEC, I-10, IM-9, JEG-2, Jensen, K-562, KB, KG-1, L2, LLC-WRC 256, McCoy, MCF7, VERO, WI-38, WISH, XC, or Y-1. Exemplary insect cell lines include *Drosophila* S2 cells, Sf9 cells, Sf21 cells, High Five™ cells, or expresSF+® cells. Exemplary plant cell lines include algae cells such as for example *Phaeocystis pouchetii*.

In some embodiments, the vector comprising one or more of the nucleic acid polymer or polypeptide described herein is delivered through electroporation, chemical method, microinjection, gene gun, impalefection, hydrodynamics-based delivery, continuous infusion, or sonication. In some embodiments, the chemical method is lipofection. In some cases, the method is infection, or adsorption or transcytosis.

In some embodiments, electroporation is a technique in which an electric field is applied to cells to increase the permeability of the cell membrane, allowing for the introduction of chemicals, drugs, or DNA into the cell.

In some embodiments, chemical method is a method of transfection that uses carrier molecules to overcome the cell-membrane barrier. In some instances, the chemical method is lipofection whereby genetic material is injected into a cell using liposomes.

In some embodiments, microinjection is the injection of genetic material into animal cells, tissues or embryos via a needle.

In some embodiments, gene gun is a device that injects cells with genetic information by shooting them with elemental particle of a heavy metal coated with plasmid DNA.

In some embodiments, impalefection is a method of gene delivery using nanomaterials.

In some embodiments, hydrodynamics-based delivery is the rapid injection of a relatively large volume of solution into a blood vessel to enhance the permeability to allow for the delivery of substance into cells. In some instances, the solution contains proteins, oligo nucleotides, DNA, RNA, or small molecules.

In some embodiments, continuous infusion is the uninterrupted administration of drugs, fluids or nutrients into a blood vessel.

In some embodiments, sonication is applying sound energy to agitate particles in a sample for purposes such as but not limited to disrupting or deactivating a biological material or fragmenting molecules of DNA.

In some embodiments, the nucleic acid polymer is delivered as an injection, such as an intramuscular, intratympanic, intracochlear, intravenous or subcutaneous injection, without the need of a viral delivery method or non-viral delivery methods such as electroporation, chemical method, microinjection, gene gun, impalefection, hydrodynamics-based delivery, continuous infusion, or sonication. In some instances, the vector as described above is delivered as an injection, such as an intramuscular, intratympanic, intracochlear, intravenous or subcutaneous injection, without the need of a viral delivery method or non-viral delivery methods such as electroporation, chemical method, microinjection, gene gun, impalefection, hydrodynamics-based delivery, continuous infusion, or sonication.

In some embodiments, the nucleic acid polymer and/or the vector described above further comprises a delivery vehicle. In some instances, the delivery vehicle comprises a lipid-based nanoparticle; a cationic cell penetrating peptide (CPP); or a linear or branched cationic polymer; or a bioconjugate, such as cholesterol, bile acid, lipid, peptide, polymer, protein, or an aptamer, which is conjugated to the nucleic acid polymer or polypeptide described herein for intracellular delivery. In some instances, additional delivery vehicles comprise glycopolymer, carbohydrate polymer, or lipid polymers such as cationic lipids or cationic lipid polymers.

Diseases

Disclosed herein, in certain embodiments, include a method of treating an otic disease or condition associated with an elevated expression level of truncated TrkC or truncated TrkB. In some instances, the method comprises administering to a patient having an otic disease or condition a therapeutic amount of a pharmaceutical composition described herein. In some instances, also described herein include a method of preventing an otic disease or condition or reducing the progression of an otic disease or condition associated with an elevated expression level of truncated TrkC or truncated TrkB. In some instances, the method comprises administering to a patient having an otic disease or condition a therapeutic amount of a pharmaceutical composition described herein.

In some embodiments, the otic diseases or conditions comprise a disease or condition associated with hearing loss. In some instances, the otic disease or condition comprises nystagmus, vertigo, tinnitus, inflammation, infection and/or congestion. In some cases, the otic disease or condition comprises ototoxicity, chemotherapy induced hearing loss, excitotoxicity, sensorineural hearing loss, noise induced hearing loss, presbycusis, Meniere's Disease/Syndrome, endolymphatic hydrops, labyrinthitis, Ramsay Hunt's Syndrome, vestibular neuronitis, tinnitus, or microvascular compression syndrome.

Excitotoxicity

Excitotoxicity refers to the death or damaging of neurons and/or otic hair cells by glutamate and/or similar substances.

Glutamate is the most abundant excitatory neurotransmitter in the central nervous system. Pre-synaptic neurons release glutamate upon stimulation. It flows across the synapse, binds to receptors located on post-synaptic neurons, and activates these neurons. The glutamate receptors include the NMDA, AMPA, and kainate receptors. Glutamate transporters are tasked with removing extracellular glutamate from the synapse. In some instances, certain events (e.g. ischemia or stroke) damage the transporters. This results in excess glutamate accumulating in the synapse. Excess glutamate in synapses results in the over-activation of the glutamate receptors.

The AMPA receptor is activated by the binding of both glutamate and AMPA. Activation of certain isoforms of the AMPA receptor results in the opening of ion channels located in the plasma membrane of the neuron. When the channels open, $Na^+$ and $Ca^{2+}$ ions flow into the neuron and $K^+$ ions flow out of the neuron.

The NMDA receptor is activated by the binding of both glutamate and NMDA. Activation of the NMDA receptor, results in the opening of ion channels located in the plasma membrane of the neuron. However, these channels are blocked by $Mg^{2+}$ ions. Activation of the AMPA receptor results in the expulsion of $Mg^{2+}$ ions from the ion channels into the synapse. When the ion channels open, and the $Mg^{2+}$ ions evacuate the ion channels, $Na^+$ and $Ca^{2+}$ ions flow into the neuron, and $K^+$ ions flow out of the neuron.

Excitotoxicity occurs when the NMDA receptor and AMPA receptors are over-activated by the binding of excessive amounts of ligands, for example, abnormal amounts of glutamate. The over-activation of these receptors causes excessive opening of the ion channels under their control. This allows abnormally high levels of $Ca^{2+}$ and $Na^+$ to enter the neuron. The influx of these levels of $Ca^{2+}$ and $Na^+$ into the neuron causes the neuron to fire more often, resulting in a rapid buildup of free radicals and inflammatory compounds within the cell. The free radicals eventually damage the mitochondria, depleting the cell's energy stores. Furthermore, excess levels of $Ca^{2+}$ and $Na^+$ ions activate excess levels of enzymes including, but not limited to, phospholipases, endonucleases, and proteases. The over-activation of these enzymes results in damage to the cytoskeleton, plasma membrane, mitochondria, and DNA of the sensory neuron. In some embodiments, an auris sensory cell modulating agent is a glutamate receptor antagonist that reduces or inhibits excessive neuronal firing and/or neuronal cell death. Disclosed herein, in certain embodiments, is a pharmaceutical composition for use in the treatment of a disease of the ear characterized by the dysfunction of an NMDA receptor.

Tinnitus

As used herein, "tinnitus" refers to a disorder characterized by the perception of sound in the absence of any external stimuli. In certain instances, tinnitus occurs in one or both ears, continuously or sporadically, and is most often described as a ringing sound. It is most often used as a diagnostic symptom for other diseases. There are two types of tinnitus: objective and subjective. The former is a sound created in the body which is audible to anyone. The latter is audible only to the affected individual. Studies estimate that over 50 million Americans experience some form of tinnitus. Of those 50 million, about 12 million experience severe tinnitus.

There are several treatments for tinnitus. Lidocaine, administered by IV, reduces or eliminates the noise associated with tinnitus in about 60-80% of sufferers. Selective neurotransmitter reuptake inhibitors, such as nortriptyline, sertraline, and paroxetine, have also demonstrated efficacy against tinnitus. Benzodiazepines are also prescribed to treat tinnitus. In some embodiments, an auris sensory cell modulating agent reduces or inhibits auris sensory cell damage and/or death associated with tinnitus.

Sensorineural Hearing Loss

Sensorineural hearing loss is a type of hearing loss which results from defects (congenital and acquired) in the vestibulocochlear nerve (also known as cranial nerve VIII), or sensory cells of the inner ear. The majority of defects of the inner ear are defects of otic hair cells and sensory neurons.

Aplasia of the cochlea, chromosomal defects, and congenital cholesteatoma are examples of congenital defects which in some instances, result in sensorineural hearing loss. By way of non-limiting example, inflammatory diseases (e.g. suppurative labyrinthitis, meningitis, mumps, measles, viral syphilis, and autoimmune disorders), Meniere's Disease, exposure to ototoxic drugs (e.g. aminoglycosides, loop diuretics, antimetabolites, salicylates, and cisplatin), physical trauma, presbyacusis, and acoustic trauma (prolonged exposure to sound in excess of 90 dB) also results in acquired sensorineural hearing loss.

If the defect resulting in sensorineural hearing loss is a defect in the auditory pathways, the sensorineural hearing loss is called central hearing loss. If the defect resulting in sensorineural hearing loss is a defect in the auditory pathways, the sensorineural hearing loss is called cortical deafness. In some embodiments, an auris sensory cell modulating agent is a trophic agent (e.g., BDNF, GDNF) that promotes growth of auris sensory cells and their processes and connections and reduces or reverses sensorineural hearing loss.

Noise Induced Hearing Loss

Noise induced hearing loss (NIHL) is caused upon exposure to sounds that are too loud or loud sounds that last an extended period of time. Long or repeated or impulse exposure to sounds at or above 85 decibels in some cases cause hearing loss. Hearing loss also occurs from prolonged exposure to loud noises, such as loud music, heavy equipment or machinery, airplanes, gunfire or other human-based noises. NIHL causes damage to the hair cells and/or the auditory nerve. The hair cells are small sensory cells that convert sound energy into electrical signals that travel to the brain. In some instances, impulse sound results in immediate hearing loss that is permanent. This kind of hearing loss in some cases is accompanied by tinnitus—a ringing, buzzing, or roaring in the ears or head—which in some cases subsides over time. Hearing loss and tinnitus in some instances are experienced in one or both ears, and tinnitus continues constantly or occasionally throughout a lifetime. Continuous exposure to loud noise also damages the structure of hair cells, resulting in permanent hearing loss and tinnitus, although the process occurs more gradually than for impulse noise.

In some embodiments, an otoprotectant reverses, reduces or ameliorates NIHL. Examples of otoprotectants that treat or prevent NIHL include, but are not limited to, otoprotectants described herein.

Ototoxicity

Ototoxicity refers to hearing loss caused by a toxin. In some instances, the hearing loss is due to trauma to otic hair cells, the cochlea, and/or the cranial nerve VII. Multiple drugs are known to be ototoxic. Often ototoxicity is dose-dependent. It is permanent or reversible upon withdrawal of the drug.

Known ototoxic drugs include, but are not limited to, the aminoglycoside class of antibiotics (e.g. gentamicin, and amikacin), some members of the macrolide class of antibiotics (e.g erythromycin), some members of the glycopeptide class of antibiotics (e.g. vancomycin), salicylic acid, nicotine, some chemotherapeutic agents (e.g. actinomycin, bleomycin, cisplatin, carboplatin, oxaliplatin and vincristine), and some members of the loop diuretic family of drugs (e.g. furosemide), 6-hydroxy dopamine (6-OH DPAT), 6,7-dinitroquinoxaline-2,3-dione (DNQX) or the like.

Chemotherapeutic agents and the aminoglycoside class of antibiotics induce the production of reactive oxygen species ("ROS"). In some embodiments, ROS damages cells directly by damaging DNA, polypeptides, and/or lipids. Antioxidants prevent damage of ROS by preventing their formation or scavenging free radicals before they damage the cell. Both chemotherapeutic agents and the aminoglycoside class of antibiotics are also thought to damage the ear by binding melanin in the stria vascularis of the inner ear. In some instances, hearing loss induced by chemotherapy agents such as cisplatin, actinomycin, bleomycin, carboplatin, oxaliplatin and vincristine is referred to as chemotherapy induced hearing loss.

Salicylic acid is classified as ototoxic as it inhibits the function of the polypeptide prestin. Prestin mediates outer otic hair cell motility by controlling the exchange of chloride and carbonate across the plasma membrane of outer otic hair cells. It is only found in the outer otic hair cells, not the inner otic hair cells. Accordingly, disclosed herein is the use of controlled release auris-compositions comprising otoprotectants (e.g. antioxidants) to prevent, ameliorate or lessen ototoxic effects of chemotherapy, including but not limited to cisplatin treatment, aminoglycoside or salicylic acid administration, or other ototoxic agents.

Endolymphatic Hydrops

Endolymphatic hydrops refers to an increase in the hydraulic pressure within the endolymphatic system of the inner ear. The endolymph and perilymph are separated by thin membranes which contain multiple nerves. Fluctuation in pressure stresses the membranes and the nerves they house. If the pressure is great enough, disruptions form in these membranes. This results in a mixing of the fluids which leads to a depolarization blockade and transient loss of function. Changes in the rate of vestibular nerve firing often leads to vertigo. Further, the organ of Corti is also be affected. Distortions of the basilar membrane and the inner and outer hair cells leads to hearing loss and/or tinnitus.

Causes include metabolic disturbances, hormonal imbalances, autoimmune disease, and viral, bacterial, or fungal infections. Symptoms include hearing loss, vertigo, tinnitus, and aural fullness. Nystagmus is also present in some instances. Treatment includes systemic administration of benzodiazepine, diuretics (to decrease the fluid pressure), corticosteroids, and/or anti-bacterial, anti-viral, or anti-fungal agents.

Labyrinthitis

Labyrinthitis is an inflammation of the labyrinths of the ear which contain the vestibular system of the inner ear. Causes include bacterial, viral, and fungal infections. In some cases, it is also caused by a head injury or allergies. Symptoms of labyrinthitis include difficulty maintaining balance, dizziness, vertigo, tinnitus, and hearing loss. Recovery takes one to six weeks; however, chronic symptoms are present for years in some cases.

There are several treatments for labyrinthitis. Prochlorperazine is often prescribed as an antiemetic. Serotonin-reuptake inhibitors have been shown to stimulate new neural growth within the inner ear. Additionally, treatment with antibiotics is prescribed if the cause is a bacterial infection, and treatment with corticosteroids and antivirals is recommended if the condition is caused by a viral infection.

Meniere's Disease

Meniere's Disease is an idiopathic condition characterized by sudden attacks of vertigo, nausea and vomiting that in some instances last for 3 to 24 hours, and subside gradually. Progressive hearing loss, tinnitus and a sensation of pressure in the ears accompanies the disease through time. The cause of Meniere's disease is likely related to an imbalance of inner ear fluid homeostasis, including an increase in production or a decrease in reabsorption of inner ear fluid.

Studies of the vasopressin (VP)-mediated aquaporin 2 (AQP2) system in the inner ear suggest a role for VP in inducing endolymph production, thereby increasing pressure in the vestibular and cochlear structures. VP levels were found to be upregulated in endolymphatic hydrops (Meniere's Disease) cases, and chronic administration of VP in guinea pigs was found to induce endolymphatic hydrops. Treatment with VP antagonists, including infusion of OPC-31260 (a competitive antagonist of V2-R) into the scala tympani resulted in a marked reduction of Meniere's disease symptoms. Other VP antagonists include WAY-140288, CL-385004, tolvaptan, conivaptan, SR 121463A and VPA 985. (Sanghi et al. Eur. Heart J. (2005) 26:538-543; Palm et al. Nephrol. Dial Transplant (1999) 14:2559-2562).

Other studies suggest a role for estrogen-related receptor β/NR3B2 (ERR/Nr3b2) in regulating endolymph production, and therefore pressure in the vestibular/cochlear apparatus. Knock-out studies in mice demonstrate the role of the polypeptide product of the Nr3b2 gene in regulating endolymph fluid production. Nr3b2 expression has been localized in the endolymph-secreting strial marginal cells and vestibular dark cells of the cochlea and vestibular apparatus, respectively. Moreover, conditional knockout of the Nr3b2 gene results in deafness and diminished endolymphatic fluid volume. In some cases, treatment with antagonists to ERR/Nr3b2 assist in reducing endolymphatic volume, and thus alter pressure in the auris interna structures.

Other treatments are aimed at dealing with the immediate symptoms and prevention of recurrence. Low-sodium diets, avoidance of caffeine, alcohol, and tobacco have been advocated. Medications that temporarily relieve vertigo attacks include antihistamines (including meclizine and other antihistamines), and central nervous system agents, including barbiturates and/or benzodiazepines, including lorazepam or diazepam. Other examples of drugs that are useful in relieving symptoms include muscarinic antagonists, including scopolamine. Nausea and vomiting are relieved by suppositories containing antipsychotic agents, including the phenothiazine agent prochlorperazine.

Surgical procedures that have been used to relieve symptoms include the destruction of vestibular and/or cochlear function to relieve vertigo symptoms. These procedures aim to either reduce fluid pressure in the inner ear and/or to destroy inner ear balance function. An endolymphatic shunt procedure, which relieves fluid pressure, are placed in the inner ear to relieve symptoms of vestibular dysfunction. Other treatments include gentamicin application, which when injected into the eardrum destroys sensory hair cell function, thereby eradicating inner ear balance function. Severing of the vestibular nerve are also employed, which while preserving hearing, control vertigo. In some embodiments, an auris sensory cell modulator promotes growth of hair cells and allows a subject to regain inner ear balance function.

Meniere's Syndrome

Meniere's Syndrome, which displays similar symptoms as Meniere's disease, is attributed as a secondary affliction to another disease process, e.g. thyroid disease or inner ear inflammation due to syphilis infection. Meniere's syndrome, thus, are secondary effects to various process that interfere with normal production or resorption of endolymph, including endocrine abnormalities, electrolyte imbalance, autoimmune dysfunction, medications, infections (e.g. parasitic infections) or hyperlipidemia. Treatment of patients afflicted with Meniere's Syndrome is similar to Meniere's Disease.

Ramsay Hunt's Syndrome (Herpes Zoster Infection)

Ramsay Hunt's Syndrome is caused by a herpes zoster infection of the auditory nerve. The infection causes severe ear pain, hearing loss, vertigo, as well as blisters on the outer ear, in the ear canal, as well as on the skin of the face or neck supplied by the nerves. Facial muscles also becomes paralyzed if the facial nerves are compressed by the swelling. Hearing loss is temporary or permanent, with vertigo symptoms usually lasting from several days to weeks.

Treatment of Ramsay Hunt's syndrome includes administration of antiviral agents, including acyclovir. Other antiviral agents include famciclovir and valacyclovir. Combination of antiviral and corticosteroid therapy are also employed to ameliorate herpes zoster infection. Analgesics or narcotics are also administered to relieve the pain, and diazepam or other central nervous system agents to suppress vertigo. Capsaicin, lidocaine patches and nerve blocks are optionally used. Surgery is also performed on compressed facial nerves to relieve facial paralysis.

Microvascular Compression Syndrome

Microvascular compression syndrome (MCS), also called "vascular compression" or "neurovascular compression", is a disorder characterized by vertigo and tinnitus. It is caused by the irritation of Cranial Nerve VII by a blood vessel. Other symptoms found in subjects with MCS include, but are not limited to, severe motion intolerance, and neuralgic like "quick spins". MCS is treated with carbamazepine, TRILEPTAL®, and baclofen. In some cases, it is also surgically treated.

Vestibular Neuronitis

Vestibular neuronitis, or vestibular neuropathy, is an acute, sustained dysfunction of the peripheral vestibular system. It is theorized that vestibular neuronitis is caused by a disruption of afferent neuronal input from one or both of the vestibular apparatuses. Sources of this disruption include viral infection and acute localized ischemia of the vestibular nerve and/or labyrinth.

The most significant finding when diagnosing vestibular neuronitis is spontaneous, unidirectional, horizontal nystagmus. It is often accompanied by nausea, vomiting, and vertigo. It is, however, generally not accompanied by hearing loss or other auditory symptoms.

There are several treatments for vestibular neuronitis. H1-receptor antagonists, such as dimenhydrinate, diphenhydramine, meclizine, and promethazine, diminish vestibular stimulation and depress labyrinthine function through anticholinergic effects. Benzodiazepines, such as diazepam and lorazepam, are also used to inhibit vestibular responses due to their effects on the GABAA receptor. Anticholinergics, for example scopolamine, are also prescribed. They function by suppressing conduction in the vestibular cerebellar pathways. Finally, corticosteroids (i.e. prednisone) are prescribed to ameliorate the inflammation of the vestibular nerve and associated apparatus.

Presbycusis

Age-related hearing loss (presbycusis) is the loss of hearing that gradually occurs with ageing. In some instances, it is one of the most common conditions affecting older and elderly adults. In some cases, approximately one in three people in the United States between the ages of 65 and 74 has hearing loss, and nearly half of those older than 75 have difficulty hearing. In some cases, having trouble hearing makes it hard to understand and follow a doctor's advice, respond to warnings, and hear phones, doorbells, and smoke alarms. Furthermore, in some cases, hearing loss makes it hard to enjoy talking with family and friends, leading to feelings of isolation. In some instances, age-related hearing loss occurs in one or both ears, and sometimes affecting them equally.

In some embodiments, there are many causes of age-related hearing loss. Most commonly, hearing loss arises from changes in the inner ear as one ages, but in some instances, it also results from changes in the middle ear, or from complex changes along the nerve pathways from the ear to the brain. In additional instances, certain medical conditions and medications play a role as well. In some embodiments, presbycusis results from a gradual loss of spiral ganglion neuron afferent fibers and their synapses with hair cells (ribbon synapses), causing a disconnection between the sensory cells that detect sound and the auditory nerve that transmits this information to the auditory brain. Loss of spiral ganglion neurons and hair cells also occurs. Prior exposure to loud noise or other otic insults in some cases exacerbate this ageing process, leading to an accelerated loss of hearing. Presbycusis also involves "hidden hearing loss", an inability to detect sound against a background noise ("speech-in-noise") despite a lack of marked changes in hearing thresholds. In some cases, these more subtle decrements in hearing have been associated with a loss of spiral ganglion neuron afferent fibers and their synaptic connections with hair cells (ribbon synapses).

Anatomy of the Ear

Figure 3:
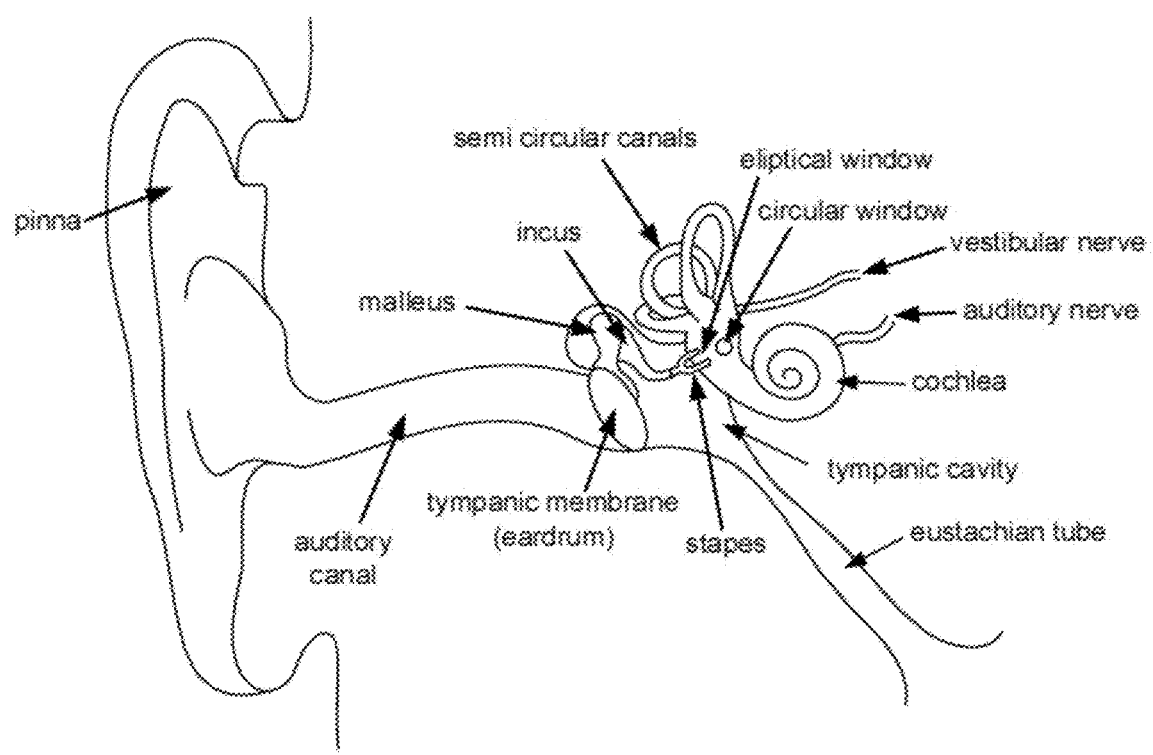
FIG. 3 shows a cartoon representation of the anatomy of an ear.

As shown in FIG. 3, the outer ear is the external portion of the organ and is composed of the pinna (auricle), the auditory canal (external auditory meatus) and the outward facing portion of the tympanic membrane, also known as the ear drum. The pinna, which is the fleshy part of the external ear that is visible on the side of the head, collects sound waves and directs them toward the auditory canal. Thus, the function of the outer ear, in part, is to collect and direct sound waves towards the tympanic membrane and the middle ear.

The middle ear is an air-filled cavity, called the tympanic cavity, behind the tympanic membrane. The tympanic membrane, also known as the ear drum, is a thin membrane that separates the external ear from the middle ear. The middle ear lies within the temporal bone, and includes within this space the three ear bones (auditory ossicles): the malleus, the incus and the stapes. The auditory ossicles are linked together via tiny ligaments, which form a bridge across the space of the tympanic cavity. The malleus, which is attached to the tympanic membrane at one end, is linked to the incus at its anterior end, which in turn is linked to the stapes. The stapes is attached to the oval window, one of two windows located within the tympanic cavity. A fibrous tissue layer, known as the annular ligament connects the stapes to the oval window. Sound waves from the outer ear first cause the tympanic membrane to vibrate. The vibration is transmitted across to the cochlea through the auditory ossicles and oval window, which transfers the motion to the fluids in the auris interna. Thus, the auditory ossicles are arranged to provide a mechanical linkage between the tympanic membrane and the oval window of the fluid-filled auris interna, where sound is transformed and transduced to the auris interna for further processing. Stiffness, rigidity or loss of movement of the auditory ossicles, tympanic membrane or oval window leads to hearing loss, e.g. otosclerosis, or rigidity of the stapes bone.

The tympanic cavity also connects to the throat via the eustachian tube. The eustachian tube provides the ability to equalize the pressure between the outside air and the middle ear cavity. The round window, a component of the auris interna but which is also accessible within the tympanic cavity, opens into the cochlea of the auris interna. The round window is covered by round window membrane, which consists of three layers: an external or mucous layer, an intermediate or fibrous layer, and an internal membrane, which communicates directly with the cochlear fluid. The round window, therefore, has direct communication with the auris interna via the internal membrane.

Movements in the oval and round window are interconnected, i.e. as the stapes bone transmits movement from the tympanic membrane to the oval window to move inward against the auris interna fluid, the round window (round window membrane) is correspondingly pushed out and away from the cochlear fluid. This movement of the round window allows movement of fluid within the cochlea, which leads in turn to movement of the cochlear inner hair cells, allowing hearing signals to be transduced. Stiffness and rigidity in round window membrane leads to hearing loss because of the lack of ability of movement in the cochlear fluid. Recent studies have focused on implanting mechanical transducers onto the round window, which bypasses the normal conductive pathway through the oval window and provides amplified input into the cochlear chamber.

Auditory signal transduction takes place in the auris interna. The fluid-filled auris interna, or inner ear, consists of two major components: the cochlear and the vestibular apparatus. The auris interna is located in part within the osseous or bony labyrinth, an intricate series of passages in the temporal bone of the skull. The vestibular apparatus is the organ of balance and consists of the three semi-circular canals and the vestibule. The three semi-circular canals are arranged relative to each other such that movement of the head along the three orthogonal planes in space is detected by the movement of the fluid and subsequent signal processing by the sensory organs of the semi-circular canals, called the crista ampullaris. The crista ampullaris contains hair cells and supporting cells, and is covered by a dome-shaped gelatinous mass called the cupula. The hairs of the hair cells are embedded in the cupula. The semi-circular canals detect dynamic equilibrium, the equilibrium of rotational or angular movements.

When the head turns rapidly, the semicircular canals move with the head, but endolymph fluid located in the membranous semi-circular canals tends to remain stationary. The endolymph fluid pushes against the cupula, which tilts to one side. As the cupula tilts, it bends some of the hairs on the hair cells of the crista ampullaris, which triggers a sensory impulse. Because each semicircular canal is located in a different plane, the corresponding crista ampullaris of each semi-circular canal responds differently to the same movement of the head. This creates a mosaic of impulses that are transmitted to the central nervous system on the vestibular branch of the vestibulocochlear nerve. The central nervous system interprets this information and initiates the appropriate responses to maintain balance. Of importance in the central nervous system is the cerebellum, which mediates the sense of balance and equilibrium.

The vestibule is the central portion of the auris interna and contains mechanoreceptors bearing hair cells that ascertain static equilibrium, or the position of the head relative to gravity. Static equilibrium plays a role when the head is motionless or moving in a straight line. The membranous labyrinth in the vestibule is divided into two sac-like structures, the utricle and the saccule. Each structure in turn contains a small structure called a macula, which is responsible for maintenance of static equilibrium. The macula consists of sensory hair cells, which are embedded in a gelatinous mass (similar to the cupula) that covers the macula. Grains of calcium carbonate, called otoliths, are embedded on the surface of the gelatinous layer.

When the head is in an upright position, the hairs are straight along the macula. When the head tilts, the gelatinous mass and otoliths tilts correspondingly, bending some of the hairs on the hair cells of the macula. This bending action initiates a signal impulse to the central nervous system, which travels via the vestibular branch of the vestibulocochlear nerve, which in turn relays motor impulses to the appropriate muscles to maintain balance.

The cochlea is the portion of the auris interna related to hearing. The cochlea is a tapered tube-like structure which is coiled into a shape resembling a snail. The inside of the cochlea is divided into three regions, which is further defined by the position of the vestibular membrane and the basilar membrane. The portion above the vestibular membrane is the scala vestibuli, which extends from the oval window to the apex of the cochlea and contains perilymph fluid, an aqueous liquid low in potassium and high in sodium content. The basilar membrane defines the scala tympani region, which extends from the apex of the cochlea to the round window and also contains perilymph. The basilar membrane contains thousands of stiff fibers, which gradually increase in length from the round window to the apex of the cochlea. The fibers of the basement membrane vibrate when activated by sound. In between the scala vestibuli and the scala tympani is the cochlear duct, which ends as a closed sac at the apex of the cochlea. The cochlear duct contains endolymph fluid, which is similar to cerebrospinal fluid and is high in potassium.

The organ of Corti, the sensory organ for hearing, is located on the basilar membrane and extends upward into the cochlear duct. The organ of Corti contains hair cells, which have hairlike projections that extend from their free surface, and contacts a gelatinous surface called the tectorial membrane. Although hair cells have no axons, they are surrounded by sensory nerve fibers that form the cochlear branch of the vestibulocochlear nerve (cranial nerve VIII).

As discussed, the oval window, also known as the elliptical window communicates with the stapes to relay sound waves that vibrate from the tympanic membrane. Vibrations transferred to the oval window increases pressure inside the fluid-filled cochlea via the perilymph and scala vestibuli/ scala tympani, which in turn causes the round window membrane to expand in response. The concerted inward pressing of the oval window/outward expansion of the round window allows for the movement of fluid within the cochlea without a change of intracochlear pressure. However, as vibrations travel through the perilymph in the scala vestibuli, they create corresponding oscillations in the vestibular membrane. These corresponding oscillations travel through the endolymph of the cochlear duct, and transfer to the basilar membrane. When the basilar membrane oscillates, or moves up and down, the organ of Corti moves along with it. The hair cell receptors in the Organ of Corti then move against the tectorial membrane, causing a mechanical deformation in the tectorial membrane. This mechanical deformation initiates the nerve impulse which travels via the vestibulocochlear nerve to the central nervous system, mechanically transmitting the sound wave received into signals that are subsequently processed by the central nervous system.

Combination Therapy

In some embodiments, a pharmaceutical composition described herein is administered in combination with an additional therapeutic agent. In some instances, the additional therapeutic agent includes but is not limited to, anti-emetic agents, antimicrobial agents, antioxidants, antiseptic agents or the like.

Anti-Emetic Agents

Anti-Emetic agents are optionally used in combination with the pharmaceutical compositions or formulations disclosed herein. Anti-emetic agents include promethazine, prochlorperazine, trimethobenzamide, and triethylperazine. Other anti-emetic agents include 5HT3 antagonists such as dolasetron, granisetron, ondansetron, tropisetron, and palonosetron; and neuroleptics such as droperidol. Further anti-emetic agents include antihistamines, such as meclizine; phenothiazines such as perphenazine, and thiethyl perazine; dopamine antagonists, including domperidone, properidol, haloperidol, chlorpromazine, promethazine, prochlorperazine, metoclopramide and combinations thereof; cannabinoids, including dronabinol, nabilone, sativex, and combinations thereof; anticholinergics, including scopolamine; and steroids, including dexamethasone; trimethobenzamine, emetrol, propofol, muscimol, and combinations thereof.

Antimicrobial Agents

Antimicrobial agents are also contemplated as useful with the pharmaceutical compositions or formulations disclosed herein. Antimicrobial agents include agents that act to inhibit or eradicate microbes, including bacteria, fungi or parasites. In some cases, specific antimicrobial agents are used to combat specific microbes. Accordingly, a skilled practitioner knows which antimicrobial agent is relevant or useful depending on the microbe identified, or the symptoms displayed. Antimicrobial agents include antibiotics, antiviral agents, antifungal agents, and antiparasitic agents.

Exemplary antibiotics include amikacin, gentamicin, kanamycin, neomycin, netilmicin, streptomycin, tobramycin, paromomycin, geldanmycin, herbimycin, loracarbef, ertapenem, doripenem, imipenem, cilastatin, meropenem, cefadroxil, cefazolin, cefalotin, cefalexin, cefaclor, cefamandole, cefoxitin, defprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole, teicoplanin, vancomycin, azithromycin, clarithromycin, dirithromycin, erythromycin, roxithromycin, troleandomycin, telithromycin, spectinomycin, aztreonam, amoxicillin, ampicillin, azlocillin, carbenicillin, cloxacillin, dicloxacillin, flucloxacillin, mezlocillin, meticillin, nafcillin, oxacillin, penicillin, piperacillin, ticarcillan, bacitracin, colistin, polymyxin B, ciprofloxacin, enoxacin, gatifloxacin, levofloxacin, lomefloxacin, moxifloxacin, norfloxacin, ofloxacin, trovfloxacin, mafenide, prontosil, sulfacetamide, sulfamethizole, sulfanimilimde, sulfsalazine, sulfsioxazole, trimethoprim, demeclocycline, doxycycline, minocycline, oxtetracycline, tetracycline, arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinuspristin/dalfopristin, rifampin, tinidazole, and combinations thereof.

Exemplary antiviral agents include acyclovir, famciclovir and valacyclovir. Other antiviral agents include abacavir, aciclovir, adfovir, amantadine, amprenavir, arbidol., atazanavir, artipla, brivudine, cidofovir, combivir, edoxudine, efavirenz, emtricitabine, enfuvirtide, entecavir, fomvirsen, fosamprenavir, foscarnet, fosfonet, ganciclovir, gardasil, ibacitabine, imunovir, idoxuridine, imiquimod, indinavir, inosine, integrase inhibitors, interferons, including interferon type III, interferon type II, interferon type I, lamivudine, lopinavir, loviride, MK-0518, maraviroc, moroxydine, nelfinavir, nevirapine, nexavir, nucleoside analogues, oseltamivir, penciclovir, peramivir, pleconaril, podophyllotoxin, protease inhibitors, reverse transcriptase inhibitors, ribavirin, rimantadine, ritonavir, saquinavir, stavudine, tenofovir, tenofovir disoproxil, tipranavir, trifluridine, trizivir, tromantadine, truvada, valganciclovir, vicriviroc, vidarabine, viramidine, zalcitabine, zanamivir, zidovudine, and combinations thereof.

Exemplary antifungal agents include amrolfine, utenafine, naftifine, terbinafine, flucytosine, fluconazole, itraconazole, ketoconazole, posaconazole, ravuconazole, voriconazole, clotrimazole, econazole, miconazole, oxiconazole, sulconazole, terconazole, tioconazole, nikkomycin Z, caspofungin, micafungin, anidulafungin, amphotericin B, liposomal nystastin, pimaricin, griseofulvin, ciclopirox olamine, haloprogin, tolnaftate, undecylenate, and combinations thereof. Exemplary antiparasitic agents include amitraz, amoscanate, avermectin, carbadox, diethylcarbamizine, dimetridazole, diminazene, ivermectin, macrofilaricide, malathion, mitaban, oxamniquine, permethrin, praziquantel, prantel pamoate, selamectin, sodium stibogluconate, thiabendazole, and combinations thereof.

Antioxidants

Antioxidants are optionally used in combination with the pharmaceutical compositions described herein. Antioxidants include agents such as those that modulate the degeneration of neurons and/or hair cells of the auris. Accordingly, some embodiments incorporate the use of antioxidants. In some embodiments, the antioxidant is vitamin C, N-acetylcysteine, vitamin E, Ebselen (2-phenyl-1, 2-benzisoselenazol-3 (2H)-one (also called PZ 51 or DR3305), L-methionine, Idebenone (2-(10-hydroxydecyl)-5,6-dimethoxy-3-methyl-cyclohexa-2,5-diene-1,4-dione). In some embodiments, antioxidants are trophic agents and promote growth of healthy cells.

Anti-Septic Agents

Anti-septic agents are optionally used in combination with the compositions described herein. Anti-septic agents are also contemplated as useful with the formulations disclosed herein. Anti-septic agents include, but are not limited to, acetic acid, boric acid, gentian violet, hydrogen peroxide, carbamide peroxide, chlorhexidine, saline, mercurochrome, povidone iodine, polyhyroxine iodine, cresylate and aluminum acetate, and mixtures thereof.

Other agents are optionally used in any composition or device described herein. In some embodiments, a monoamine oxidase inhibitor (e.g., Rasagiline, R(+)-N-propargyl-1-aminoindan) is used in any composition or device described herein. In some embodiments, an adenosine antagonist (e.g., R-N6-Phenylisopropyl adenosine, 1-2-oxothiazolidine-4-carboxylic acid (Procysteine)) is used in any composition or device described herein. Any combination of active agents and/or second therapeutic agent is compatible with the compositions described herein.

Otic Surgery and Implants

In some embodiments, the pharmaceutical formulations or compositions described herein are used in combination with (e.g., implantation, short-term use, long-term use, or removal of) implants (e.g., cochlear implants). As used herein, implants include auris-interna or auris-media medical devices, examples of which include cochlear implants, hearing sparing devices, hearing-improvement devices, short electrodes, micro-prostheses or piston-like prostheses; needles; stem cell transplants; drug delivery devices; any cell-based therapeutic; or the like. In some instances, the implants are used in conjunction with a patient experiencing hearing loss. In some instances, the hearing loss is present at birth. In some instances, the hearing loss is associated with conditions such as AIED, bacterial meningitis or the like that lead to osteoneogenesis and/or nerve damage with rapid obliteration of cochlear structures and profound hearing loss.

In some instances, an implant is an immune cell or a stem cell transplant in the ear. In some instances, an implant is a small electronic device that has an external portion placed behind the ear, and a second portion that is surgically placed under the skin that helps provide a sense of sound to a person who is profoundly deaf or severely hard-of-hearing. By way of example, such cochlear medical device implants bypass damaged portions of the ear and directly stimulate the auditory nerve. In some instances, cochlear implants are used in single sided deafness. In some instances, cochlear implants are used for deafness in both ears.

In some embodiments, administration of an auris sensory cell modulator composition or device described herein in combination with an otic intervention (e.g., an intratympanic injection, a stapedectomy, a medical device implant or a cell-based transplant) delays or prevents collateral damage to auris structures, e.g., irritation, cell damage, cell death, osteoneogeneis and/or further neuronal degeneration, caused by the external otic intervention (e.g., installation of an external device and/or cells in the ear). In some embodiments, administration of an auris sensory cell modulator composition or device described herein in combination with an implant allows for a more effective restoration of hearing loss compared to an implant alone.

In some embodiments, administration of an auris sensory cell modulator composition or device described herein reduces damage to cochlear structures caused by underlying conditions (e.g., bacterial meningitis, autoimmune ear disease (AIED)) allowing for successful cochlear device implantation. In some embodiments, administration of a composition or device described herein, in conjunction with otic surgery, medical device implantation and/or cell transplantation, reduces or prevents cell damage and/or death (e.g., auris sensory hair cell death and/or damage) associated with otic surgery, medical device implantation and/or cell transplantation.

In some embodiments, administration of an auris sensory cell modulator composition or device described herein (e.g., a composition or device comprising a growth factor) in conjunction with a cochlear implant or stem cell transplant has a trophic effect (e.g., promotes healthy growth of cells and/or healing of tissue in the area of an implant or transplant). In some embodiments, a trophic effect is desirable during otic surgery or during intratympanic injection procedures. In some embodiments, a trophic effect is desirable after installation of a medical device or after a cell transplant. In some of such embodiments, the auris sensory cell modulator compositions or devices described herein are administered via direct cochlear injection, through a cochleostomy or via deposition on the round window.

In some embodiments, administration of an anti-inflammatory or immunosuppressant composition (e.g., a composition comprising an immunosuppresant such as a corticosteroid) reduces inflammation and/or infections associated with otic surgery, implantation of a medical device or a cell transplant. In some instances, perfusion of a surgical area with an auris sensory cell modulator formulation described herein reduces or eliminates post-surgical and/or post-implantation complications (e.g., inflammation, hair cell damage, neuronal degeneration, osteoneogenesis or the like). In some instances, perfusion of a surgical area with a formulation described herein reduces post-surgery or post-implantation recuperation time. In some embodiments, a medical device is coated with a composition described herein prior to implantation in the ear.

In one aspect, the formulations described herein, and modes of administration thereof, are applicable to methods of direct perfusion of the inner ear compartments. Thus, the formulations described herein are useful in combination with otic interventions. In some embodiments, an otic intervention is an implantation procedure (e.g., implantation of a hearing device in the cochlea). In some embodiments, an otic intervention is a surgical procedure including, by way of non-limiting examples, cochleostomy, labyrinthotomy, mastoidectomy, stapedectomy, stapedotomy, endolymphatic sacculotomy, tympanostomy or the like. In some embodiments, the inner ear compartments are perfused with a formulation described herein prior to otic intervention, during otic intervention, or after otic intervention, or a combination thereof.

In some embodiments, when perfusion is carried out in combination with otic intervention, the auris sensory cell compositions are immediate release compositions. In some of such embodiments, the immediate release formulations described herein are non-thickened compositions and are substantially free of extended release components (e.g., gelling components such as polyoxyethylene-polyoxypropylene copolymers). In some of such embodiments, the compositions contain less than 5% of the extended release components (e.g., gelling components such as polyoxyethylene-polyoxypropylene triblock copolymers) by weight of the formulation. In some of such embodiments, the compositions contain less than 2% of the extended release components (e.g., gelling components such as polyoxyethylene-polyoxypropylene triblock copolymers) by weight of the formulation. In some of such embodiments, the compositions contain less than 1% of the extended release components (e.g., gelling components such as polyoxyethylene-polyoxypropylene triblock copolymers) by weight of the formulation. In some of such embodiments, a composition described herein that is used for perfusion of a surgical area contains substantially no gelling component and is an immediate release composition.

Pharmaceutical Composition/Formulations

In some embodiments, pharmaceutical compositions or formulations described herein are administered to a subject by multiple administration routes, including but not limited to, parenteral (e.g., intratympanic, intracochlear, intravenous, subcutaneous, intramuscular), oral, intranasal, buccal, topical, rectal, or transdermal administration routes. In some instances, the pharmaceutical composition describe herein is formulated for parenteral (e.g., intratympanic, intracochlear, intravenous, subcutaneous, intramuscular) administration. In other instances, the pharmaceutical composition describe herein is formulated for oral administration. In still other instances, the pharmaceutical composition describe herein is formulated for intranasal administration.

In some embodiments, a pharmaceutical composition or formulation described herein comprises between about 0.001%-about 60% of an active ingredient by weight of the composition or formulation. In some instances, a pharmaceutical composition or formulation described herein comprises between about 0.01%-about 20%, between about 0.01%-about 10%, between about 0.01%-about 7.5%, between about 0.01%-6%, between about 0.01-5%, between about 0.1-about 10%, or between about 0.1-about 6% of an active ingredient by weight of the composition or formulation.

In some embodiments, a pharmaceutical composition or formulation described herein comprises an antagonist of truncated TrkC or truncated TrkB. In some cases, a pharmaceutical composition or formulation described herein comprises between about 0.001%-about 60% of an antagonist of truncated TrkC or truncated TrkB by weight of the composition or formulation. In some instances, a pharmaceutical composition or formulation described herein comprises between about 0.01%-about 20%, between about 0.01%-about 10%, between about 0.01%-about 7.5%, between about 0.01%-6%, between about 0.01-5%, between about 0.1-about 10%, or between about 0.1-about 6% of an antagonist of truncated TrkC or truncated TrkB by weight of the composition or formulation.

In some embodiments, pharmaceutical compositions or formulation described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In some embodiments, pharmaceutical compositions or formulations described herein include a carrier or carrier materials which include any commonly used excipients in pharmaceutics and are selected on the basis of compatibility with the composition disclosed herein, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. Pharmaceutically compatible carrier materials include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., *Remington: The Science and Practice of Pharmacy*, Nineteenth Ed (Easton, Pa.: Mack Publishing Company, 1995); Hoover, John E., *Remington's*

*Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins1999).

In some embodiments, pharmaceutical compositions or formulations include dispersing agents, and/or viscosity modulating agents which include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, F108®, or F127® (poloxamer 407), which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol has a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose are also used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

In some embodiments, pharmaceutical compositions or formulations comprise a poloxamer (e.g., Pluronics F68®, F88®, F108®, or F127® (poloxamer 407)). In some instances, pharmaceutical compositions or formulations comprise between about 14% to about 21% by weight of the poloxamer. In some instances, pharmaceutical compositions or formulations comprise between about 15% to about 17% by weight of the poloxamer. In some instances, pharmaceutical compositions or formulations comprise about 14% by weight of the poloxamer. In some instances, pharmaceutical compositions or formulations comprise about 15% by weight of the poloxamer. In some instances, pharmaceutical compositions or formulations comprise about 16% by weight of the poloxamer. In some instances, pharmaceutical compositions or formulations comprise about 17% by weight of the poloxamer. In some instances, pharmaceutical compositions or formulations comprise about 18% by weight of the poloxamer. In some instances, pharmaceutical compositions or formulations comprise about 19% by weight of the poloxamer. In some instances, pharmaceutical compositions or formulations comprise about 20% by weight of the poloxamer. In some instances, pharmaceutical compositions or formulations comprise about 21% by weight of the poloxamer.

In some instances, pharmaceutical compositions or formulations comprise poloxamer 407 (F127®). In some instances, pharmaceutical compositions or formulations comprise between about 14% to about 21% by weight of poloxamer 407 (F127®). In some instances, pharmaceutical compositions or formulations comprise between about 15% to about 17% by weight of poloxamer 407 (F127®). In some instances, pharmaceutical compositions or formulations comprise about 14% by weight of poloxamer 407 (F127®). In some instances, pharmaceutical compositions or formulations comprise about 15% by weight of poloxamer 407 (F127®). In some instances, pharmaceutical compositions or formulations comprise about 16% by weight of poloxamer 407 (F127®). In some instances, pharmaceutical compositions or formulations comprise about 17% by weight of poloxamer 407 (F127®). In some instances, pharmaceutical compositions or formulations comprise about 18% by weight of poloxamer 407 (F127®). In some instances, pharmaceutical compositions or formulations comprise about 19% by weight of poloxamer 407 (F127®). In some instances, pharmaceutical compositions or formulations comprise about 20% by weight of poloxamer 407 (F127®). In some instances, pharmaceutical compositions or formulations comprise about 21% by weight of poloxamer 407 (F127®).

In some embodiments, pharmaceutical compositions or formulations include pH adjusting agents or buffering agents which include acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In some embodiments, pharmaceutical compositions or formulations also include one or more salts in an amount required to bring osmolality of the composition into an acceptable range. Such salts include those such as having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In some embodiments, pharmaceutical compositions or formulations further include diluent which are also used to stabilize compounds because they provide a more stable environment. Salts dissolved in buffered solutions (which also provide pH control or maintenance) are utilized as diluents in the art, including, but are not limited to a phosphate buffered saline solution. In certain instances, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as DiPac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

In some embodiments, pharmaceutical compositions or formulations include disintegration agents or disintegrants to facilitate the breakup or disintegration of a substance. The term "disintegrate" includes both the dissolution and dispersion of the dosage form when contacted with gastrointestinal fluid. Examples of disintegration agents include a starch, e.g., a natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

In some embodiments, pharmaceutical formulations include filling agents such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

In some embodiments, pharmaceutical compositions or formulations include flavoring agents and/or "sweeteners" such as for example, acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate) (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sylitol, sucralose, sorbitol, Swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof.

Lubricants and glidants also included in the pharmaceutical compositions or formulations described herein, for example, include those that prevent, reduce or inhibit adhesion or friction of materials. Exemplary lubricants include, e.g., stearic acid, calcium hydroxide, talc, sodium stearyl fumarate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, CabOSil®, a starch such as corn starch, silicone oil, a surfactant, and the like.

Plasticizers include compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. Plasticizers also function as dispersing agents or wetting agents.

Solubilizers include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

Stabilizers include compounds such as any antioxidation agents, buffers, acids, preservatives and the like.

Suspending agents include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Surfactants include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Additional surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. Sometimes, surfactants are included to enhance physical stability or for other purposes.

Viscosity enhancing agents include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

Wetting agents include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

Injectable Formulations

Formulations suitable for intramuscular, intratympanic, intracochlear, subcutaneous, or intravenous injection include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles include water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity is maintained, for example, by the use of a coating such as lecithin, by the maintenance of the required particle size in the case of dispersions, and by the use of surfactants. Formulations suitable for subcutaneous injection also contain additives such as preserving, wetting, emulsifying, and dispensing agents. Prevention of the growth of microorganisms is ensured by various antibacterial and antifungal agents, such as parabens, chlorobutanol, phenol, sorbic acid, and the like. It also is desirable to include isotonic agents, such as sugars, sodium chloride, and the like. Prolonged absorption of the injectable pharmaceutical form is brought about by the use of agents delaying absorption, such as aluminum monostearate and gelatin.

For intravenous injections, compounds described herein are formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art. For other parenteral injections, appropriate formulations include aqueous or nonaqueous solutions, preferably with physiologically compatible buffers or excipients. Such excipients are generally known in the art.

In some instances, parenteral injections involve bolus injection or continuous infusion. Formulations for injection is presented in unit dosage form, e.g., in ampoules or in multi-dose containers, with an added preservative. The pharmaceutical composition described herein is in a form suitable for parenteral injection as a sterile suspensions, solutions or emulsions in oily or aqueous vehicles, and contains formulatory agents such as suspending, stabilizing and/or dispersing agents. Pharmaceutical formulations for parenteral administration include aqueous solutions of the active compounds in water-soluble form. Additionally, suspensions of the active compounds are prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions contain substances which increase the viscosity of the suspension, such as sodium carboxymethyl cellulose, sorbitol, or dextran. Optionally, the suspension also contains suitable stabilizers or agents which increase the solubility of the compounds to allow for the preparation of highly concentrated solutions. Alternatively, the active ingredient is in powder form for constitution with a suitable vehicle, e.g., sterile pyrogen-free water, before use.

Oral Formulations

Pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents are added, such as the cross-linked croscarmellose sodium, polyvinylpyrrolidone, agar, or alginic acid or a salt thereof such as sodium alginate.

Dragee cores are provided with suitable coatings. For this purpose, concentrated sugar solutions are used, which optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments are added to the tablets or dragee coatings for identification or to characterize different combinations of active compound doses.

Solid dosage forms are in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder) a capsule (including both soft or hard capsules, e.g., capsules made from animal-derived gelatin or plant-derived HPMC, or "sprinkle capsules"), solid dispersion, solid solution, bioerodible dosage form, controlled release formulations, pulsatile release dosage forms, multiparticulate dosage forms, pellets, granules, or an aerosol. In other instances, the pharmaceutical formulation is in the form of a powder. In still other instances, the pharmaceutical formulation is in the form of a tablet, including but not limited to, a fast-melt tablet. Additionally, pharmaceutical formulations described herein are administered as a single capsule or in multiple capsule dosage form. In some cases, the pharmaceutical formulation is administered in two, or three, or four, capsules or tablets.

In some embodiments, the pharmaceutical solid dosage forms include a composition described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in *Remington's Pharmaceutical Sciences*, 20th Edition (2000).

In some embodiments, suitable carriers for use in the solid dosage forms include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

In some embodiments, suitable filling agents for use in the solid dosage forms include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethylcellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and the like.

Binders impart cohesiveness to solid oral dosage form formulations: for powder filled capsule formulation, they aid in plug formation that are filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose (e.g., Methocel®), hydroxypropylmethylcellulose (e.g. Hypromellose USP Pharmacoat-603, hydroxypropylmethylcellulose acetate stearate (Aqoate HS-LF and HS), hydroxyethylcellulose, hydroxypropylcellulose (e.g., Klucer), ethylcellulose (e.g., Ethocel), and microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® CL, Polyplasdone® XL-10, and Povidone® K-12), larch arabogalactan, Veegum®, polyethylene glycol, waxes, sodium alginate, and the like.

Suitable lubricants or glidants for use in the solid dosage forms include, but are not limited to, stearic acid, calcium hydroxide, talc, corn starch, sodium stearyl fumerate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms include, but are not limited to, sugars (including lactose, sucrose, and dextrose), polysaccharides (including dextrates and maltodextrin), polyols (including mannitol, xylitol, and sorbitol), cyclodextrins and the like.

Suitable wetting agents for use in the solid dosage forms include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10°), sodium oleate, sodium lauryl sulfate, magnesium stearate, sodium docusate, triacetin, vitamin E TPGS and the like.

Suitable surfactants for use in the solid dosage forms include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like.

Suitable suspending agents for use in the solid dosage forms include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol have a molecular weight of about 300 to about 6000, or about 3350 to about 4000, or about 7000 to about 5400, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Suitable antioxidants for use in the solid dosage forms include, for example, e.g., butylated hydroxytoluene (BHT), sodium ascorbate, and tocopherol.

Liquid formulation dosage forms for oral administration include aqueous suspensions selected from the group including, but not limited to, pharmaceutically acceptable aqueous oral dispersions, emulsions, solutions, elixirs, gels, and syrups. See, e.g., Singh et al., *Encyclopedia of Pharmaceutical Technology*, $2^{nd}$ Ed., pp. 754-757 (2002). In addition the liquid dosage forms include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions further include a crystalline inhibitor.

In some embodiments, the aqueous suspensions and dispersions described herein remain in a homogenous state, as defined in The USP Pharmacists' Pharmacopeia (2005 edition, chapter 905), for at least 4 hours. The homogeneity should be determined by a sampling method consistent with regard to determining homogeneity of the entire composition. In one embodiment, an aqueous suspension is re-suspended into a homogenous suspension by physical agitation lasting less than 1 minute. In another aspect, an aqueous suspension is re-suspended into a homogenous suspension by physical agitation lasting less than 45 seconds. In yet another aspect, an aqueous suspension is re-suspended into a homogenous suspension by physical agitation lasting less than 30 seconds. In still another embodiment, no agitation is necessary to maintain a homogeneous aqueous dispersion.

In another aspect, dosage forms include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Exemplary microencapsulation materials useful for delaying the release of the formulations including compounds described herein, include, but are not limited to, hydroxypropyl cellulose ethers (HPC) such as Klucel or Nisso HPC, low-substituted hydroxypropyl cellulose ethers (L-HPC), hydroxypropyl methyl cellulose ethers (HPMC) such as Seppifilm-LC, Pharmacoat®, Metolose SR, Methocel®-E, Opadry YS, PrimaFlo, Benecel MP824, and Benecel MP843, methylcellulose polymers such as Methocel®-A, hydroxypropylmethylcellulose acetate stearate Aqoat (HF-LS, HF-LG,HF-MS) and Metolose®, Ethylcelluloses (EC) and mixtures thereof such as E461, Ethocel®, Aqualon®-EC, Surelease®, Polyvinyl alcohol (PVA) such as Opadry AMB, hydroxyethylcelluloses such as Natrosol®, carboxymethylcelluloses and salts of carboxymethylcelluloses (CMC) such as Aqualon®-CMC, polyvinyl alcohol and polyethylene glycol co-polymers such as Kollicoat monoglycerides (Myverol), triglycerides (KLX), polyethylene glycols, modified food starch, acrylic polymers and mixtures of acrylic polymers with cellulose ethers such as Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, Eudragit® NE30D, and Eudragit® NE 40D, cellulose acetate phthalate, sepifilms such as mixtures of HPMC and stearic acid, cyclodextrins, and mixtures of these materials.

Plasticizers include polyethylene glycols, e.g., PEG 300, PEG 400, PEG 600, PEG 1450, PEG 3350, and PEG 800, stearic acid, propylene glycol, oleic acid, and triacetin are incorporated into the microencapsulation material. In other embodiments, the microencapsulating material useful for delaying the release of the pharmaceutical compositions is from the USP or the National Formulary (NF). In yet other embodiments, the microencapsulation material is Klucel. In still other embodiments, the microencapsulation material is methocel.

Microencapsulated compositions are formulated by methods known by one of ordinary skill in the art. Such known methods include, e.g., spray drying processes, spinning disk-solvent processes, hot melt processes, spray chilling methods, fluidized bed, electrostatic deposition, centrifugal extrusion, rotational suspension separation, polymerization at liquid-gas or solid-gas interface, pressure extrusion, or spraying solvent extraction bath. In addition to these, several chemical techniques, e.g., complex coacervation, solvent evaporation, polymer-polymer incompatibility, interfacial polymerization in liquid media, in situ polymerization, in-liquid drying, and desolvation in liquid media are also used. Furthermore, other methods such as roller compaction, extrusion/spheronization, coacervation, or nanoparticle coating are also used.

Intranasal Formulations

Intranasal formulations are known in the art and are described in, for example, U.S. Pat. Nos. 4,476,116 and 6,391,452. Formulations that include the compositions described herein, which are prepared according to the above described and other techniques well-known in the art are prepared as solutions in saline, employing benzyl alcohol or other suitable preservatives, fluorocarbons, and/or other solubilizing or dispersing agents known in the art. See, for example, Ansel, H. C. et al., Pharmaceutical Dosage Forms and Drug Delivery Systems, Sixth Ed. (1995). Preferably these compositions and formulations are prepared with suitable nontoxic pharmaceutically acceptable ingredients. These ingredients are known to those skilled in the preparation of nasal dosage forms and some of these are found in Remington: The Science and Practice of Pharmacy, 21st edition, 2005, a standard reference in the field. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents are also present. The nasal dosage form should be isotonic with nasal secretions.

For administration by inhalation described herein include aerosol, mist or powder. Pharmaceutical compositions described herein are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit is determined by providing a valve to deliver a metered amount. Capsules and cartridges of, such as, by way of example only, gelatin for use in an inhaler or insufflator are formulated containing a powder mix of the compound described herein and a suitable powder base such as lactose or starch.

Dosing and Treatment Regimens

In some embodiments, the pharmaceutical compositions described herein are administered for therapeutic applications. In some embodiments, the pharmaceutical compositions described herein are also administered as a maintenance therapy, for example for a patient in remission. In some embodiments, the pharmaceutical composition is administered once per day, twice per day, three times per day or more. In some embodiments, the pharmaceutical composition is administered daily, every day, every alternate day, five days a week, once a week, every other week, two weeks per month, three weeks per month, once a month, twice a month, three times per month, or more. In some embodiments, the pharmaceutical composition is administered for at least 1 month, 2 months, 3 months, 4 months, 5 months, 6 months, 7 months, 8 months, 9 months, 10 months, 11 months, 12 months, 18 months, 2 years, 3 years, or more.

In the case wherein the patient's status does improve, upon the doctor's discretion the administration of the compounds is given continuously; alternatively, the dose of drug being administered is temporarily reduced or temporarily suspended for a certain length of time (i.e., a "drug holiday"). The length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday is from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, are reduced, as a function of the symptoms, to a level at which the improved disease, disorder or condition is retained. In some instances, patients, however, require intermittent treatment of a pharmaceutical composition described herein on a long-term basis upon any recurrence of symptoms.

In some embodiments, the amount of a given agent that corresponds to such an amount varies depending upon factors such as the particular compound, the severity of the disease, the identity (e.g., weight) of the subject or host in need of treatment, but nevertheless is routinely determined in a manner known in the art according to the particular circumstances surrounding the case, including, e.g., the specific agent being administered, the route of administration, and the subject or host being treated. In some instances, the desired dose is conveniently presented in a single dose or as divided doses administered simultaneously (or over a short period of time) or at appropriate intervals, for example as two, three, four or more sub-doses per day.

In some embodiments, the pharmaceutical composition described herein is in unit dosage forms suitable for single administration of precise dosages. In unit dosage form, the formulation is divided into unit doses containing appropriate quantities of one or more compound. In some embodiments, the unit dosage is in the form of a package containing discrete quantities of the formulation. Non-limiting examples are packaged tablets or capsules, and powders in vials or ampoules. Aqueous suspension compositions in some instances are packaged in single-dose non-reclosable containers. Alternatively, multiple-dose reclosable containers in some instances are used, in which case it is typical to include a preservative in the composition. By way of example only, formulations for parenteral injection are presented in unit dosage form, which include, but are not limited to ampoules, or in multi-dose containers, with an added preservative.

The foregoing ranges are merely suggestive, as the number of variables in regard to an individual treatment regime is large, and considerable excursions from these recommended values are not uncommon. Such dosages are altered depending on a number of variables, not limited to the activity of the compound used, the disease or condition to be treated, the mode of administration, the requirements of the individual subject, the severity of the disease or condition being treated, and the judgment of the practitioner.

In some embodiments, toxicity and therapeutic efficacy of such therapeutic regimens are determined by standard pharmaceutical procedures in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index and it is expressed as the ratio between LD50 and ED50. Compounds exhibiting high therapeutic indices are preferred. The data obtained from cell culture assays and animal studies are used in formulating a range of dosage for use in human. The dosage of such compounds lies preferably within a range of circulating concentrations that include the ED50 with minimal toxicity. The dosage varies within this range depending upon the dosage form employed and the route of administration utilized.

According to another aspect of the invention, there is provided a method of selecting a subject for treatment, comprising determining if the subject has a disease induced by defective protein expression caused by the intron retention in gene transcripts, wherein the subject is selected for treatment upon positive confirmation; and optionally treating the subject.

Diagnostic Methods

In certain embodiments, also included are methods of stratifying an individual having an otic disease or condition for treatment with a pharmaceutical composition described herein and methods of optimizing the therapy of an individual receiving a pharmaceutical composition described herein for treatment of an otic disease or condition. In some instances, disclosed herein is a method of stratifying an individual having an otic disease or condition for treatment with a pharmaceutical composition described herein, comprising: determining the expression level of a truncated TrkC or truncated TrkB; and administering to the individual a therapeutically effective amount of the pharmaceutical composition if there is an elevated expression level of the truncated TrkC or truncated TrkB. In some instances, also disclosed herein is a method of optimizing the therapy of an individual receiving a pharmaceutical composition described herein for treatment of an otic disease or condition, comprising: determining the expression level of a truncated TrkC or truncated TrkB; and modifying, discontinuing, or continuing the treatment based on the expression level of the truncated TrkC or truncated TrkB.

Methods for determining the expression and/or activity of truncated TrkC and/or truncated TrkB are well known in the art. In some embodiments, the expression levels are measured at either nucleic acid level or protein level, and by methods such as RT-PCR, Qt-PCR, microarray, Northern blot, ELISA, radioimmunoassay (RIA), electrochemiluminescence (ECL), Western blot, multiplexing technologies, or other similar methods. In some embodiments, activities of the truncated TrkC and/or truncated TrkB are measured by methods such as co-immunoprecipitation, fluorescence spectroscopy, fluorescence resonance energy transfer (FRET), isothermal titration calorimetry (ITC), dynamic light scattering (DLS), surface plasmon resonance (SPR), or other similar methods.

In some embodiments, the expression of truncated TrkC and/or truncated TrkB is determined at the nucleic acid level. Nucleic acid-based techniques for assessing expression are well known in the art and include, for example, determining the level of biomarker mRNA in a biological sample. Many expression detection methods use isolated RNA. Any RNA isolation technique that does not select against the isolation of mRNA is utilized for the purification of RNA (see, e.g., Ausubel et al., ed. (1987-1999) Current Protocols in Molecular Biology (John Wiley & Sons, New York). Additionally, large numbers of tissue samples are readily processed using techniques well known to those of skill in the art, such as, for example, the single-step RNA isolation process disclosed in U.S. Pat. No. 4,843,155.

Thus, in some embodiments, the detection of a biomarker such as truncated TrkC or truncated TrkB is assayed at the nucleic acid level using nucleic acid probes. The term "nucleic acid probe" refers to any molecule that is capable of selectively binding to a specifically intended target nucleic acid molecule, for example, a nucleotide transcript. Probes are synthesized by one of skill in the art, or derived from appropriate biological preparations. Probes are specifically designed to be labeled, for example, with a radioactive label, a fluorescent label, an enzyme, a chemiluminescent tag, a colorimetric tag, or other labels or tags that are discussed above or that are known in the art. Examples of molecules that are utilized as probes include, but are not limited to, RNA and DNA.

For example, isolated mRNA are used in hybridization or amplification assays that include, but are not limited to, Southern or Northern analyses, polymerase chain reaction analyses and probe arrays. One method for the detection of mRNA levels involves contacting the isolated mRNA with a nucleic acid molecule (probe) that hybridize to the mRNA encoded by the gene being detected. The nucleic acid probe comprises of, for example, a full-length cDNA, or a portion thereof, such as an oligonucleotide of at least 7, 15, 30, 50, 100, 250 or 500 nucleotides in length and sufficient to specifically hybridize under stringent conditions to an mRNA or genomic DNA encoding a biomarker, biomarker described herein above. Hybridization of an mRNA with the probe indicates that the biomarker or other target protein of interest is being expressed.

In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in a gene chip array. A skilled artisan readily adapts known mRNA detection methods for use in detecting the level of mRNA encoding the biomarkers or other proteins of interest.

An alternative method for determining the level of an mRNA of interest in a sample involves the process of nucleic acid amplification, e.g., by RT-PCR (see, for example, U.S. Pat. No. 4,683,202), ligase chain reaction (Barany (1991) Proc. Natl. Acad. Sci. USA 88:189 193), self-sustained sequence replication (Guatelli et al. (1990) Proc. Natl. Acad. Sci. USA 87:1874-1878), transcriptional amplification system (Kwoh et al. (1989) Proc. Natl. Acad. Sci. USA 86:1173-1177), Q-Beta Replicase (Lizardi et al. (1988) Bio/Technology 6:1197), rolling circle replication (U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention, biomarker expression is assessed by quantitative fluorogenic RT-PCR (i.e., the TaqMan System).

Expression levels of an RNA of interest are monitored using a membrane blot (such as used in hybridization analysis such as Northern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference. The detection of expression also comprises using nucleic acid probes in solution.

In some embodiments, microarrays are used to determine expression of one or more biomarkers of truncated TrkC and/or truncated TrkB. Microarrays are particularly well suited for this purpose because of the reproducibility between different experiments. DNA microarrays provide one method for the simultaneous measurement of the expression levels of large numbers of genes. Each array consists of a reproducible pattern of capture probes attached to a solid support. Labeled RNA or DNA is hybridized to complementary probes on the array and then detected by laser scanning. Hybridization intensities for each probe on the array are determined and converted to a quantitative value representing relative gene expression levels. See, U.S. Pat. Nos. 6,040,138, 5,800,992, 6,020,135, 6,033,860, 6,344,316, and U.S. Pat. Application 20120208706. High-density oligonucleotide arrays are particularly useful for determining the gene expression profile for a large number of RNA's in a sample. Exemplary microarray chips include FoundationOne and FoundationOne Heme from Foundation Medicine, Inc; GeneChip® Human Genome U133 Plus 2.0 array from Affymetrix; and Human DiscoveryMAP® 250+ v. 2.0 from Myraid RBM.

Techniques for the synthesis of these arrays using mechanical synthesis methods are described in, e.g., U.S. Pat. No. 5,384,261. In some embodiments, an array is fabricated on a surface of virtually any shape or even a multiplicity of surfaces. In some embodiments, an array is a planar array surface. In some embodiments, arrays include peptides or nucleic acids on beads, gels, polymeric surfaces, fibers such as fiber optics, glass or any other appropriate substrate, see U.S. Pat. Nos. 5,770,358, 5,789,162, 5,708,153, 6,040,193 and 5,800,992, each of which is hereby incorporated in its entirety for all purposes. In some embodiments, arrays are packaged in such a manner as to allow for diagnostics or other manipulation of an all-inclusive device.

Any means for specifically quantifying a biomarker such as for example truncated TrkC and/or truncated TrkB in the biological sample of a candidate subject is contemplated. Thus, in some embodiments, expression level of a biomarker protein of interest in a biological sample is detected by means of a binding protein capable of interacting specifically with that biomarker protein or a biologically active variant thereof. In some embodiments, labeled antibodies, binding portions thereof, or other binding partners are used. The word "label" when used herein refers to a detectable compound or composition that is conjugated directly or indirectly to the antibody so as to generate a "labeled" antibody. In some embodiments, the label is detectable by itself (e.g., radioisotope labels or fluorescent labels) or, in the case of an enzymatic label, catalyzes chemical alteration of a substrate compound or composition that is detectable.

The antibodies for detection of a biomarker protein are either monoclonal or polyclonal in origin, or are synthetically or recombinantly produced. The amount of complexed protein, for example, the amount of biomarker protein associated with the binding protein, for example, an antibody that specifically binds to the biomarker protein, is determined using standard protein detection methodologies known to those of skill in the art. A detailed review of immunological assay design, theory and protocols are found in numerous texts in the art (see, for example, Ausubel et al., eds. (1995) Current Protocols in Molecular Biology) (Greene Publishing and Wiley-Interscience, NY)); Coligan et al., eds. (1994) Current Protocols in Immunology (John Wiley & Sons, Inc., New York, N.Y.).

The choice of marker used to label the antibodies will vary depending upon the application. However, the choice of the marker is readily determinable to one skilled in the art. These labeled antibodies are used in immunoassays as well as in histological applications to detect the presence of any biomarker of interest. The labeled antibodies are either polyclonal or monoclonal. Further, the antibodies for use in detecting a protein of interest are labeled with a radioactive atom, an enzyme, a chromophoric or fluorescent moiety, or a colorimetric tag as described elsewhere herein. The choice of tagging label also will depend on the detection limitations desired. Enzyme assays (ELISAs) typically allow detection of a colored product formed by interaction of the enzyme-tagged complex with an enzyme substrate. Radionuclides that serve as detectable labels include, for example, 1-131, 1-123, 1-125, Y-90, Re-188, Re-186, At-211, Cu-67, Bi-212, and Pd-109. Examples of enzymes that serve as detectable labels include, but are not limited to, horseradish peroxidase, alkaline phosphatase, beta-galactosidase, and glucose-6-phosphate dehydrogenase. Chromophoric moieties include, but are not limited to, fluorescein and rhodamine. The antibodies are conjugated to these labels by methods known in the art. For example, enzymes and chromophoric molecules are conjugated to the antibodies by means of coupling agents, such as dialdehydes, carbodiimides, dimaleimides, and the like. Alternatively, conjugation occurs through a ligand-receptor pair. Examples of suitable ligand-receptor pairs are biotin-avidin or biotin-streptavidin, and antibody-antigen.

In certain embodiments, expression of one or more biomarkers of interest within a biological sample, for example, a cell sample, is determined by radioimmunoassays or enzyme-linked immunoassays (ELISAs), competitive binding enzyme-linked immunoassays, dot blot (see, for example, Promega Protocols and Applications Guide, Promega Corporation (1991), Western blot (see, for example, Sambrook et al. (1989) Molecular Cloning, A Laboratory Manual, Vol. 3, Chapter 18 (Cold Spring Harbor Laboratory Press, Plainview, N.Y.), chromatography such as high performance liquid chromatography (HPLC), or other assays known in the art. Thus, the detection assays involve steps such as, but not limited to, immunoblotting, immunodiffusion, immunoelectrophoresis, or immunoprecipitation.

In some embodiments, the activities of the truncated TrkC and/or truncated TrkB are measured by methods such as co-immunoprecipitation, fluorescence spectroscopy, fluorescence resonance energy transfer (FRET), isothermal titration calorimetry (ITC), dynamic light scattering (DLS), surface plasmon resonance (SPR), or other similar methods.

Samples

In certain embodiments, one or more of the methods disclosed herein comprise a sample. In some embodiments, the sample is a cell sample or a tissue sample. In some instances, the sample is a cell sample. In additional instances, the sample is a tissue sample. In some embodiments, the sample for use with the methods described herein is obtained from cells or tissues of an animal. In some instances, the animal is a human, a non-human primate, or a rodent.

In some embodiments, the cell or tissue sample comprises neurons or otic cells such as otic hair cells, tectorial cells, Hensen & Claudius cells, pillar cells, or phalangeal cells. In some instances, neurons comprise sensory neurons, interneurons, or motor neurons. In some cases, the sample comprises sensory neurons, interneurons, or motor neurons. In some instances, the sample is a sensory neuron. In some embodiments, the sample comprises otic hair cells, tectorial cells, Hensen & Claudius cells, pillar cells, or phalangeal cells. In some embodiments, the sample is an otic hair cell.

Kits/Article of Manufacture

Disclosed herein, in certain embodiments, are kits and articles of manufacture for use with one or more methods described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

For example, the container(s) include one or more of the pharmaceutical compositions described herein comprising an antagonist of a truncated TrkC or truncated TrkB isoform and an excipient and/or delivery vehicle. Such kits optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions containing a compound provided herein formulated in a compatible pharmaceutical carrier are also prepared, placed in an appropriate container, and labeled for treatment of an indicated condition.

Certain Terminology

Unless defined otherwise, all technical and scientific terms used herein have the same meaning as is commonly understood by one of skill in the art to which the claimed subject matter belongs. It is to be understood that the general description and the detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. Hence "about 5 µL" means "about 5 µL" and also "5 µL." Generally, the term "about" includes an amount that would be expected to be within experimental error.

The section headings used herein are for organizational purposes only and are not to be construed as limiting the subject matter described.

As used herein, the terms "individual(s)", "subject(s)" and "patient(s)" mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly or a hospice worker).

EXAMPLES

These examples are provided for illustrative purposes only and not to limit the scope of the claims provided herein.

Example 1

Delivery of Adenovirus and Lentivirus Via the Round Window Membrane

Adenovirus and Lentivirus Constructs and Production

For lentivirus, a short hairpin RNA (shRNA) specifically targeting a unique 3' sequence of the TrkC T1 mRNA (GGACAATAGAGATCATCTAGT; SEQ ID NO: 1) was cloned in the Lentiviral piLenti-shRNA-GFP lenti expression vector. Lenti vectors were packaged in HEK293 cells and active particles were collected. For adenovirus the same short hairpin RNA (shRNA) specifically targeting a unique 3' sequence of the TrkC T1 mRNA was cloned into the Adenoviral—Type 5 (dE1/E3) adeno expression vector. Adeno vectors were packaged in HEK293 cells and active particles were purified by CsCl column, twice.

Adenovirus and Lentivirus in Poloxamer 407

Poloxamer 407 gel at 32% was prepared using the cold method. In brief, a 32% w/w stock solution of poloxamer 407 was prepared by slowly adding it to a cold buffer solution (10 mM PBS, pH 7.4). Sterilization was achieved by filtration. Adenovirus particles in PBS containing 5% glycerol and lentiviral particles in Dulbecco's modified Eagle's medium (DMEM) containing 10% fetal bovine serum were mixed in a 1:1 ratio with 32% poloxamer 407 to yield a solution of virus particles in 16% poloxamer 407.

Pharmacokinetics

Female rats (Charles River) weighing 200-300 g of approximately 12-16 weeks of age served as subjects (N=4 per group). Prior to any procedures, animals were anesthetized using a combination of xylazine (10 mg/kg) and ketamine (90 mg/kg) for up to an hour via the intraperitoneal route. If needed, an intraoperative booster was administered intraperitoneal representing one-tenth of the original dose.

Intratympanic Injection—

Each animal was positioned so that the head was tilted at an angle to favor injection towards the round window niche. Briefly, under visualization with a surgical microscope, 20 µL of the formulation was injected using a 25G (Gauge) 1.5 inch needle through the superior posterior quadrant of the tympanic membrane into Round Window (RW) area. Formulations were delivered using an electric perfusion pump at the rate of 2 µL/sec. The formulation dosed on the round window membrane was maintained for 30 minutes by placing the animal in a recumbent position. During the procedure and until recovery, animals were placed on a temperature controlled (40° C.) heating pad until consciousness was regained at which time they were returned to their cages.

Perilymph Sampling Procedure—

The skin behind the ear of anesthetized rats was shaved and disinfected with povidone-iodine. An incision was then made behind the ear, and muscles were carefully retracted from over the bulla. A hole was made through the bulla using a small rongeur so that the middle ear was exposed and accessed. The cochlea and the round window membrane were visualized under a surgical microscope. The basal turn of the bulla was cleaned by using small pieces of cotton ball and absorbent paper tips. A unique microhole was hand drilled through the bony shell of the cochlea (cochlear capsule) adjacent to the round window. Perilymph (about 2 µL) was then collected using a microcapillary tube inserted into the cochlear scala tympani. Perilymph samples were added to DNAase-free microcentrifuge tubes containing 18 µL of sterile RNAase/DNAase-free water and stored at −80° C. until analysis.

Cochlear Epithelium Collection—

Following the collection of perilymph, animals were euthanized by intra-cardiac injection with 0.5 mL of anesthetic cocktail consisting of xylazine (10 mg/kg) and ketamine (90 mg/kg). Animals were then immediately decapitated and the middle ear was removed and opened further to completely expose the cochlea. The bony cochlear tissue was then rinsed twice with 5 mL of sterile PBS then blotted dry. Using fine forceps, the bony cochlear capsule was chipped away and the soft cochlear tissue consisting of the cochlear epithelium, spiral ganglion neurons, and stria vascularis was removed and placed into a sterile DNAase-free microcentrifuge tube containing 200 µl of RNAlater solution and stored at −80° C. until analysis.

Detection of Adenovirus in Perilymph and Cochlea Tissue

Detection of adenovirus in perilymph and cochlea tissue samples was determined by quantitative PCR (qPCR) of DNA for the adenovirus-specific hexon protein.

Perilymph—

2 µl of perilymph was added to 18 µl of RNase/DNase-free water.

Adenoviral DNA from the sample was prepared according to the kit protocol (Clontech Adeno-X qPCR Titration Kit 632252) as follows: after addition of 130 µl PBS, 5 µl of DNase 1 was added and samples were incubated at 37° C. for 30 min. Carrier RNA in 600 µl of lysis buffer RAV1 and 20 µl of Proteinase K was added was added to each tube followed by thorough vortex mixing. The samples were heated at 70° C. for 5 min. 600 µl of ethanol was added with thorough vortexing and then 700 µl was transferred to a NucleoSpin virus column in a collection tube and centrifuged at 8000 g for 1 min. The remaining 650 µl of the sample was added to the same NucleoSpin filter, followed by centrifugation at 8000 g for 1 min. The flow-through was discarded and 500 µl of RAW buffer was added followed by centrifugation at 8000 g for 1 min. The flow-through was discarded and 600 µl of RAV3 buffer was added followed by centrifugation at 8000 g for 1 min. The filter was placed in a new collection tube and 200 µl of RAV3 buffer added followed by centrifugation at 11000 g for 5 min. The filter was placed into a new tube and 30 µl of RNase/DNase-free water (pre-heated to 70° C.) added with incubation at room temperature for 5 min. After centrifugation at 11000 g for 1 min, the DNA samples were stored at 4 or −20° C.

Cochlea— individual cochlea stored in RNAlater (Sigma-Aldrich) were placed into tubes containing 200 µl PBS and flash frozen. Samples were homogenized at 5 m/sec for a cycle of 30 sec on and 30 sec off with 4 cycles in total. Adenoviral DNA from the sample was prepared according to the kit protocol (Clontech Adeno-X qPCR Titration Kit 632252) as follows: 150 µl of the homogenate was placed in a tube and 5 µl of DNase 1 was added and samples were incubated at 37° C. for 30 min. Carrier RNA in 600 µl of lysis buffer RAV1 and 20 µl of Proteinase K was added was added to each tube followed by thorough vortex mixing. The samples were heated at 70° C. for 5 min. 600 µl of ethanol was added with thorough vortexing and then 700 µl was transferred to a NucleoSpin virus column in a collection tube and centrifuged at 8000 g for 1 min. The remaining 650 µl of the sample was added to the same NucleoSpin filter, followed by centrifugation at 8000 g for 1 min. The flow-through was discarded and 500 µl of RAW buffer was added followed by centrifugation at 8000 g for 1 min. The flow-through was discarded and 600 µl of RAV3 buffer was added followed by centrifugation at 8000 g for 1 min. The filter was placed in a new collection tube and 200 µl of RAV3 buffer added followed by centrifugation at 11000 g for 5 min. The filter was placed into a new tube and 30 µl of RNase/DNase-free water (pre-heated to 70° C.) added with incubation at room temperature for 5 min. After centrifugation at 11000 g for 1 min, the DNA samples were stored at 4 or −20° C.

qPCR:

2 µl samples of DNA from perilymph or cochlea tissue were combined with 18 µl of master mix containing 10 µM adeno-X forward primer, 10 µM adeno-X reverse primer, ROX reference dye LMP and SYBR Advantage qPCR premix according to the kit protocol (Clontech Adeno-X qPCR Titration Kit 632252). qPCR was conducted using a ThermoSci QuantiStudio 3 qPCR Machine A28137 according to the kit protocol. Samples were run in quadruplicate Detection of Lentivirus in Perilymph and Cochlea Tissue Detection of lentivirus in perilymph and cochlea tissue samples was determined by quantitative PCR (qPCR) of DNA for a conserved region of the HIV-1 genome adjacent to the packaging signal.

Perilymph—

2 µl of perilymph was added to 18 µl of RNase/DNase-free water. Lentiviral DNA from the sample was prepared according to the kit protocol (Clontech *Lenti*-X qPCR Titration Kit 631235) as follows: carrier RNA in 600 µl of lysis buffer RAV1 and 20 µl of Proteinase K was added was added to each tube followed by thorough vortex mixing. The samples were heated at 70° C. for 5 min. 600 µl of ethanol was added with thorough vortexing and then 700 µl was transferred to a NucleoSpin virus column in a collection tube and centrifuged at 8000 g for 1 min. The remaining 650 µl of the sample was added to the same NucleoSpin filter, followed by centrifugation at 8000 g for 1 min. The flow-through was discarded and 500 µl of RAW buffer was added followed by centrifugation at 8000 g for 1 min. The flow-through was discarded and 600 µl of RAV3 buffer was added followed by centrifugation at 8000 g for 1 min. The filter was placed in a new collection tube and 200 µl of RAV3 buffer added followed by centrifugation at 11000 g for 5 min. The filter was placed into a new tube and 30 µl of RNase/DNase-free water (pre-heated to 70° C.) added with incubation at room temperature for 5 min. After centrifugation at 11000 g for 1 min, the DNA samples were stored at 4 or −20° C.

Cochlea— individual cochlea stored in RNAlater (Sigma-Aldrich) were placed into tubes containing 200 µl PBS and flash frozen. Samples were homogenized at 5 m/sec for a cycle of 30 sec on and 30 sec off with 4 cycles in total. Lentiviral DNA from the sample was prepared according to the kit protocol (Clontech *Lenti*-X qPCR Titration Kit 631235) as follows: 150 µl of the homogenate was placed in a tube. Carrier RNA in 600 µl of lysis buffer RAV1 and 20 µl of Proteinase K was added was added to each tube followed by thorough vortex mixing. The samples were heated at 70° C. for 5 min. 600 µl of ethanol was added with thorough vortexing and then 700 µl was transferred to a NucleoSpin virus column in a collection tube and centrifuged at 8000 g for 1 min. The remaining 650 µl of the sample was added to the same NucleoSpin filter, followed by centrifugation at 8000 g for 1 min. The flow-through was discarded and 500 µl of RAW buffer was added followed by centrifugation at 8000 g for 1 min. The flow-through was discarded and 600 µl of RAV3 buffer was added followed by centrifugation at 8000 g for 1 min. The filter was placed in a new collection tube and 200 µl of RAV3 buffer added followed by centrifugation at 11000 g for 5 min. The filter was placed into a new tube and 30 µl of RNase/DNase-free water (pre-heated to 70° C.) added with incubation at room temperature for 5 min. After centrifugation at 11000 g for 1 min, the DNA samples were stored at 4 or −20° C.

qPCR:

2 µl samples of DNA from perilymph or cochlea tissue were combined with 18 µl of master mix containing 10 µM lenti-X forward primer, 10 µM lenti-X reverse primer, ROX reference dye and SYBR Advantage qPCR in Quant-X buffer premix according to the kit protocol (Clontech Lenti-X qPCR Titration Kit 631235). qPCR was conducted using a ThermoSci QuantiStudio 3 qPCR Machine A28137 according to the kit protocol. Samples were run in quadruplicate.

Figure 4A:
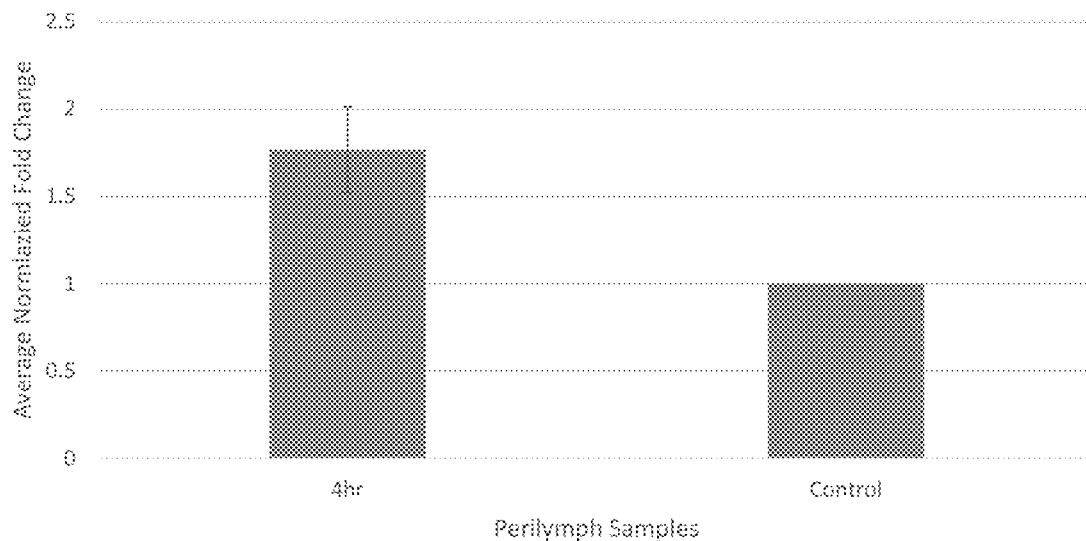
FIG. 4A and FIG. 4B illustrate the level of adenovirus that is detected in perilymph and cochlea following round window membrane administration in the rat.
Figure 4B:
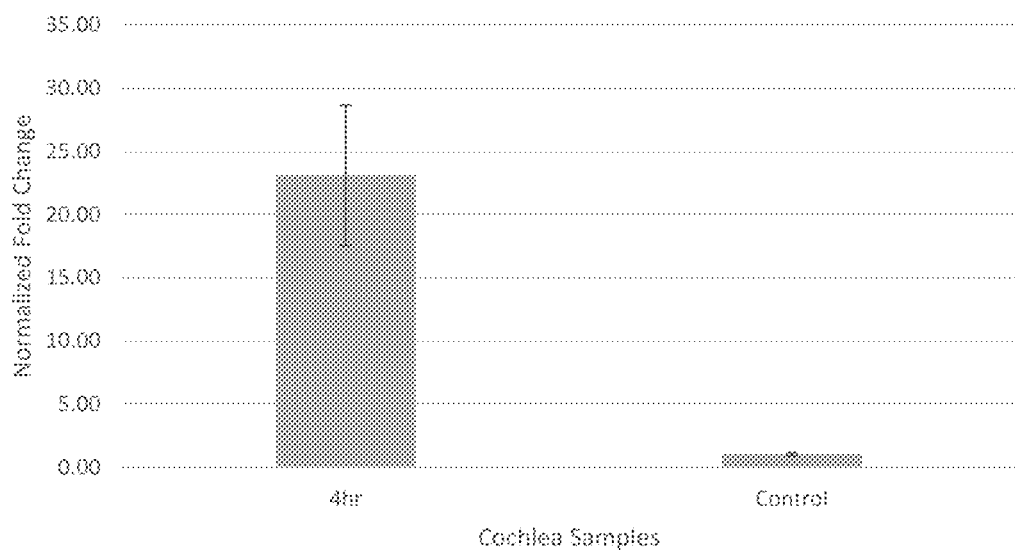
Figure 5A:
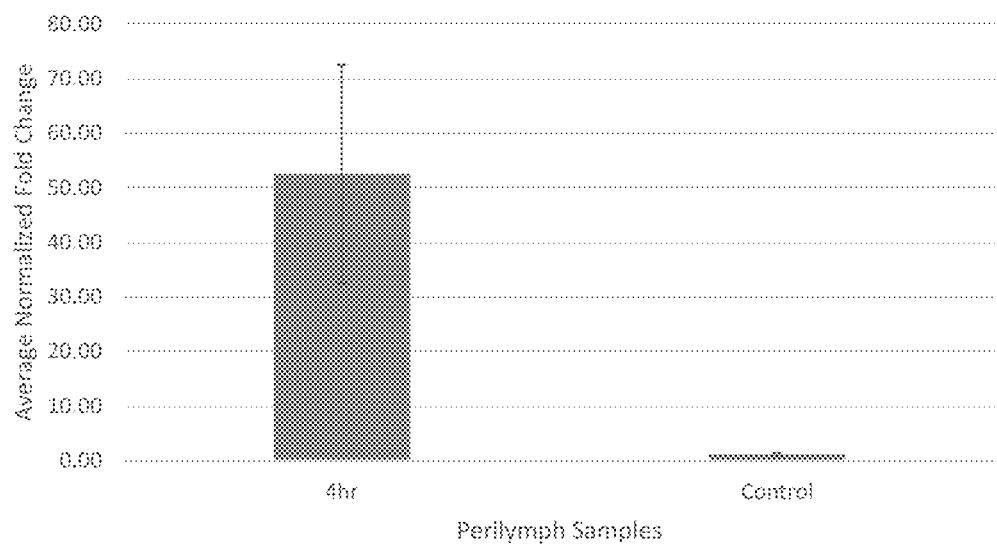
FIG. 5A and FIG. 5B illustrate the level of lentivirus that is detected in perilymph and cochlea following round window membrane administration in the rat.
Figure 5B:
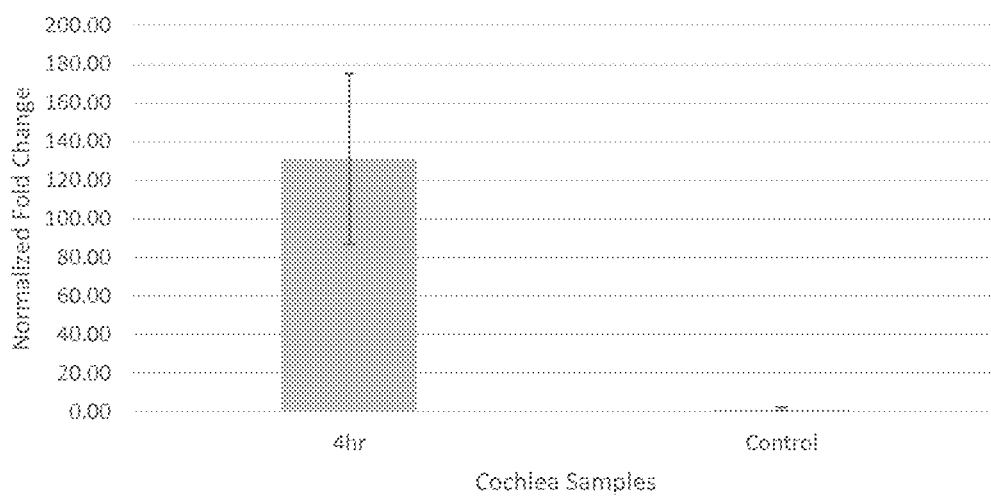

Following round window membrane administration of both adenovirus and lentivirus containing shRNA for TrkC-T1 formulated in poloxamer 407, virus was detected at 4 hours in the perilymph and in the cochlea tissue (FIG. 4 and FIG. 5). For both viruses, substantial levels of virus were detected in the target tissue (cochlea) at 4 hours (adenovirus 20-fold over control; lentivirus 130-fold over control). For both viruses, the levels of viruses were further detected at 24 hours but at lower levels relative to the levels observed at 4 hours.

Example 2

Knock-Down of TrkC.T1 in Rat Cochlea Explants by Viral Delivery of shRNA

Adenovirus and Lentivirus Constructs and Production

For lentivirus, a short hairpin RNA (shRNA) specifically targeting a unique 3' sequence of the TrkC T1 mRNA (GGACAATAGAGATCATCTAGT; SEQ ID NO: 1) was cloned in the Lentiviral piLenti-shRNA-GFP lenti expression vector. Lenti vectors were packaged in HEK293 cells and active particles were collected. For adenovirus the same short hairpin RNA (shRNA) specifically targeting a unique 3' sequence of the TrkC T1 mRNA was cloned into the Adenoviral—Type 5 (dE1/E3) adeno expression vector. Adeno vectors were packaged in HEK293 cells and active particles were purified by CsCl column, twice.

Cochlea Explant/Viral Infection

Postnatal Sprague Dawley rats (P2-4) of both sexes were anesthetized with isoflurane and decapitated. Temporal bones were removed and transferred to a cell culture dish with ice-cold $Ca^{2+}/Mg^{2+}$-containing phosphate-buffered saline (PBS; Invitrogen). Under microscopic visualization, the cochlear capsule was carefully removed from the temporal bone using forceps and transferred to a new cell culture dish containing ice-cold PBS. The cochlea was then dissected from the cochlear capsule using fine forceps. The stria vascularis was removed from the cochlear tissue and discarded. The remaining cochlea was then placed in 1 mL of culture media (Dulbecco's modified Eagle's medium [high glucose, glutamax, 25 mM HEPES] with 10% fetal bovine serum, 1% N2 supplement, 10 units/ml penicillin and 0.1 mg/ml streptomycin) in a 24-well plate. Up to 3 cochleae were placed in one well. Adenovirus or lentivirus was then added directly to the cell culture the same day. The cultures were incubated at 37° C. for 3 days before being processed.

Detection of TrkC-T1 RNA in Cochlea Explants Using qPCR

Following incubation with virus, each cochlea explant was placed in a homogenizing tube with 200 µl lysis solution containing DNase I (Life Technologies Gene Expression Cells-to-Ct Kit 4399002). Samples were flash-frozen and homogenized at 5 m/sec for a cycle of 30 sec on and 30 sec off, 4 cycles in total. Reverse transcription was achieved in PCR strip tubes with 10 µl of cochlea RNA sample and 40 µl of master mix containing 25 µl RT buffer, 2.5 µl RT enzyme mix and 12.5 µl PCR grade water (Life Technologies Gene Expression Cells-to-Ct Kit 4399002). After mixing, the samples were subjected to thermocycling to generate cDNA as follows: 37° C. for 60 min followed by 95° C. for 5 min, then 4° C. hold. To prepare samples for qPCR, 10 µl of SYBER Advantage PCR mix, 0.4 µl of LMP ROX reference dye, 0.4 µl of forward rat TrkC-T1 primer and 0.4 µl of reverse rat TrkC-T1 primer and 6.8 µl of PCR grade water was added to each well in a 96-well qPCR plate (Applied Biosystems MicroAmp Optical 96 well Plates 4306737) and 2 µl of sample cDNA added and the plate tapped to bring contents to the bottom of each well and sealed with adhesive film (Applied Biosystems MicroAmp Optical Adhesive Film 4311971). The same mix but replacing the TrkC-T1 primers with SYBER actin primers (Life Technologies #4402982) was run to determine the housekeeping gene β-actin in each cDNA sample. Each sample was run in quadruplicate. For qPCR the plate was run in a Quantstudio3 (ThermoFisher) with the following program: 50° C. for 2 min, then 95° C. for 10 min, then 95° C. for 150 sec, then 60° C. for 1 min. The last two steps were repeated 40 times. ddCT equations were used to determine fold change of TrkC-T1 RNA from the tissue relative to untreated samples using β-actin as the reference gene. The TrkC-T1 primers were as follows: rat TrkC T1 F 5' GTCCAGAGTGGGGATGTGTC 3' (SEQ ID NO: 124); Rat TrkC T1 R 5' CCATGGTTAAGAGGCTTGGA 3' (SEQ ID NO: 125).

Figure 6:
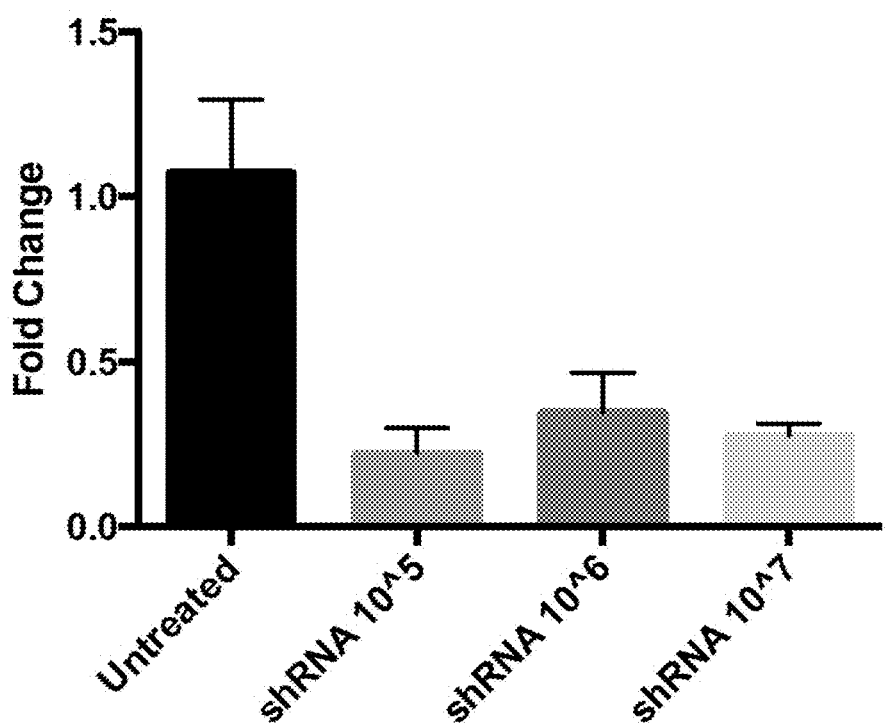
FIG. 6 shows reduced expression of TrkC-T1 in cochlea explants following exposure to lentivirus containing shRNA for rat TrkC-T1. TrkC-T1 mRNA was quantified with qPCR and the fold change calculated by the ddCT method.
Figure 7:
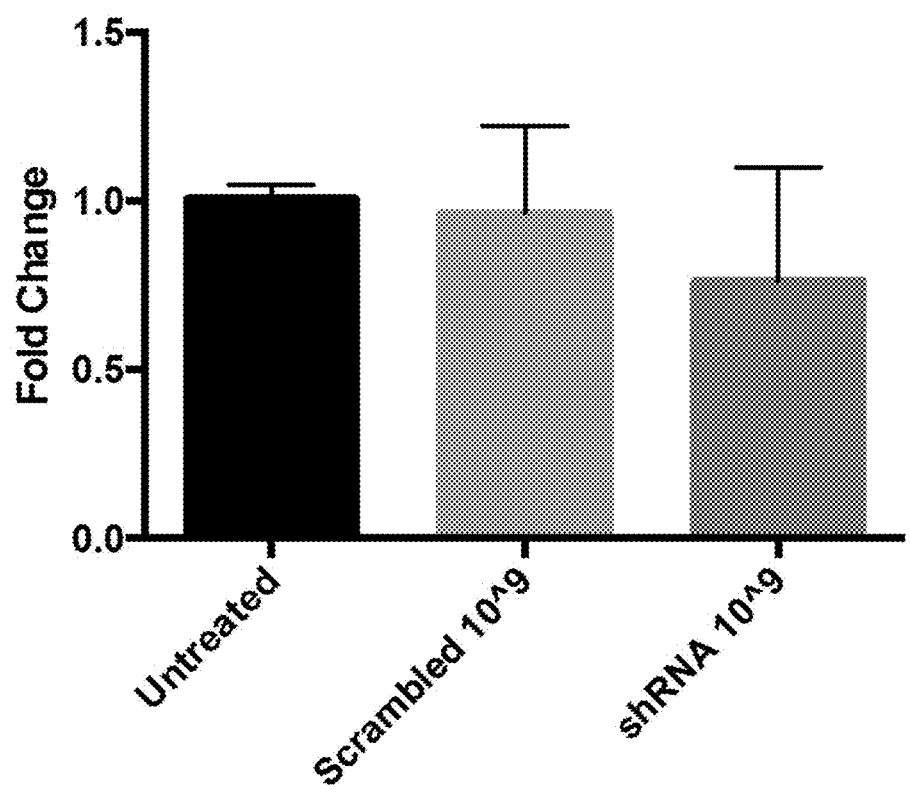
FIG. 7 shows reduced expression of TrkC-T1 in cochlea explants following exposure to adenovirus containing shRNA for rat TrkC-T1. TrkC-T1 mRNA was quantified with qPCR and the fold change calculated by the ddCT method.

Exposure of rat cochlea explants to lentivirus containing shRNA for rat TrkC-T1 resulted in a 60-80% reduction of TrkC-T1 mRNA in the tissue over the range of virus concentrations used ($10^5$-$10^7$ infectious units; FIG. 6). For the adenoviral construct, an approximately 30% reduction of TrkC-T1 mRNA in the tissue was observed at the virus concentration used ($10^9$ infectious units; FIG. 7). Adenovirus containing a scrambled shRNA sequence was used as a control and resulted in no reduction in TrkC-T1 mRNA in the tissue ($10^9$ infectious units; FIG. 7).

Example 3

Effect of TrkC.T1 Knock-Down on Cochlea Inner Hair Cell Ribbon Synapses in Mice

TrkC.T1 knockout mice:

Mice with deletion of TrkC.T1 were generated as described by Bai et al (Invest Ophthalmol Vis Sci 51:6639-6651, 2010). For these experiments, heterozygous (+/−) mice were used that have a reduction, but not complete knock-out of TrkC.T1 to mimic the therapeutic paradigm whereby an TrkC.T1 antagonist would reduce, but not eliminate TrkC.T1 function.

Analytical Method:

Assessment of cochlear inner hair cell synaptic puncta in 6-month-old TrkC.T1 heterozygous (+/−) and wild type C57BL/6 mice.

Tissue Collection and Preparation:

Approximately six-month old wild type, TrkC.T1 heterozygous (+/−) mice were deeply anesthetized and then cardiac perfused with saline then 4% PFA to rapidly fix all tissues. Fixed animals were then decapitated and the heads were placed into 4% PFA for at least 24 hours. Fixed heads were then rinsed in PBS and either stored at 4° C. or immediately dissected further. To isolate the cochleae, the heads were bisected midsagitally and both halves of the brain were removed to expose the temporal bones. Extra cranial tissue was removed from the temporal bones to expose the middle ear bulla, which were then opened to reveal the cochleae. One isolated cochlea from each animal was then incubated in 10% EDTA for 48 hours at room temperature to decalcify the bony structures. The decalcified cochlear bone was then peeled away to expose the soft tissues of the cochlear duct.

Immunohistochemistry:

Decalcified cochlear ducts were permeabilized in 0.5% PBS-Triton (PBST) for approximately 6 hours. Permeabilized tissues were then incubated in mouse anti-CtBP2 IgG1 (pre-synaptic marker; 1:200, BD Biosciences) and one or more of the following antibodies in PBST with 10% normal goat serum (Sigma) overnight at 4° C. with rotation: mouse anti-GluR2 IgG2a (post-synaptic marker; 1:500, Millipore), anti-β Tubulin III (neuronal marker; 1:1000, Sigma), or rabbit anti-Myosin VIIa (hair cell marker; 1:1000, Proteus Biosciences). Samples were then rinsed 3× for 15 minutes in PBST then incubated in one or more of the following isotype and species-specific secondary antibodies (1:1000, Life Technologies) in 10% normal goat serum in PBST for 2 hours: Alexa Fluor-488 anti-mouse IgG1, Alexa Fluor-546 anti-mouse IgG2a, Alexa Fluor-633 anti-rabbit IgG, or Alexa Fluor-546 anti-rabbit IgG. Cochlear samples were then rinsed twice in PBST, then incubated in the nuclear label DAPI in PBS (1:3000, Thermo Scientific) for at least 10 minutes before being further dissected and flat mounted onto microscope slides and coverslipped in Fluormount-G (SouthernBiotech) mounting medium.

Quantification:

A Zeiss LSM880 laser scanning confocal microscope with a 63× objective was used to image each cochlea at regions corresponding to the position at 25%, 50% and 75% of the total length of the cochlea from the base (basal, middle and apical regions, respectively). Z-stack images were obtained from the basilar membrane to the lumenal surface of the hair cells at 0.35 µm steps. From each image, a region consisting of 6 consecutive inner hair cells was identified and the number of pre-synaptic CtBP2-positive puncta within that XYZ plane was counted, this number was then divided by 6 to obtain the average number of puncta per inner hair cell per region, and these numbers were then averaged for each genotype (wild type and heterozygous).

Figure 8:
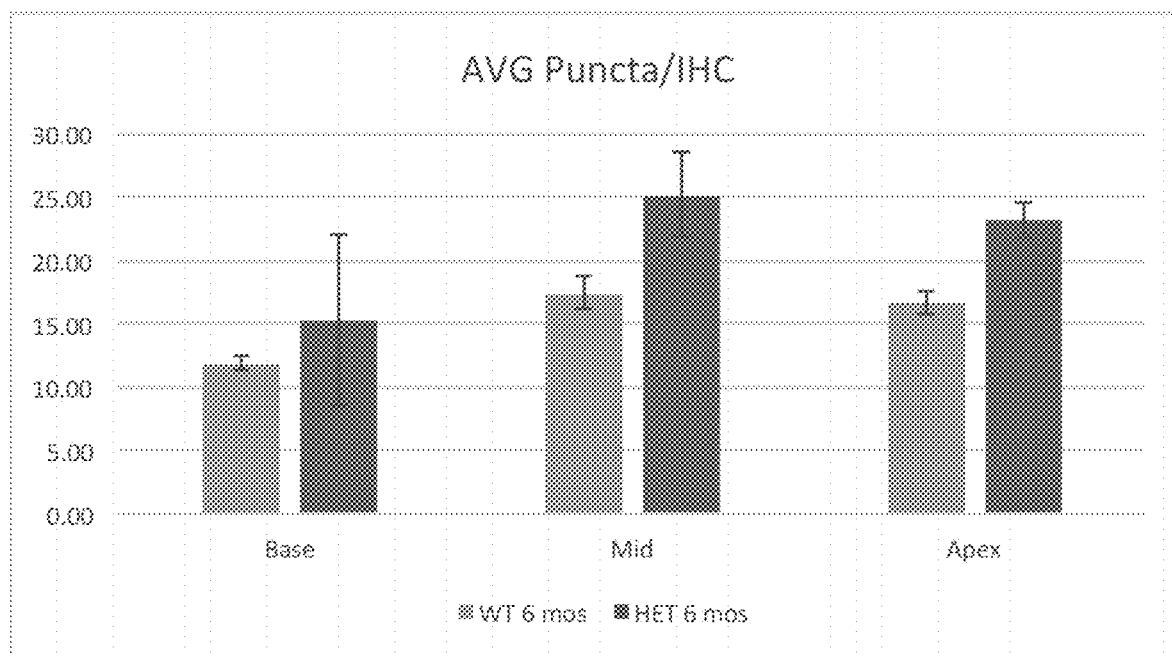
FIG. 8 shows knock-down of TrkC.T1 in heterozygous mice resulting in increased numbers of inner hair cell ribbon synapses at 6 months of age.

C57BL/6 mice are known to develop age-related hearing loss that involves reduced numbers of ribbon synapses on inner hair cells of the cochlea that is apparent by 6 months of age. Knock-down of TrkC.T1 in the heterozygous (HET) mice resulted in a larger number of inner hair cell ribbon synapses (puncta/IHC) at all levels of the cochlea (base, mid and apex) compared with wild-type (WT) controls (FIG. 8). These data suggest that TrkC.T1 knock-down is associated with preservation of inner hair cell ribbon synapses in the face of age-related decrements and is evidence of an improvement in auditory function.

Example 4

Development of Selective Inhibitors of TrkC.T1

A short hairpin RNA (shRNA) specifically targeting a unique 3' sequence of the TrkC.T1 mRNA is designed. The TrkC.T1-targeting shRNA sequence or a scrambled control are cloned into a pLKO.1 lentiviral shRNA-expression vector. pLKO.1$^{scrambled}$ and pLKO.1$^{TrkC-T1}$ lentivirus are purified and tested by infection of HEK293-TrkC.T1 or HEK293-TrkC-FL (cells transfected with TrkC.T1 or TrkC-FL cDNAs). Infection with PLKO.1$^{TrkC.T1}$ reduces TrkC.T1 mRNA without affecting TrkC-FL mRNA, whereas infection with control virus PLKO.1$^{Scrambled}$ has no effect on either TrkC.T1 or TrkC-FL mRNA. The data is verified by studying protein expression in lysates of the same cells. In multiple experiments TrkC.T1 protein expression in culture is reduced by ~80% to 97%. To assess whether reduction of TrkC.T1 has a biological impact, production of TNF-α is used as a functional endpoint for TrkC.T1 activity.

Example 5

In Vivo Testing of Intratympanic Injection of Auris Sensory Cell with a Pharmaceutical Composition Described Herein in a Guinea Pig A cohort of 21 guinea pigs (Charles River, females weighing 200-300 g) is intratympanically injected with 50 μL of a pharmaceutical formulation described herein, containing 0 to 50% antagonist of truncated TrkC or truncated TrkB. The elimination time course for each formulation is determined. A faster elimination time course of a formulation indicates lower mean dissolution time (MDT). Thus the injection volume and the concentration of an antagonist in a formulation are tested to determine optimal parameters for preclinical and clinical studies.

Example 6

Clinical Trial of an Antagonist of Truncated TrkC or Truncated TrkB as a Treatment for Tinnitus
   Active Ingredient: an antagonist of truncated TrkC or truncated TrkB
   Dosage: 10 ng delivered in 10 μL of a thermoreversible gel. Release of an antagonist of truncated TrkC or truncated TrkB is controlled release and occurs over thirty (30) days.
   Route of Administration: Intratympanic injection
   Treatment Duration: 12 weeks
Methodology
   Monocentric
   Prosepective
   Randomized
   Double-blind
   Placebo-controlled
   Parallel group
   Adaptive
Inclusion Criteria
   Male and female subjects between the 18 and 64 years of age.
   Subjects experiencing subjective tinnitus.
   Duration of tinnitus is greater than 3 months.
   No treatment of tinnitus within 4 weeks.
Evaluation Criteria
   Efficacy (Primary)
      1. Total score of the Tinnitus Questionnaire
   Efficacy (Secondary)
      1. Audiometric measurements (mode, frequency, loudness of the tinnitus, pure tone audiogram, speech audiogram)
      2. Quality of Life questionnaire
   Safety
      1. Treatment groups are compared with respect to incidence rates of premature termination, treatment-emergent adverse events, laboratory abnormalities, and ECG abnormalities.

Study Design

Subjects are divided into three treatment groups. The first group is the safety sample. The second group is the intent-to-treat (ITT) sample. The third group is the valid for efficacy (VfE) group.

For each group, one half of subjects to be given a truncated TrkC or truncated TrkB antagonist and the remainder to be given placebo.

Statistical Methods

The primary efficacy analysis is based on the total score of the Tinnitus Questionnaire in the ITT sample. The statistical analysis is based on an analysis of covariance (ANCOVA) with baseline as covariant and the last observation carried forward value as dependent variable. Factor is "treatment." The homogeneity of regression slopes is tested. The analysis is repeated for the VfE sample.

Audiometric measurements (mode, frequency, loudness of the tinnitus, pure tone audiogram, speech audiogram) as well as quality of life are also analyzed via the aforementioned model. The appropriateness of the model is not tested. P values are exploratory and are not adjusted for multiplicity.

Example 7

Table 1 illustrates exemplary sequences described herein. The DNA sequences disclosed in Table 1 encodes TrkC shRNAs described herein.

TABLE 1

| SEQ ID NOs | |
|---|---|
| 1 | GGACAATAGAGATCATCTAGT |
| 2 | CCGGGGACAATAGAGATCATCTAGTCTCGAGACTAGATGATCTCTATTGTCCTTTTTG |
| 3 | AATTCAAAAAGGACAATAGAGATCATCTAGTCTCGAGACTAGATGATCTCTATTGTCC |
| 4 | CCGGGGACATTCCAAGCCTCTTAACCTCGAGGTTAAGAGGCTTGGAATGTCCTTTTTG |
| 5 | AATTCAAAAAGGACATTCCAAGCCTCTTAACCTCGAGGTTAAGAGGCTTGGAATGTCC |
| 6 | CCGGCATGGTTTCAGAGAAATTATGCTCGAGCATAATTTCTCTGAAACCATGTTTTTG |
| 7 | AATTCAAAAACATGGTTTCAGAGAAATTATGCTCGAGCATAATTTCTCTGAAACCATG |
| 114 | GGUAUAAGUGCACACUGAAUA |
| 115 | CACUGAAUAGUCUAAUCUACA |
| 116 | GAGAGUCAAACAAUGUUAAGG |
| 117 | GAGAAGAGUUCUAUGGUUAUC |
| 118 | GACAAAGCAGUGUGCUCUAAU |
| 119 | GGAUGUGUUUGUACUUGCAGA |
| 8 (control) | CCTAAGGTTAAGTCGCCCTCG |

Table 2 illustrates sequences of the full-length and truncated isoforms of TrkC and TrkB.

TABLE 2

| | |
|---|---|
| TrkC Full-length<br>GenBank:<br>CAA12029.1<br>SEQ ID NO: 9 | MDVSLCPAKCSFWRIFLLGSVWLDYVGSVLA<br>CPANCVCSKTEINCRRPDDGNLFPLLEGQDS<br>GNSNGNASINITDISRNITSIHIENWRSLHT<br>LNAVDMELYTGLQKLTIKNSGLRSIQPRAFA<br>KNPHLRYINLSSNRLTTLSWQLFQTLSLREL<br>QLEQNFFNCSCDIRWMQLWQEQGEAKLNSQN<br>LYCINADGSQLPLFRMNISQCDLPEISVSHV<br>NLTVREGDNAVITCNGSGSPLPDVDWIVTGL<br>QSINTHQTNLNWTNVHAINLTLVNVTSEDNG<br>FTLTCIAENVVGMSNASVALTVYYPPRVVSL<br>EEPELRLEHCIEFVVRGNPPPTLHWLHNGQP<br>LRESKIIHVEYYQEGEISEGCLLFNKPTHYN<br>NGNYTLIAKNPLGTANQTINGHFLKEPFPES<br>TDNFILFDEVSPTPPITVTHKPEEDTFGVSI<br>AVGLAAFACVLLVVLFVMINKYGRRSKFGMK<br>GPVAVISGEEDSASPLHHINHGITTPSSLDA<br>GPDTVVIGMTRIPVIENPQYFRQGHNCHKPD<br>TYVQHIKRRDIVLKRELGEGAFGKVFLAECY<br>NLSPTKDKMLVAVKALKDPTLAARKDFQREA<br>ELLTNLQHEHIVKFYGVCGDGDPLIMVFEYM<br>KHGDLNKFLRAHGPDAMILVDGQPRQAKGEL<br>GLSQMLHIASQIASGMVYLASQHFVHRDLAT<br>RNCLVGANLLVKIGDFGMSRDVYSTDYYRLF<br>NPSGNDFCIWCEVGGHTMLPIRWMPPESIMY<br>RKFTTESDVWSFGVILWEIFTYGKQPWFQLS<br>NTEVIECITQGRVLERPRVCPKEVYDVMLGC<br>WQREPQQRLNIKEIYKILHALGKATPIYLDI<br>LG |
| TrkC Full-length<br>UniProtKB<br>Accession<br>Number: Q16288-3<br>SEQ ID NO: 110 | MDVSLCPAKCSFWRIFLLGSVWLDYVGSVLA<br>CPANCVCSKTEINCRRPDDGNLFPLLEGQDS<br>GNSNGNASINITDISRNITSIHIENWRSLHT<br>LNAVDMELYTGLQKLTIKNSGLRSIQPRAFA<br>KNPHLRYINLSSNRLTTLSWQLFQTLSLREL<br>QLEQNFFNCSCDIRWMQLWQEQGEAKLNSQN<br>LYCINADGSQLPLFRMNISQCDLPEISVSHV<br>NLTVREGDNAVITCNGSGSPLPDVDWIVTGL<br>QSINTHQTNLNWTNVHAINLTLVNVTSEDNG<br>FTLTCIAENVVGMSNASVALTVYYPPRVVSL<br>EEPELRLEHCIEFVVRGNPPPTLHWLHNGQP<br>LRESKIIHVEYYQEGEISEGCLLFNKPTHYN<br>NGNYTLIAKNPLGTANQTINGHFLKEPFPES<br>TDNFILFDEVSPTPPITVTHKPEEDTFGVSI<br>AVGLAAFACVLLVVLFVMINKYGRRSKFGMK<br>GPVAVISGEEDSASPLHHINHGITTPSSLDA<br>GPDTVVIGMTRIPVIENPQYFRQGHNCHKPD<br>TYVQHIKRRDIVLKRELGEGAFGKVFLAECY<br>NLSPTKDKMLVAVKALKDPTLAARKDFQREA<br>ELLTNLQHEHIVKFYGVCGDGDPLIMVFEYM<br>KHGDLNKFLRAHGPDAMILVDGQPRQAKGEL<br>GLSQMLHIASQIASGMVYLASQHFVHRDLAT<br>RNCLVGANLLVKIGDFGMSRDVYSTDYYRVG<br>GHTMLPIRWMPPESIMYRKFTTESDVWSFGV<br>ILWEIFTYGKQPWFQLSNTEVIECITQGRVL<br>ERPRVCPKEVYDVMLGCWQREPQQRLNIKEI<br>YKILHALGKATPIYLDILG |
| TrkC Full-length<br>UniProtKB<br>Accession<br>Number: Q16288-4<br>SEQ ID NO: 111 | MDVSLCPAKCSFWRIFLLGSVWLDYVGSVLA<br>CPANCVCSKTEINCRRPDDGNLFPLLEGQDS<br>GNSNGNASINITDISRNITSIHIENWRSLHT<br>LNAVDMELYTGLQKLTIKNSGLRSIQPRAFA<br>KNPHLRYINLSSNRLTTLSWQLFQTLSLREL<br>QLEQNFFNCSCDIRWMQLWQEQGEAKLNSQN<br>LYCINADGSQLPLFRMNISQCDLPEISVSHV<br>NLTVREGDNAVITCNGSGSPLPDVDWIVTGL<br>QSINTHQTNLNWTNVHAINLTLVNVTSEDNG<br>FTLTCIAENVVGMSNASVALTVYYPPRVVSL<br>EEPELRLEHCIEFVVRGNPPPTLHWLHNGQP<br>LRESKIIHVEYYQEGEISEGCLLFNKPTHYN<br>NGNYTLIAKNPLGTANQTINGHFLKEPFPVD<br>EVSPTPPITVTHKPEEDTFGVSIAVGLAAFA<br>CVLLVVLFVMINKYGRRSKFGMKGPVAVISG<br>EEDSASPLHHINHGITTPSSLDAGPDTVVIG<br>MTRIPVIENPQYFRQGHNCHKPDTYVQHIKR<br>RDIVLKRELGEGAFGKVFLAECYNLSPTKDK<br>MLVAVKALKDPTLAARKDFQREAELLTNLQH<br>EHIVKFYGVCGDGDPLIMVFEYMKHGDLNKF<br>LRAHGPDAMILVDGQPRQAKGELGLSQMLHI<br>ASQIASGMVYLASQHFVHRDLATRNCLVGAN<br>LLVKIGDFGMSRDVYSTDYYRLFNPSGNDFC<br>IWCEVGGHTMLPIRWMPPESIMYRKFTTESD<br>VWSFGVILWEIFTYGKQPWFQLSNTEVIECI<br>TQGRVLERPRVCPKEVYDVMLGCWQREPQQR<br>LNIKEIYKILHALGKATPIYLDILG |
| TrkC Full-length<br>UniProtKB<br>Accession<br>Number: Q16288-5<br>SEQ ID NO: 112 | MDVSLCPAKCSFWRIFLLGSVWLDYVGSVLA<br>CPANCVCSKTEINCRRPDDGNLFPLLEGQDS<br>GNSNGNASINITDISRNITSIHIENWRSLHT<br>LNAVDMELYTGLQKLTIKNSGLRSIQPRAFA<br>KNPHLRYINLSSNRLTTLSWQLFQTLSLREL<br>QLEQNFFNCSCDIRWMQLWQEQGEAKLNSQN<br>LYCINADGSQLPLFRMNISQCDLPEISVSHV<br>NLTVREGDNAVITCNGSGSPLPDVDWIVTGL<br>QSINTHQTNLNWTNVHAINLTLVNVTSEDNG<br>FTLTCIAENVVGMSNASVALTVYYPPRVVSL<br>EEPELRLEHCIEFVVRGNPPPTLHWLHNGQP<br>LRESKIIHVEYYQEGEISEGCLLFNKPTHYN<br>NGNYTLIAKNPLGTANQTINGHFLKEPFPVD<br>EVSPTPPITVTHKPEEDTFGVSIAVGLAAFA<br>CVLLVVLFVMINKYGRRSKFGMKGPVAVISG<br>EEDSASPLHHINHGITTPSSLDAGPDTVVIG<br>MTRIPVIENPQYFRQGHNCHKPDTYVQHIKR<br>RDIVLKRELGEGAFGKVFLAECYNLSPTKDK<br>MLVAVKALKDPTLAARKDFQREAELLTNLQH<br>EHIVKFYGVCGDGDPLIMVFEYMKHGDLNKF<br>LRAHGPDAMILVDGQPRQAKGELGLSQMLHI<br>ASQIASGMVYLASQHFVHRDLATRNCLVGAN<br>LLVKIGDFGMSRDVYSTDYYRVGGHTMLPIR<br>WMPPESIMYRKFTTESDVWSFGVILWEIFTY<br>GKQPWFQLSNTEVIECITQGRVLERPRVCPK<br>EVYDVMLGCWQREPQQRLNIKEIYKILHALG<br>KATPIYLDILG |
| TrkC.T1<br>GenBank:<br>AAB33112.1<br>SEQ ID NO: 10 | MDVSLCPAKCSFWRIFLLGSVWLDYVGSVLA<br>CPANCVCSKTEINCRRPDDGNLFPLLEGQDS<br>GNSNGNANINITDISRNITSIHIENWRSLHT<br>LNAVDMELYTGLQKLTIKNSGLRSIQPRAFA<br>KNPHLRYINLSSNRLTTLSWQLFQTLSLREL<br>QLEQNFFNCSCDIRWMQLWQEQGEAKLNSQN<br>LYCINADGSQLPLFRMNISQCDLPEISVSHV<br>NLTVREGDNAVITCNGSGSPLPDVDWIVTGL<br>QSINTHQTNLNWTNVHAINLTLVNVTSEDNG<br>FTLTCIAENVVGMSNASVALTVYYPPRVVSL<br>EEPELRLEHCIEFVVRGNPPPTLHWLHNGQP<br>LRESKIIHVEYYQEGEISEGCLLFNKPTHYN<br>NGNYTLIAKNPLGTANQTINGHFLKEPFPES<br>TDNFILFDEVSPTPPITVTHKPEEDTFGVSI<br>AVGLAAFACVLLVVLFVMINKYGRRSKFGMK<br>GPVAVISGEEDSASPLHHINHGITTPSSLDA<br>GPDTVVIGMTRIPVIENPQYFRQGHNCHKPD<br>TWVFSNIDNHGILNLKDNRDHLVPSTHYIYE<br>EPEVQSGEVSYPRSHGFREIMLNPISLPGHS<br>KPLNHGIYVEDVNVYFSKGRHGF |
| TrkC.T1<br>UniProtKB<br>Accession<br>Number: Q16288-2<br>SEQ ID NO: 113 | MDVSLCPAKCSFWRIFLLGSVWLDYVGSVLA<br>CPANCVCSKTEINCRRPDDGNLFPLLEGQDS<br>GNSNGNASINITDISRNITSIHIENWRSLHT<br>LNAVDMELYTGLQKLTIKNSGLRSIQPRAFA<br>KNPHLRYINLSSNRLTTLSWQLFQTLSLREL<br>QLEQNFFNCSCDIRWMQLWQEQGEAKLNSQN<br>LYCINADGSQLPLFRMNISQCDLPEISVSHV<br>NLTVREGDNAVITCNGSGSPLPDVDWIVTGL<br>QSINTHQTNLNWTNVHAINLTLVNVTSEDNG<br>FTLTCIAENVVGMSNASVALTVYYPPRVVSL<br>EEPELRLEHCIEFVVRGNPPPTLHWLHNGQP<br>LRESKIIHVEYYQEGEISEGCLLFNKPTHYN<br>NGNYTLIAKNPLGTANQTINGHFLKEPFPES<br>TDNFILFDEVSPTPPITVTHKPEEDTFGVSI<br>AVGLAAFACVLLVVLFVMINKYGRRSKFGMK<br>GPVAVISGEEDSASPLHHINHGITTPSSLDA<br>GPDTVVIGMTRIPVIENPQYFRQGHNCHKPD<br>TWVFSNIDNHGILNLKDNRDHLVPSTHYIYE<br>EPEVQSGEVSYPRSHGFREIMLNPISLPGHS<br>KPLNHGIYVEDVNVYFSKGRHGF |

TABLE 2-continued

| | |
|---|---|
| TrkB isoform c<br>GenBank:<br>AAB33109.1<br>SEQ ID NO: 11 | MSSWIRWHGPAMARLWGFCWLVVGFWRAAFA<br>CPTSCKCSASRIWCSDPSPGIVAFPRLEPNS<br>VDPENITEIFIANQKRLEIINEDDVEAYVGL<br>RNLTIVDSGLKFVAHKAFLKNSNLQHINFTR<br>NKLTSLSRKHFRHLDLSELILVGNPFTCSCD<br>IMWIKTLQEAKSSPDTQDLYCLNESSKNIPL<br>ANLQIPNCGLPSANLAAPNLTVEEGKSITLS<br>CSVAGDPVPNMYWDVGNLVSKHMNETSHTQG<br>SLRITNISSDDSGKQISCVAENLVGEDQDSV<br>NLTVHFAPTITFLESPTSDHHWCIPFTVKGN<br>PKPALQWFYNGAILNESKYICTKIHVTNHTE<br>YHGCLQLDNPTHMNNGDYTLIAKNEYGKDEK<br>QISAHFMGWPGIDDGANPNYPDVIYEDYGTA<br>ANDIGDTTNRSNEIPSTDVTDKTGREHLSVY<br>AVVVIASVVGFCLLVMLFLLKLARHSKFGMK<br>GPASVISNDDDSASPLHHISNGSNTPSSSEG<br>GPDAVIIGMTKIPVIENPQYFGITNSQLKPD<br>TFVQHIKRHNIVLKRELGEGAFGKVFLAECY<br>NLCPEQDKILVAVKTLKDASDNARKDFHREA<br>ELLTNLQHEHIVKFYGVCEGDPLIMVFEYM<br>KHGDLNKFLRAHGPDAVLMAEGNPPTELTQS<br>QMLHIAQQIAAGMVYLASQHFVHRDLATRNC<br>LVGENLLVKIGDFGMSRDVYSTDYYRVGGHT<br>MLPIRWMPPESIMYRKFTTESDVWSLGVVLW<br>EIFTYGKQPWYQLSNNEVIECITQGRVLQRP<br>RTCPQEVYELMLGCWQREPHMRKNIKGIHTL<br>LQNLAKASPVYLDILG |
| TrkB.T1<br>(TrkB isoform b)<br>GenBank:<br>AAM77876.1<br>SEQ ID NO: 12 | MSSWIRWHGPAMARLWGFCWLVVGFWRAAFA<br>CPTSCKCSASRIWCSDPSPGIVAFPRLEPNS<br>VDPENITEIFIANQKRLEIINEDDVEAYVGL<br>RNLTIVDSGLKFVAHKAFLKNSNLQHINFTR<br>NKLTSLSRKHFRHLDLSELILVGNPFTCSCD<br>IMWIKTLQEAKSSPDTQDLYCLNESSKNIPL<br>ANLQIPNCGLPSANLAAPNLTVEEGKSITLS<br>CSVAGDPVPNMYWDVGNLVSKHMNETSHTQG<br>SLRITNISSDDSGKQISCVAENLVGEDQDSV<br>NLTVHFAPTITFLESPTSDHHWCIPFTVKGN<br>PKPALQWFYNGAILNESKYICTKIHVTNHTE<br>YHGCLQLDNPTHMNNGDYTLIAKNEYGKDEK<br>QISAHFMGWPGIDDGANPNYPDVIYEDYGTA<br>ANDIGDTTNRSNEIPSTDVTDKTGREHLSVY<br>AVVVIASVVGFCLLVMLFLLKLARHSKFGMK<br>GFVLFHKIPLDG |
| TrkB isoform a<br>Origene Accession<br>Number:<br>NP_006171.2<br>SEQ ID NO: 120 | MSSWIRWHGPAMARLWGFCWLVVGFWRAAFA<br>CPTSCKCSASRIWCSDPSPGIVAFPRLEPNS<br>VDPENITEIFIANQKRLEIINEDDVEAYVGL<br>RNLTIVDSGLKFVAHKAFLKNSNLQHINFTR<br>NKLTSLSRKHFRHLDLSELILVGNPFTCSCD<br>IMWIKTLQEAKSSPDTQDLYCLNESSKNIPL<br>ANLQIPNCGLPSANLAAPNLTVEEGKSITLS<br>CSVAGDPVPNMYWDVGNLVSKHMNETSHTQG<br>SLRITNISSDDSGKQISCVAENLVGEDQDSV<br>NLTVHFAPTITFLESPTSDHHWCIPFTVKGN<br>PKPALQWFYNGAILNESKYICTKIHVTNHTE<br>YHGCLQLDNPTHMNNGDYTLIAKNEYGKDEK<br>QISAHFMGWPGIDDGANPNYPDVIYEDYGTA<br>ANDIGDTTNRSNEIPSTDVTDKTGREHLSVY<br>AVVVIASVVGFCLLVMLFLLKLARHSKFGMK<br>DFSWFGFGKVKSRQGVGPASVISNDDDSASP<br>LHHISNGSNTPSSSEGGGPDAVIIGMTKIPVI<br>ENPQYFGITNSQLKPDTFVQHIKRHNIVLKR<br>ELGEGAFGKVFLAECYNLCPEQDKILVAVKT<br>LKDASDNARKDFHREAELLTNLQHEHIVKFY<br>GVCVEGDPLIMVFEYMKHGDLNKFLRAHGPD<br>AVLMAEGNPPTELTQSQMLHIAQQIAAGMVY<br>LASQHFVHRDLATRNCLVGENLLVKIGDFGM<br>SRDVYSTDYYRVGGHTMLPIRWMPPESIMYR<br>KFTTESDVWSLGVVLWEIFTYGKQPWYQLSN<br>NEVIECITQGRVLQRPRTCPQEVYELMLGCW<br>QREPHMRKNIKGIHTLLQNLAKASPVYLDIL<br>G |
| TrkB isoform d<br>(TrkB-T-Shc)<br>Origene Accession<br>Number:<br>NP_001018075.1 | MSSWIRWHGPAMARLWGFCWLVVGFWRAAFA<br>CPTSCKCSASRIWCSDPSPGIVAFPRLEPNS<br>VDPENITEIFIANQKRLEIINEDDVEAYVGL<br>RNLTIVDSGLKFVAHKAFLKNSNLQHINFTR<br>NKLTSLSRKHFRHLDLSELILVGNPFTCSCD |
| SEQ ID NO: 121 | IMWIKTLQEAKSSPDTQDLYCLNESSKNIPL<br>ANLQIPNCGLPSANLAAPNLTVEEGKSITLS<br>CSVAGDPVPNMYWDVGNLVSKHMNETSHTQG<br>SLRITNISSDDSGKQISCVAENLVGEDQDSV<br>NLTVHFAPTITFLESPTSDHHWCIPFTVKGN<br>PKPALQWFYNGAILNESKYICTKIHVTNHTE<br>YHGCLQLDNPTHMNNGDYTLIAKNEYGKDEK<br>QISAHFMGWPGIDDGANPNYPDVIYEDYGTA<br>ANDIGDTTNRSNEIPSTDVTDKTGREHLSVY<br>AVVVIASVVGFCLLVMLFLLKLARHSKFGMK<br>DFSWFGFGKVKSRQGVGPASVISNDDDSASP<br>LHHISNGSNTPSSSEGGPDAVIIGMTKIPVI<br>ENPQYFGITNSQLKPDTWPRGSPKTA |
| TrkB isoform e<br>(TrkB-T-Shc)<br>Origene Accession<br>Number:<br>NP_001018076.1<br>SEQ ID NO: 122 | MSSWIRWHGPAMARLWGFCWLVVGFWRAAFA<br>CPTSCKCSASRIWCSDPSPGIVAFPRLEPNS<br>VDPENITEIFIANQKRLEIINEDDVEAYVGL<br>RNLTIVDSGLKFVAHKAFLKNSNLQHINFTR<br>NKLTSLSRKHFRHLDLSELILVGNPFTCSCD<br>IMWIKTLQEAKSSPDTQDLYCLNESSKNIPL<br>ANLQIPNCGLPSANLAAPNLTVEEGKSITLS<br>CSVAGDPVPNMYWDVGNLVSKHMNETSHTQG<br>SLRITNISSDDSGKQISCVAENLVGEDQDSV<br>NLTVHFAPTITFLESPTSDHHWCIPFTVKGN<br>PKPALQWFYNGAILNESKYICTKIHVTNHTE<br>YHGCLQLDNPTHMNNGDYTLIAKNEYGKDEK<br>QISAHFMGWPGIDDGANPNYPDVIYEDYGTA<br>ANDIGDTTNRSNEIPSTDVTDKTGREHLSVY<br>AVVVIASVVGFCLLVMLFLLKLARHSKFGMK<br>GPASVISNDDDSASPLHHISNGSNTPSSSEG<br>GPDAVIIGMTKIPVIENPQYFGITNSQLKPD<br>TWPRGSPKTA |
| TrkB isoform f<br>Origene Accession<br>Number:<br>NP_001278866.1<br>SEQ ID NO: 123 | MSSWIRWHGPAMARLWGFCWLVVGFWRAAFA<br>CPTSCKCSASRIWCSDPSPGIVAFPRLEPNS<br>VDPENITEIFIANQKRLEIINEDDVEAYVGL<br>RNLTIVDSGLKFVAHKAFLKNSNLQHINFTR<br>NKLTSLSRKHFRHLDLSELILVGNPFTCSCD<br>IMWIKTLQEAKSSPDTQDLYCLNESSKNIPL<br>ANLQIPNCGLPSANLAAPNLTVEEGKSITLS<br>CSVAGDPVPNMYWDVGNLVSKHMNETSHTQG<br>SLRITNISSDDSGKQISCVAENLVGEDQDSV<br>NLTVEIYHEWCIPFTVKGNPKPALQWFYNGA<br>ILNESKYICTKIHVTNHTEYHGCLQLDNPTH<br>MNNGDYTLIAKNEYGKDEKQISAHFMGWPGI<br>DDGANPNYPDVIYEDYGTAANDIGDTTNRSN<br>EIPSTDVTDKTGREHLSVYAVVVIASVVGFC<br>LLVMLFLLKLARHSKFGMKGFVLFHKIPLDG |

Table 3 illustrates miRNA sequences.

TABLE 3

| | miRNA | Sequence |
|---|---|---|
| SEQ ID NO: 13 | let-7b-3p | CUAUACAACCUACUGCCUUCCC |
| SEQ ID NO: 14 | let-7b-5p | UGAGGUAGUAGGUUGUGUGGUU |
| SEQ ID NO: 15 | miR-1-3p | UGGAAUGUAAAGAAGUAUGUAU |
| SEQ ID NO: 16 | miR-1-5p | ACAUACUUCUUUAUAUGCCCAU |
| SEQ ID NO: 17 | miR-9-3p | AUAAAGCUAGAUAACCGAAAGU |
| SEQ ID NO: 18 | miR-9-5p | UCUUUGGUUAUCUAGCUGUAUGA |
| SEQ ID NO: 19 | miR-10a-3p | CAAAUUCGUAUCUAGGGGAAUA |
| SEQ ID NO: 20 | miR-10a-5p | UACCCUGUAGAUCCGAAUUUGUG |
| SEQ ID NO: 21 | miR-15a-3p | CAGGCCAUAUUGUGCUGCCUCA |
| SEQ ID NO: 22 | miR-15a-5p | UAGCAGCACAUAAUGGUUUGUG |
| SEQ ID NO: 23 | miR-16-1-3p | CCAGUAUUAACUGUGCUGCUGA |
| SEQ ID NO: 24 | miR-16-2-3p | CCAAUAUUACUGUGCUGCUUUA |

TABLE 3-continued

| | miRNA | Sequence |
|---|---|---|
| SEQ ID NO: 25 | miR-16-5p | UAGCAGCACGUAAAUAUUGGCG |
| SEQ ID NO: 26 | miR-17-3p | ACUGCAGUGAAGGCACUUGUAG |
| SEQ ID NO: 27 | miR-17-5p | CAAAGUGCUUACAGUGCAGGUAG |
| SEQ ID NO: 28 | miR-18a-3p | ACUGCCCUAAGUGCUCCUUCUGG |
| SEQ ID NO: 29 | miR-18a-5p | UAAGGUGCAUCUAGUGCAGAUAG |
| SEQ ID NO: 30 | miR-20a-3p | ACUGCAUUAUGAGCACUUAAAG |
| SEQ ID NO: 31 | miR-20a-5p | UAAAGUGCUUAUAGUGCAGGUAG |
| SEQ ID NO: 32 | miR-24-3p | UGGCUCAGUUCAGCAGGAACAG |
| SEQ ID NO: 33 | miR-24-1-5p | UGCCUACUGAGCUGAUAUCAGU |
| SEQ ID NO: 34 | miR-24-2-5p | UGCCUACUGAGCUGAAACACAG |
| SEQ ID NO: 35 | miR-30e-3p | CUUUCAGUCGGAUGUUUACAGC |
| SEQ ID NO: 36 | miR-30e-5p | UGUAAACAUCCUUGACUGGAAG |
| SEQ ID NO: 37 | miR-93-3p | ACUGCUGAGCUAGCACUUCCCG |
| SEQ ID NO: 38 | miR-93-5p | CAAAGUGCUGUUCGUGCAGGUAG |
| SEQ ID NO: 39 | miR-103a-3p | AGCAGCAUUGUACAGGGCUAUGA |
| SEQ ID NO: 40 | miR-103a-2-5p | AGCUUCUUUACAGUGCUGCCUUG |
| SEQ ID NO: 41 | miR-103b | UCAUAGCCCUGUACAAUGCUGCU |
| SEQ ID NO: 42 | miR-106a-3p | CUGCAAUGUAAGCACUUCUUAC |
| SEQ ID NO: 43 | miR-106a-5p | AAAAGUGCUUACAGUGCAGGUAG |
| SEQ ID NO: 44 | miR-106b-3p | CCGCACUGUGGGUACUUGCUGC |
| SEQ ID NO: 45 | miR-106b-5p | UAAAGUGCUGACAGUGCAGAU |
| SEQ ID NO: 46 | miR-107 | AGCAGCAUUGUACAGGGCUAUCA |
| SEQ ID NO: 47 | miR-125a-3p | ACAGGUGAGGUUCUUGGGAGCC |
| SEQ ID NO: 48 | miR-125a-5p | UCCCUGAGACCCUUUAACCUGUGA |
| SEQ ID NO: 49 | miR-125b-1-3p | ACGGGUUAGGCUCUUGGGAGCU |
| SEQ ID NO: 50 | miR-125b-2-3p | UCACAAGUCAGGCUCUUGGGAC |
| SEQ ID NO: 51 | miR-125b-5p | UCCCUGAGACCCUAACUUGUGA |
| SEQ ID NO: 52 | miR-128-3p | UCACAGUGAACCGGUCUCUUU |
| SEQ ID NO: 53 | miR-128-1-5p | CGGGGCCGUAGCACUGUCUGAGA |
| SEQ ID NO: 54 | miR-128-2-5p | GGGGGCCGAUACACUGUACGAGA |
| SEQ ID NO: 55 | miR-133a-3p | UUUGGUCCCCUUCAACCAGCUG |
| SEQ ID NO: 56 | miR-133a-5p | AGCUGGUAAAAUGGAACCAAAU |
| SEQ ID NO: 57 | miR-133b | UUUGGUCCCCUUCAACCAGCUA |
| SEQ ID NO: 58 | miR-141-3p | UAACACUGUCUGGUAAAGAUGG |
| SEQ ID NO: 59 | miR-141-5p | CAUCUUCCAGUACAGUGUUGGA |
| SEQ ID NO: 60 | miR-149-3p | AGGGAGGGACGGGGGCUGUGC |
| SEQ ID NO: 61 | miR-149-5p | UCUGGCUCCGUGUCUUCACUCCC |
| SEQ ID NO: 62 | miR-182-3p | UGGUUCUAGACUUGCCAACUA |
| SEQ ID NO: 63 | miR-182-5p | UUUGGCAAUGGUAGAACUCACACU |
| SEQ ID NO: 64 | miR-188-3p | CUCCCACAUGCAGGGUUUGCA |
| SEQ ID NO: 65 | miR-188-5p | CAUCCCUUGCAUGGUGGAGGG |
| SEQ ID NO: 66 | miR-198 | GGUCCAGAGGGGAGAUAGGUUC |
| SEQ ID NO: 67 | miR-200a-3p | UAACACUGUCUGGUAACGAUGU |
| SEQ ID NO: 68 | miR-200a-5p | CAUCUUACCGGACAGUGCUGGA |
| SEQ ID NO: 69 | miR-200b-3p | UAAUACUGCCUGGUAAUGAUGA |
| SEQ ID NO: 70 | miR-200b-5p | CAUCUUACUGGGCAGCAUUGGA |
| SEQ ID NO: 71 | miR-204-3p | GCUGGGAAGGCAAAGGGACGU |
| SEQ ID NO: 72 | miR-204-5p | UUCCCUUUGUCAUCCUAUGCCU |
| SEQ ID NO: 73 | miR-206 | UGGAAUGUAAGGAAGUGUGUGG |
| SEQ ID NO: 74 | miR-221-3p | AGCUACAUUGUCUGCUGGGUUUC |
| SEQ ID NO: 75 | miR-221-5p | ACCUGGCAUACAAUGUAGAUUU |
| SEQ ID NO: 76 | miR-296-3p | GAGGGUUGGGUGGAGGCUCUCC |
| SEQ ID NO: 77 | miR-296-5p | AGGGCCCCCCCUCAAUCCUGU |
| SEQ ID NO: 78 | miR-324-5p | CGCAUCCCCUAGGGCAUUGGUGU |
| SEQ ID NO: 79 | miR-326 | CCUCUGGGCCCUUCCUCCAG |
| SEQ ID NO: 80 | miR-330-3p | GCAAAGCACACGGCCUGCAGAGA |
| SEQ ID NO: 81 | miR-331-3p | GCCCCUGGGCCUAUCCUAGAA |
| SEQ ID NO: 82 | miR-331-5p | CUAGGUAUGGUCCCAGGGAUCC |
| SEQ ID NO: 83 | miR-340-3p | UCCGUCUCAGUUACUUUAUAGC |
| SEQ ID NO: 84 | miR-340-5p | UUAUAAAGCAAUGAGACUGAUU |
| SEQ ID NO: 85 | miR-345-3p | GCCCUGAACGAGGGGUCUGGAG |
| SEQ ID NO: 86 | miR-345-5p | GCUGACUCCUAGUCCAGGGCUC |
| SEQ ID NO: 87 | miR-374a-3p | CUUAUCAGAUUGUAUUGUAAUU |
| SEQ ID NO: 88 | miR-374a-5p | UUAUAAUACAACCUGAUAAGUG |
| SEQ ID NO: 89 | miR-374b-3p | CUUAGCAGGUUGUAUUAUCAUU |
| SEQ ID NO: 90 | miR-374b-5p | AUAUAAUACAACCUGCUAAGUG |
| SEQ ID NO: 91 | miR-374c-3p | CACUUAGCAGGUUGUAUUAUAU |
| SEQ ID NO: 92 | miR-374c-5p | AUAAUACAACCUGCUAAGUGCU |
| SEQ ID NO: 93 | miR-384 | AUUCCUAGAAAUUGUUCAUA |
| SEQ ID NO: 94 | miR-412-3p | ACUUCACCUGGUCCACUAGCCGU |
| SEQ ID NO: 95 | miR-412-5p | UGGUCGACCAGUUGGAAAGUAAU |
| SEQ ID NO: 96 | miR-422a | ACUGGACUUAGGGUCAGAAGGC |
| SEQ ID NO: 97 | miR-449a | UGGCAGUGUAUUGUUAGCUGGU |
| SEQ ID NO: 98 | miR-449b-3p | CAGCCACAACUACCCUGCCACU |
| SEQ ID NO: 99 | miR-449b-5p | AGGCAGUGUAUUGUUAGCUGGC |
| SEQ ID NO: 100 | miR-449c-3p | UUGCUAGUUGCACUCCUCUCUGU |

TABLE 3-continued

| miRNA | | Sequence |
|---|---|---|
| SEQ ID NO: 101 | miR-449c-5p | UAGGCAGUGUAUUGCUAGCGGCUGU |
| SEQ ID NO: 102 | miR-485-3p | GUCAUACACGGCUCUCCUCUCU |
| SEQ ID NO: 103 | miR-509-3p | UGAUUGGUACGUCUGUGGGUAG |
| SEQ ID NO: 104 | miR-509-5p | UACUGCAGACAGUGGCAAUCA |
| SEQ ID NO: 105 | miR-509-3-5p | UACUGCAGACGUGGCAAUCAUG |
| SEQ ID NO: 106 | miR-617 | AGACUUCCAUUUGAAGGUGGC |

TABLE 3-continued

| miRNA | | Sequence |
|---|---|---|
| SEQ ID NO: 107 | miR-625-3p | GACUAUAGAACUUUCCCCCUCA |
| SEQ ID NO: 108 | miR-625-5p | AGGGGGAAAGUUCUAUAGUCC |
| SEQ ID NO: 109 | miR-765 | UGGAGGAGAAGGAAGGUGAUG |

The examples and embodiments described herein are for illustrative purposes only and various modifications or changes suggested to persons skilled in the art are to be included within the spirit and purview of this application and scope of the appended claims.

What is claimed is:

1. A pharmaceutical composition comprising:
   a) a nucleic acid polymer that is configured to hybridize to a target sequence of truncated TrkC or truncated TrkB, wherein the nucleic acid polymer is configured to decrease the expression level of the truncated TrkC or truncated TrkB upon administration of the pharmaceutical composition to a patient in need thereof; and
   b) a pharmaceutically acceptable excipient or a delivery vehicle, wherein the pharmaceutical composition is formulated for intratympanic injection and comprises poloxamer 407.

2. The pharmaceutical composition of claim 1, wherein the nucleic acid polymer is configured to hybridize to a target sequence of truncated TrkC.

3. The pharmaceutical composition of claim 1, wherein the nucleic acid polymer is configured to hybridize to a target sequence of truncated TrkB.

4. The pharmaceutical composition of claim 1, wherein the nucleic acid polymer is configured to hybridize to a target sequence that is located at the 3'UTR region of the truncated TrkC or truncated TrkB mRNA or to a target sequence comprising a binding motif selected from CCAAUC, CUCCAA, or ACUGUG.

5. The pharmaceutical composition of claim 1, wherein the nucleic acid polymer comprises a short hairpin ribonucleic acid (RNA) (shRNA) molecule, a microRNA (miRNA) molecule, a small interfering RNA (siRNA) molecule, or a double-stranded RNA molecule.

6. The pharmaceutical composition of claim 1, wherein the nucleic acid polymer comprises at least 80%, 85%, 90%, 95%, 99%, or 100% sequence identity to a nucleic acid sequence selected from SEQ ID NOs: 1-5 and 114-119.

7. The pharmaceutical composition of claim 1, wherein the nucleic acid polymer is further modified at the nucleoside moiety, at the phosphate moiety, or a combination thereof.

8. The pharmaceutical composition of claim 1, wherein the nucleic acid polymer further comprises one or more artificial nucleotide bases.

9. The pharmaceutical composition of claim 8, wherein the one or more artificial nucleotide bases comprises 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O-N-methylacetamido (2'-O-NMA) modified, locked nucleic acid (LNA), ethylene nucleic acid (ENA), peptide nucleic acid (PNA), 1', 5'-anhydrohexitol nucleic acids (HNA), morpholino, methylphosphonate nucleotides, thiolphosphonate nucleotides, or 2'-fluoro N3-P5'-phosphoramidites.

10. The pharmaceutical composition of claim 1, wherein the nucleic acid polymer is at most 10, 15, 20, 25, 30, 35, 40, 45, 50, 55, 60, 70, 80, 90, or 100 nucleotides in length.

11. The pharmaceutical composition of claim 1, further comprising a vector comprising the nucleic acid polymer.

12. The pharmaceutical composition of claim 11, wherein the vector is a viral vector selected from the group consisting of a lentiviral vector, a retroviral vector, an adenoviral vector, an adeno-associated viral vector, an alphaviral vector, a herpes simplex virus vector, a vaccinia viral vector, and a chimeric viral vector.

13. The pharmaceutical composition of claim 1, wherein the truncated TrkC is a non-catalytic truncated TrkC.

14. The pharmaceutical composition of claim 1, wherein the truncated TrkC comprises at least 80%, 85%, 90%, 95%, or 99% sequence identity to the amino acid sequence of SEQ ID NO: 10 or 113.

15. The pharmaceutical composition of claim 1, wherein the truncated TrkC is TrkC.T1.

16. The pharmaceutical composition of claim 1, wherein the truncated TrkB is a non-catalytic truncated TrkB.

17. The pharmaceutical composition of claim 1, wherein the truncated TrkB comprises at least 80%, 85%, 90%, 95%, or 99% sequence identity to an amino acid sequence selected from SEQ ID NOs: 11-12 and 121-123.

18. The pharmaceutical composition of claim 1, wherein the truncated TrkB is TrkB.T1.

19. The pharmaceutical composition of claim 1, wherein the nucleic acid polymer that is configured to hybridize to a target sequence of truncated TrkC comprises a micro-ribonucleic acid (miRNA) molecule.

20. A pharmaceutical composition comprising an isolated and purified nucleic acid polymer comprising at least 80%, 85%, 90%, 95%, 99% or 100% sequence identity to a nucleic acid sequence selected from SEQ ID NOs: 1-5 and 114-119, wherein the pharmaceutical composition is formulated for intratympanic injection and comprises poloxamer 407.

21. The isolated and purified nucleic acid polymer of claim 20, wherein the isolated and purified nucleic acid polymer is further modified at the nucleoside moiety, at the phosphate moiety, or a combination thereof.

* * * * *

SEQUENCE LISTING

```
<160> NUMBER OF SEQ ID NOS: 125

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ggacaataga gatcatctag t                                               21

<210> SEQ ID NO 2
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ccggggacaa tagagatcat ctagtctcga gactagatga tctctattgt ccttttg       58

<210> SEQ ID NO 3
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
aattcaaaaa ggacaataga gatcatctag tctcgagact agatgatctc tattgtcc     58

<210> SEQ ID NO 4
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ccggggacat ccaagcctc ttaacctcga ggttaagagg cttggaatgt ccttttg       58

<210> SEQ ID NO 5
<211> LENGTH: 58
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 5
aattcaaaaa ggacattcca agcctcttaa cctcgaggtt aagaggcttg gaatgtcc         58

<210> SEQ ID NO 6
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ccggcatggt ttcagagaaa ttatgctcga gcataatttc tctgaaacca tgttttg          58

<210> SEQ ID NO 7
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
aattcaaaaa catggtttca gagaaattat gctcgagcat aatttctctg aaaccatg         58

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
cctaaggtta agtcgccctc g                                                 21

<210> SEQ ID NO 9
<211> LENGTH: 839
<212> TYPE: PRT
<213> ORGANISM: Homo sapiens

<400> SEQUENCE: 9
```

Met Asp Val Ser Leu Cys Pro Ala Lys Cys Ser Phe Trp Arg Ile Phe
 1               5                  10                  15

Leu Leu Gly Ser Val Trp Leu Asp Tyr Val Gly Ser Val Leu Ala Cys
                20                  25                  30

Pro Ala Asn Cys Val Cys Ser Lys Thr Glu Ile Asn Cys Arg Arg Pro
            35                  40                  45

Asp Asp Gly Asn Leu Phe Pro Leu Leu Glu Gly Gln Asp Ser Gly Asn
        50                  55                  60

Ser Asn Gly Asn Ala Ser Ile Asn Ile Thr Asp Ile Ser Arg Asn Ile
65                  70                  75                  80

Thr Ser Ile His Ile Glu Asn Trp Arg Ser Leu His Thr Leu Asn Ala
                85                  90                  95

Val Asp Met Glu Leu Tyr Thr Gly Leu Gln Lys Leu Thr Ile Lys Asn
               100                 105                 110

Ser Gly Leu Arg Ser Ile Gln Pro Arg Ala Phe Ala Lys Asn Pro His
           115                 120                 125

-continued

```
Leu Arg Tyr Ile Asn Leu Ser Ser Asn Arg Leu Thr Thr Leu Ser Trp
        130                 135                 140
Gln Leu Phe Gln Thr Leu Ser Leu Arg Glu Leu Gln Leu Glu Gln Asn
145                 150                 155                 160
Phe Phe Asn Cys Ser Cys Asp Ile Arg Trp Met Gln Leu Trp Gln Glu
                165                 170                 175
Gln Gly Glu Ala Lys Leu Asn Ser Gln Asn Leu Tyr Cys Ile Asn Ala
            180                 185                 190
Asp Gly Ser Gln Leu Pro Leu Phe Arg Met Asn Ile Ser Gln Cys Asp
        195                 200                 205
Leu Pro Glu Ile Ser Val Ser His Val Asn Leu Thr Val Arg Glu Gly
210                 215                 220
Asp Asn Ala Val Ile Thr Cys Asn Gly Ser Gly Ser Pro Leu Pro Asp
225                 230                 235                 240
Val Asp Trp Ile Val Thr Gly Leu Gln Ser Ile Asn Thr His Gln Thr
                245                 250                 255
Asn Leu Asn Trp Thr Asn Val His Ala Ile Asn Leu Thr Leu Val Asn
            260                 265                 270
Val Thr Ser Glu Asp Asn Gly Phe Thr Leu Thr Cys Ile Ala Glu Asn
        275                 280                 285
Val Val Gly Met Ser Asn Ala Ser Val Ala Leu Thr Val Tyr Tyr Pro
290                 295                 300
Pro Arg Val Val Ser Leu Glu Glu Pro Glu Leu Arg Leu Glu His Cys
305                 310                 315                 320
Ile Glu Phe Val Val Arg Gly Asn Pro Pro Thr Leu His Trp Leu
                325                 330                 335
His Asn Gly Gln Pro Leu Arg Glu Ser Lys Ile Ile His Val Glu Tyr
            340                 345                 350
Tyr Gln Glu Gly Glu Ile Ser Glu Gly Cys Leu Leu Phe Asn Lys Pro
        355                 360                 365
Thr His Tyr Asn Asn Gly Asn Tyr Thr Leu Ile Ala Lys Asn Pro Leu
370                 375                 380
Gly Thr Ala Asn Gln Thr Ile Asn Gly His Phe Leu Lys Glu Pro Phe
385                 390                 395                 400
Pro Glu Ser Thr Asp Asn Phe Ile Leu Phe Asp Glu Val Ser Pro Thr
                405                 410                 415
Pro Pro Ile Thr Val Thr His Lys Pro Glu Glu Asp Thr Phe Gly Val
            420                 425                 430
Ser Ile Ala Val Gly Leu Ala Ala Phe Ala Cys Val Leu Leu Val Val
        435                 440                 445
Leu Phe Val Met Ile Asn Lys Tyr Gly Arg Arg Ser Lys Phe Gly Met
450                 455                 460
Lys Gly Pro Val Ala Val Ile Ser Gly Glu Glu Asp Ser Ala Ser Pro
465                 470                 475                 480
Leu His His Ile Asn His Gly Ile Thr Thr Pro Ser Ser Leu Asp Ala
                485                 490                 495
Gly Pro Asp Thr Val Val Ile Gly Met Thr Arg Ile Pro Val Ile Glu
            500                 505                 510
Asn Pro Gln Tyr Phe Arg Gln Gly His Asn Cys His Lys Pro Asp Thr
        515                 520                 525
Tyr Val Gln His Ile Lys Arg Arg Asp Ile Val Leu Lys Arg Glu Leu
530                 535                 540
Gly Glu Gly Ala Phe Gly Lys Val Phe Leu Ala Glu Cys Tyr Asn Leu
```

```
                        545                 550                 555                 560
        Ser Pro Thr Lys Asp Lys Met Leu Val Ala Val Lys Ala Leu Lys Asp
                        565                 570                 575

Pro Thr Leu Ala Ala Arg Lys Asp Phe Gln Arg Glu Ala Glu Leu Leu
                        580                 585                 590

Thr Asn Leu Gln His Glu His Ile Val Lys Phe Tyr Gly Val Cys Gly
                        595                 600                 605

Asp Gly Asp Pro Leu Ile Met Val Phe Glu Tyr Met Lys His Gly Asp
                        610                 615                 620

Leu Asn Lys Phe Leu Arg Ala His Gly Pro Asp Ala Met Ile Leu Val
        625                 630                 635                 640

Asp Gly Gln Pro Arg Gln Ala Lys Gly Glu Leu Gly Leu Ser Gln Met
                        645                 650                 655

Leu His Ile Ala Ser Gln Ile Ala Ser Gly Met Val Tyr Leu Ala Ser
                        660                 665                 670

Gln His Phe Val His Arg Asp Leu Ala Thr Arg Asn Cys Leu Val Gly
                        675                 680                 685

Ala Asn Leu Leu Val Lys Ile Gly Asp Phe Gly Met Ser Arg Asp Val
                        690                 695                 700

Tyr Ser Thr Asp Tyr Tyr Arg Leu Phe Asn Pro Ser Gly Asn Asp Phe
        705                 710                 715                 720

Cys Ile Trp Cys Glu Val Gly Gly His Thr Met Leu Pro Ile Arg Trp
                        725                 730                 735

Met Pro Pro Glu Ser Ile Met Tyr Arg Lys Phe Thr Thr Glu Ser Asp
                        740                 745                 750

Val Trp Ser Phe Gly Val Ile Leu Trp Glu Ile Phe Thr Tyr Gly Lys
                        755                 760                 765

Gln Pro Trp Phe Gln Leu Ser Asn Thr Glu Val Ile Glu Cys Ile Thr
                        770                 775                 780

Gln Gly Arg Val Leu Glu Arg Pro Arg Val Cys Pro Lys Glu Val Tyr
        785                 790                 795                 800

Asp Val Met Leu Gly Cys Trp Gln Arg Glu Pro Gln Gln Arg Leu Asn
                        805                 810                 815

Ile Lys Glu Ile Tyr Lys Ile Leu His Ala Leu Gly Lys Ala Thr Pro
                        820                 825                 830

Ile Tyr Leu Asp Ile Leu Gly
                        835

<210> SEQ ID NO 10
<211> LENGTH: 612
<212> TYPE: PRT
<213> ORGANISM: Homo sapiens

<400> SEQUENCE: 10

Met Asp Val Ser Leu Cys Pro Ala Lys Cys Ser Phe Trp Arg Ile Phe
1               5                   10                  15

Leu Leu Gly Ser Val Trp Leu Asp Tyr Val Gly Ser Val Leu Ala Cys
                20                  25                  30

Pro Ala Asn Cys Val Cys Ser Lys Thr Glu Ile Asn Cys Arg Arg Pro
                35                  40                  45

Asp Asp Gly Asn Leu Phe Pro Leu Leu Glu Gly Gln Asp Ser Gly Asn
                50                  55                  60

Ser Asn Gly Asn Ala Asn Ile Asn Ile Thr Asp Ile Ser Arg Asn Ile
65                  70                  75                  80
```

-continued

```
Thr Ser Ile His Ile Glu Asn Trp Arg Ser Leu His Thr Leu Asn Ala
                85                  90                  95

Val Asp Met Glu Leu Tyr Thr Gly Leu Gln Lys Leu Thr Ile Lys Asn
            100                 105                 110

Ser Gly Leu Arg Ser Ile Gln Pro Arg Ala Phe Ala Lys Asn Pro His
            115                 120                 125

Leu Arg Tyr Ile Asn Leu Ser Ser Asn Arg Leu Thr Thr Leu Ser Trp
        130                 135                 140

Gln Leu Phe Gln Thr Leu Ser Leu Arg Glu Leu Gln Leu Glu Gln Asn
145                 150                 155                 160

Phe Phe Asn Cys Ser Cys Asp Ile Arg Trp Met Gln Leu Trp Gln Glu
                165                 170                 175

Gln Gly Glu Ala Lys Leu Asn Ser Gln Asn Leu Tyr Cys Ile Asn Ala
            180                 185                 190

Asp Gly Ser Gln Leu Pro Leu Phe Arg Met Asn Ile Ser Gln Cys Asp
            195                 200                 205

Leu Pro Glu Ile Ser Val Ser His Val Asn Leu Thr Val Arg Glu Gly
        210                 215                 220

Asp Asn Ala Val Ile Thr Cys Asn Gly Ser Gly Ser Pro Leu Pro Asp
225                 230                 235                 240

Val Asp Trp Ile Val Thr Gly Leu Gln Ser Ile Asn Thr His Gln Thr
                245                 250                 255

Asn Leu Asn Trp Thr Asn Val His Ala Ile Asn Leu Thr Leu Val Asn
            260                 265                 270

Val Thr Ser Glu Asp Asn Gly Phe Thr Leu Thr Cys Ile Ala Glu Asn
            275                 280                 285

Val Val Gly Met Ser Asn Ala Ser Val Ala Leu Thr Val Tyr Tyr Pro
        290                 295                 300

Pro Arg Val Val Ser Leu Glu Glu Pro Glu Leu Arg Leu Glu His Cys
305                 310                 315                 320

Ile Glu Phe Val Val Arg Gly Asn Pro Pro Thr Leu His Trp Leu
                325                 330                 335

His Asn Gly Gln Pro Leu Arg Glu Ser Lys Ile Ile His Val Glu Tyr
            340                 345                 350

Tyr Gln Glu Gly Glu Ile Ser Glu Gly Cys Leu Leu Phe Asn Lys Pro
            355                 360                 365

Thr His Tyr Asn Asn Gly Asn Tyr Thr Leu Ile Ala Lys Asn Pro Leu
        370                 375                 380

Gly Thr Ala Asn Gln Thr Ile Asn Gly His Phe Leu Lys Glu Pro Phe
385                 390                 395                 400

Pro Glu Ser Thr Asp Asn Phe Ile Leu Phe Asp Glu Val Ser Pro Thr
                405                 410                 415

Pro Pro Ile Thr Val Thr His Lys Pro Glu Glu Asp Thr Phe Gly Val
            420                 425                 430

Ser Ile Ala Val Gly Leu Ala Ala Phe Ala Cys Val Leu Leu Val Val
            435                 440                 445

Leu Phe Val Met Ile Asn Lys Tyr Gly Arg Arg Ser Lys Phe Gly Met
        450                 455                 460

Lys Gly Pro Val Ala Val Ile Ser Gly Glu Glu Asp Ser Ala Ser Pro
465                 470                 475                 480

Leu His His Ile Asn His Gly Ile Thr Thr Pro Ser Ser Leu Asp Ala
                485                 490                 495

Gly Pro Asp Thr Val Val Ile Gly Met Thr Arg Ile Pro Val Ile Glu
```

```
                500             505              510
Asn Pro Gln Tyr Phe Arg Gln Gly His Asn Cys His Lys Pro Asp Thr
            515                 520              525

Trp Val Phe Ser Asn Ile Asp Asn His Gly Ile Leu Asn Leu Lys Asp
        530                 535             540

Asn Arg Asp His Leu Val Pro Ser Thr His Tyr Ile Tyr Glu Glu Pro
545                 550                 555                 560

Glu Val Gln Ser Gly Glu Val Ser Tyr Pro Arg Ser His Gly Phe Arg
                565                 570                 575

Glu Ile Met Leu Asn Pro Ile Ser Leu Pro Gly His Ser Lys Pro Leu
            580                 585                 590

Asn His Gly Ile Tyr Val Glu Asp Val Asn Val Tyr Phe Ser Lys Gly
        595                 600                 605

Arg His Gly Phe
    610

<210> SEQ ID NO 11
<211> LENGTH: 822
<212> TYPE: PRT
<213> ORGANISM: Homo sapiens

<400> SEQUENCE: 11

Met Ser Ser Trp Ile Arg Trp His Gly Pro Ala Met Ala Arg Leu Trp
1               5                   10                  15

Gly Phe Cys Trp Leu Val Val Gly Phe Trp Arg Ala Ala Phe Ala Cys
            20                  25                  30

Pro Thr Ser Cys Lys Cys Ser Ala Ser Arg Ile Trp Cys Ser Asp Pro
        35                  40                  45

Ser Pro Gly Ile Val Ala Phe Pro Arg Leu Glu Pro Asn Ser Val Asp
    50                  55                  60

Pro Glu Asn Ile Thr Glu Ile Phe Ile Ala Asn Gln Lys Arg Leu Glu
65                  70                  75                  80

Ile Ile Asn Glu Asp Asp Val Glu Ala Tyr Val Gly Leu Arg Asn Leu
                85                  90                  95

Thr Ile Val Asp Ser Gly Leu Lys Phe Val Ala His Lys Ala Phe Leu
            100                 105                 110

Lys Asn Ser Asn Leu Gln His Ile Asn Phe Thr Arg Asn Lys Leu Thr
        115                 120                 125

Ser Leu Ser Arg Lys His Phe Arg His Leu Asp Leu Ser Glu Leu Ile
    130                 135                 140

Leu Val Gly Asn Pro Phe Thr Cys Ser Cys Asp Ile Met Trp Ile Lys
145                 150                 155                 160

Thr Leu Gln Glu Ala Lys Ser Ser Pro Asp Thr Gln Asp Leu Tyr Cys
                165                 170                 175

Leu Asn Glu Ser Ser Lys Asn Ile Pro Leu Ala Asn Leu Gln Ile Pro
            180                 185                 190

Asn Cys Gly Leu Pro Ser Ala Asn Leu Ala Ala Pro Asn Leu Thr Val
        195                 200                 205

Glu Glu Gly Lys Ser Ile Thr Leu Ser Cys Ser Val Ala Gly Asp Pro
    210                 215                 220

Val Pro Asn Met Tyr Trp Asp Val Gly Asn Leu Val Ser Lys His Met
225                 230                 235                 240

Asn Glu Thr Ser His Thr Gln Gly Ser Leu Arg Ile Thr Asn Ile Ser
                245                 250                 255
```

-continued

Ser Asp Asp Ser Gly Lys Gln Ile Ser Cys Val Ala Glu Asn Leu Val
                260                 265                 270

Gly Glu Asp Gln Asp Ser Val Asn Leu Thr Val His Phe Ala Pro Thr
            275                 280                 285

Ile Thr Phe Leu Glu Ser Pro Thr Ser Asp His His Trp Cys Ile Pro
        290                 295                 300

Phe Thr Val Lys Gly Asn Pro Lys Pro Ala Leu Gln Trp Phe Tyr Asn
305                 310                 315                 320

Gly Ala Ile Leu Asn Glu Ser Lys Tyr Ile Cys Thr Lys Ile His Val
                325                 330                 335

Thr Asn His Thr Glu Tyr His Gly Cys Leu Gln Leu Asp Asn Pro Thr
            340                 345                 350

His Met Asn Asn Gly Asp Tyr Thr Leu Ile Ala Lys Asn Glu Tyr Gly
        355                 360                 365

Lys Asp Glu Lys Gln Ile Ser Ala His Phe Met Gly Trp Pro Gly Ile
370                 375                 380

Asp Asp Gly Ala Asn Pro Asn Tyr Pro Asp Val Ile Tyr Glu Asp Tyr
385                 390                 395                 400

Gly Thr Ala Ala Asn Asp Ile Gly Asp Thr Thr Asn Arg Ser Asn Glu
                405                 410                 415

Ile Pro Ser Thr Asp Val Thr Asp Lys Thr Gly Arg Glu His Leu Ser
            420                 425                 430

Val Tyr Ala Val Val Ile Ala Ser Val Val Gly Phe Cys Leu Leu
        435                 440                 445

Val Met Leu Phe Leu Leu Lys Leu Ala Arg His Ser Lys Phe Gly Met
450                 455                 460

Lys Gly Pro Ala Ser Val Ile Ser Asn Asp Asp Asp Ser Ala Ser Pro
465                 470                 475                 480

Leu His His Ile Ser Asn Gly Ser Asn Thr Pro Ser Ser Glu Gly
                485                 490                 495

Gly Pro Asp Ala Val Ile Ile Gly Met Thr Lys Ile Pro Val Ile Glu
            500                 505                 510

Asn Pro Gln Tyr Phe Gly Ile Thr Asn Ser Gln Leu Lys Pro Asp Thr
        515                 520                 525

Phe Val Gln His Ile Lys Arg His Asn Ile Val Leu Lys Arg Glu Leu
530                 535                 540

Gly Glu Gly Ala Phe Gly Lys Val Phe Leu Ala Glu Cys Tyr Asn Leu
545                 550                 555                 560

Cys Pro Glu Gln Asp Lys Ile Leu Val Ala Val Lys Thr Leu Lys Asp
                565                 570                 575

Ala Ser Asp Asn Ala Arg Lys Asp Phe His Arg Glu Ala Glu Leu Leu
            580                 585                 590

Thr Asn Leu Gln His Glu His Ile Val Lys Phe Tyr Gly Val Cys Val
        595                 600                 605

Glu Gly Asp Pro Leu Ile Met Val Phe Glu Tyr Met Lys His Gly Asp
610                 615                 620

Leu Asn Lys Phe Leu Arg Ala His Gly Pro Asp Ala Val Leu Met Ala
625                 630                 635                 640

Glu Gly Asn Pro Pro Thr Glu Leu Thr Gln Ser Gln Met Leu His Ile
                645                 650                 655

Ala Gln Gln Ile Ala Ala Gly Met Val Tyr Leu Ala Ser Gln His Phe
            660                 665                 670

Val His Arg Asp Leu Ala Thr Arg Asn Cys Leu Val Gly Glu Asn Leu

```
                    675                 680                 685
Leu Val Lys Ile Gly Asp Phe Gly Met Ser Arg Asp Val Tyr Ser Thr
    690                 695                 700

Asp Tyr Tyr Arg Val Gly Gly His Thr Met Leu Pro Ile Arg Trp Met
705                 710                 715                 720

Pro Pro Glu Ser Ile Met Tyr Arg Lys Phe Thr Thr Glu Ser Asp Val
                725                 730                 735

Trp Ser Leu Gly Val Val Leu Trp Glu Ile Phe Thr Tyr Gly Lys Gln
            740                 745                 750

Pro Trp Tyr Gln Leu Ser Asn Asn Glu Val Ile Glu Cys Ile Thr Gln
        755                 760                 765

Gly Arg Val Leu Gln Arg Pro Arg Thr Cys Pro Gln Glu Val Tyr Glu
    770                 775                 780

Leu Met Leu Gly Cys Trp Gln Arg Glu Pro His Met Arg Lys Asn Ile
785                 790                 795                 800

Lys Gly Ile His Thr Leu Leu Gln Asn Leu Ala Lys Ala Ser Pro Val
                805                 810                 815

Tyr Leu Asp Ile Leu Gly
            820

<210> SEQ ID NO 12
<211> LENGTH: 477
<212> TYPE: PRT
<213> ORGANISM: Homo sapiens

<400> SEQUENCE: 12

Met Ser Ser Trp Ile Arg Trp His Gly Pro Ala Met Ala Arg Leu Trp
1               5                   10                  15

Gly Phe Cys Trp Leu Val Val Gly Phe Trp Arg Ala Ala Phe Ala Cys
            20                  25                  30

Pro Thr Ser Cys Lys Cys Ser Ala Ser Arg Ile Trp Cys Ser Asp Pro
        35                  40                  45

Ser Pro Gly Ile Val Ala Phe Pro Arg Leu Glu Pro Asn Ser Val Asp
    50                  55                  60

Pro Glu Asn Ile Thr Glu Ile Phe Ile Ala Asn Gln Lys Arg Leu Glu
65                  70                  75                  80

Ile Ile Asn Glu Asp Asp Val Glu Ala Tyr Val Gly Leu Arg Asn Leu
                85                  90                  95

Thr Ile Val Asp Ser Gly Leu Lys Phe Val Ala His Lys Ala Phe Leu
            100                 105                 110

Lys Asn Ser Asn Leu Gln His Ile Asn Phe Thr Arg Asn Lys Leu Thr
        115                 120                 125

Ser Leu Ser Arg Lys His Phe Arg His Leu Asp Leu Ser Glu Leu Ile
    130                 135                 140

Leu Val Gly Asn Pro Phe Thr Cys Ser Cys Asp Ile Met Trp Ile Lys
145                 150                 155                 160

Thr Leu Gln Glu Ala Lys Ser Ser Pro Asp Thr Gln Asp Leu Tyr Cys
                165                 170                 175

Leu Asn Glu Ser Ser Lys Asn Ile Pro Leu Ala Asn Leu Gln Ile Pro
            180                 185                 190

Asn Cys Gly Leu Pro Ser Ala Asn Leu Ala Ala Pro Asn Leu Thr Val
        195                 200                 205

Glu Glu Gly Lys Ser Ile Thr Leu Ser Cys Ser Val Ala Gly Asp Pro
    210                 215                 220
```

Val Pro Asn Met Tyr Trp Asp Val Gly Asn Leu Val Ser Lys His Met
225                 230                 235                 240

Asn Glu Thr Ser His Thr Gln Gly Ser Leu Arg Ile Thr Asn Ile Ser
            245                 250                 255

Ser Asp Asp Ser Gly Lys Gln Ile Ser Cys Val Ala Glu Asn Leu Val
            260                 265                 270

Gly Glu Asp Gln Asp Ser Val Asn Leu Thr Val His Phe Ala Pro Thr
        275                 280                 285

Ile Thr Phe Leu Glu Ser Pro Thr Ser Asp His His Trp Cys Ile Pro
    290                 295                 300

Phe Thr Val Lys Gly Asn Pro Lys Pro Ala Leu Gln Trp Phe Tyr Asn
305                 310                 315                 320

Gly Ala Ile Leu Asn Glu Ser Lys Tyr Ile Cys Thr Lys Ile His Val
            325                 330                 335

Thr Asn His Thr Glu Tyr His Gly Cys Leu Gln Leu Asp Asn Pro Thr
            340                 345                 350

His Met Asn Asn Gly Asp Tyr Thr Leu Ile Ala Lys Asn Glu Tyr Gly
        355                 360                 365

Lys Asp Glu Lys Gln Ile Ser Ala His Phe Met Gly Trp Pro Gly Ile
370                 375                 380

Asp Asp Gly Ala Asn Pro Asn Tyr Pro Asp Val Ile Tyr Glu Asp Tyr
385                 390                 395                 400

Gly Thr Ala Ala Asn Asp Ile Gly Asp Thr Thr Asn Arg Ser Asn Glu
            405                 410                 415

Ile Pro Ser Thr Asp Val Thr Asp Lys Thr Gly Arg Glu His Leu Ser
        420                 425                 430

Val Tyr Ala Val Val Val Ile Ala Ser Val Val Gly Phe Cys Leu Leu
    435                 440                 445

Val Met Leu Phe Leu Leu Lys Leu Ala Arg His Ser Lys Phe Gly Met
450                 455                 460

Lys Gly Phe Val Leu Phe His Lys Ile Pro Leu Asp Gly
465                 470                 475

<210> SEQ ID NO 13
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
cuauacaacc uacugccuuc cc                                                  22

<210> SEQ ID NO 14
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
ugagguagua gguugugugg uu                                                  22

<210> SEQ ID NO 15
<211> LENGTH: 22
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 15
uggaauguaa agaaguaugu au                                                  22

<210> SEQ ID NO 16
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
acauacuucu uuauaugccc au                                                  22

<210> SEQ ID NO 17
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
auaaagcuag auaaccgaaa gu                                                  22

<210> SEQ ID NO 18
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
ucuuugguua ucuagcugua uga                                                 23

<210> SEQ ID NO 19
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
caaauucgua ucuagggggaa ua                                                 22

<210> SEQ ID NO 20
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
uacccuguag auccgaauuu gug                                                 23

<210> SEQ ID NO 21
<211> LENGTH: 22
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 21
caggccauau ugugcugccu ca                                              22

<210> SEQ ID NO 22
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
uagcagcaca uaaugguuug ug                                              22

<210> SEQ ID NO 23
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
ccaguauuaa cugugcugcu ga                                              22

<210> SEQ ID NO 24
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
ccaauauuac ugugcugcuu ua                                              22

<210> SEQ ID NO 25
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
uagcagcacg uaaauauugg cg                                              22

<210> SEQ ID NO 26
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
acugcaguga aggcacuugu ag                                              22

<210> SEQ ID NO 27
<211> LENGTH: 23
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 27
caaagugcuu acagugcagg uag                                            23

<210> SEQ ID NO 28
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
acugcccuaa gugcuccuuc ugg                                            23

<210> SEQ ID NO 29
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
uaaggugcau cuagugcaga uag                                            23

<210> SEQ ID NO 30
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
acugcauuau gagcacuuaa ag                                             22

<210> SEQ ID NO 31
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
uaaagugcuu auagugcagg uag                                            23

<210> SEQ ID NO 32
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
uggcucaguu cagcaggaac ag                                             22

<210> SEQ ID NO 33
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
ugccuacuga gcugauauca gu                                           22

<210> SEQ ID NO 34
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
ugccuacuga gcugaaacac ag                                           22

<210> SEQ ID NO 35
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
cuuucagucg gauguuuaca gc                                           22

<210> SEQ ID NO 36
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
uguaaacauc cuugacugga ag                                           22

<210> SEQ ID NO 37
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
acugcugagc uagcacuucc cg                                           22

<210> SEQ ID NO 38
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
caaagugcug uucgugcagg uag                                          23

<210> SEQ ID NO 39
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 39
agcagcauug uacagggcua uga                                           23

<210> SEQ ID NO 40
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
agcuucuuua cagugcugcc uug                                           23

<210> SEQ ID NO 41
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
ucauagcccu guacaaugcu gcu                                           23

<210> SEQ ID NO 42
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
cugcaaugua agcacuucuu ac                                            22

<210> SEQ ID NO 43
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
aaaagugcuu acagugcagg uag                                           23

<210> SEQ ID NO 44
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
ccgcacugug gguacuugcu gc                                            22

<210> SEQ ID NO 45
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
```
uaaagugcug acagugcaga u                                              21

<210> SEQ ID NO 46
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
agcagcauug uacagggcua uca                                            23

<210> SEQ ID NO 47
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
acaggugagg uucuugggag cc                                             22

<210> SEQ ID NO 48
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
ucccugagac ccuuuaaccu guga                                           24

<210> SEQ ID NO 49
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
acggguuagg cucuugggag cu                                             22

<210> SEQ ID NO 50
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
ucacaaguca ggcucuuggg ac                                             22

<210> SEQ ID NO 51
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51

```
ucccugagac ccuaacuugu ga                                              22
```

<210> SEQ ID NO 52
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52

```
ucacagugaa ccggucucuu u                                               21
```

<210> SEQ ID NO 53
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53

```
cggggccgua gcacugucug aga                                             23
```

<210> SEQ ID NO 54
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54

```
gggggccgau acacuguacg aga                                             23
```

<210> SEQ ID NO 55
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55

```
uuuggucccc uucaaccagc ug                                              22
```

<210> SEQ ID NO 56
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56

```
agcugguaaa auggaaccaa au                                              22
```

<210> SEQ ID NO 57
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57

```
uuuggucccc uucaaccagc ua                                              22
```

<210> SEQ ID NO 58
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
uaacacuguc ugguaaagau gg                                            22

<210> SEQ ID NO 59
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
caucuuccag uacaguguug ga                                            22

<210> SEQ ID NO 60
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
agggagggac gggggcugug c                                             21

<210> SEQ ID NO 61
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
ucuggcuccg ugucuucacu ccc                                           23

<210> SEQ ID NO 62
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
ugguucuaga cuugccaacu a                                             21

<210> SEQ ID NO 63
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
uuuggcaaug guagaacuca cacu                                          24

```
<210> SEQ ID NO 64
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
cucccacaug caggguuugc a                                              21

<210> SEQ ID NO 65
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
caucccuugc augguggagg g                                              21

<210> SEQ ID NO 66
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
gguccagagg ggagauaggu uc                                             22

<210> SEQ ID NO 67
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
uaacacuguc ugguaacgau gu                                             22

<210> SEQ ID NO 68
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
caucuuaccg gacagugcug ga                                             22

<210> SEQ ID NO 69
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
uaauacugcc ugguaaugau ga                                             22
```

```
<210> SEQ ID NO 70
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
caucuuacug ggcagcauug ga                                          22

<210> SEQ ID NO 71
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
gcugggaagg caaagggacg u                                           21

<210> SEQ ID NO 72
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
uucccuuugu cauccuaugc cu                                          22

<210> SEQ ID NO 73
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
uggaauguaa ggaagugugu gg                                          22

<210> SEQ ID NO 74
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
agcuacauug ucugcugggu uuc                                         23

<210> SEQ ID NO 75
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
accuggcaua caauguagau uu                                          22

<210> SEQ ID NO 76
```

```
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
gaggguuggg uggaggcucu cc                                              22

<210> SEQ ID NO 77
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
agggcccccc cucaauccug u                                               21

<210> SEQ ID NO 78
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78 cgcaucccccu agggcauugg ugu                                            23

<210> SEQ ID NO 79
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
ccucugggcc cuuccuccag                                                 20

<210> SEQ ID NO 80
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
gcaaagcaca cggccugcag aga                                             23

<210> SEQ ID NO 81
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
gccccugggc cuauccuaga a                                               21

<210> SEQ ID NO 82
<211> LENGTH: 22
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
cuagguaugg ucccagggau cc                                              22

<210> SEQ ID NO 83
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
uccgucucag uuacuuuaua gc                                              22

<210> SEQ ID NO 84
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
uuauaaagca augagacuga uu                                              22

<210> SEQ ID NO 85
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
gcccugaacg aggggucugg ag                                              22

<210> SEQ ID NO 86
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
gcugacuccu aguccagggc uc                                              22

<210> SEQ ID NO 87
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
cuuaucagau uguauuguaa uu                                              22

<210> SEQ ID NO 88
<211> LENGTH: 22
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 88
uuauaauaca accugauaag ug                                              22

<210> SEQ ID NO 89
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
cuuagcaggu uguauuauca uu                                              22

<210> SEQ ID NO 90
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
auauaauaca accugcuaag ug                                              22

<210> SEQ ID NO 91
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
cacuuagcag guuguauuau au                                              22

<210> SEQ ID NO 92
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
auaauacaac cugcuaagug cu                                              22

<210> SEQ ID NO 93
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
auuccuagaa auuguucaua                                                 20

<210> SEQ ID NO 94
<211> LENGTH: 23
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 94
acuucaccug guccacuagc cgu                                              23

<210> SEQ ID NO 95
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
uggucgacca guuggaaagu aau                                              23

<210> SEQ ID NO 96
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
acuggacuua gggucagaag gc                                               22

<210> SEQ ID NO 97
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
uggcagugua uuguuagcug gu                                               22

<210> SEQ ID NO 98
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
cagccacaac uacccugcca cu                                               22

<210> SEQ ID NO 99
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
aggcagugua uuguuagcug gc                                               22

<210> SEQ ID NO 100
<211> LENGTH: 23
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 100
uugcuaguug cacuccucuc ugu                                          23

<210> SEQ ID NO 101
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
uaggcagugu auugcuagcg gcugu                                        25

<210> SEQ ID NO 102
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
gucauacacg gcucuccucu cu                                           22

<210> SEQ ID NO 103
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
ugauugguac gucugugggu ag                                           22

<210> SEQ ID NO 104
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
uacugcagac aguggcaauc a                                            21

<210> SEQ ID NO 105
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
uacugcagac guggcaauca ug                                           22

<210> SEQ ID NO 106
<211> LENGTH: 22
<212> TYPE: RNA
<213> ORGANISM: Artificial Sequence
<220> FEATURE:
<223> OTHER INFORMATION: Description of Artificial Sequence: Synthetic
```

-continued oligonucleotide

<400> SEQUENCE: 106
agacuuccca uuugaaggug gc                                                   22

<210> SEQ ID NO 107
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107
gacuauagaa cuucccccu ca                                                    22

<210> SEQ ID NO 108
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108 aggggggaaag uucuauaguc c                                                   21

<210> SEQ ID NO 109
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
uggaggagaa ggaaggugau g                                                    21

<210> SEQ ID NO 110
<211> LENGTH: 825
<212> TYPE: PRT
<213> ORGANISM: Homo sapiens

<400> SEQUENCE: 110

Met Asp Val Ser Leu Cys Pro Ala Lys Cys Ser Phe Trp Arg Ile Phe
1               5                   10                  15

Leu Leu Gly Ser Val Trp Leu Asp Tyr Val Gly Ser Val Leu Ala Cys
                20                  25                  30

Pro Ala Asn Cys Val Cys Ser Lys Thr Glu Ile Asn Cys Arg Arg Pro
            35                  40                  45

Asp Asp Gly Asn Leu Phe Pro Leu Leu Glu Gly Gln Asp Ser Gly Asn
        50                  55                  60

Ser Asn Gly Asn Ala Ser Ile Asn Ile Thr Asp Ile Ser Arg Asn Ile
65                  70                  75                  80

Thr Ser Ile His Ile Glu Asn Trp Arg Ser Leu His Thr Leu Asn Ala
                85                  90                  95

Val Asp Met Glu Leu Tyr Thr Gly Leu Gln Lys Leu Thr Ile Lys Asn
                100                 105                 110

Ser Gly Leu Arg Ser Ile Gln Pro Arg Ala Phe Ala Lys Asn Pro His
            115                 120                 125

Leu Arg Tyr Ile Asn Leu Ser Ser Asn Arg Leu Thr Thr Leu Ser Trp
        130                 135                 140

```
Gln Leu Phe Gln Thr Leu Ser Leu Arg Glu Leu Gln Leu Glu Gln Asn
145                 150                 155                 160

Phe Phe Asn Cys Ser Cys Asp Ile Arg Trp Met Gln Leu Trp Gln Glu
            165                 170                 175

Gln Gly Glu Ala Lys Leu Asn Ser Gln Asn Leu Tyr Cys Ile Asn Ala
        180                 185                 190

Asp Gly Ser Gln Leu Pro Leu Phe Arg Met Asn Ile Ser Gln Cys Asp
        195                 200                 205

Leu Pro Glu Ile Ser Val Ser His Val Asn Leu Thr Val Arg Glu Gly
        210                 215                 220

Asp Asn Ala Val Ile Thr Cys Asn Gly Ser Gly Ser Pro Leu Pro Asp
225                 230                 235                 240

Val Asp Trp Ile Val Thr Gly Leu Gln Ser Ile Asn Thr His Gln Thr
            245                 250                 255

Asn Leu Asn Trp Thr Asn Val His Ala Ile Asn Leu Thr Leu Val Asn
            260                 265                 270

Val Thr Ser Glu Asp Asn Gly Phe Thr Leu Thr Cys Ile Ala Glu Asn
        275                 280                 285

Val Val Gly Met Ser Asn Ala Ser Val Ala Leu Thr Val Tyr Tyr Pro
290                 295                 300

Pro Arg Val Val Ser Leu Glu Glu Pro Glu Leu Arg Leu Glu His Cys
305                 310                 315                 320

Ile Glu Phe Val Val Arg Gly Asn Pro Pro Thr Leu His Trp Leu
            325                 330                 335

His Asn Gly Gln Pro Leu Arg Glu Ser Lys Ile Ile His Val Glu Tyr
        340                 345                 350

Tyr Gln Glu Gly Glu Ile Ser Glu Gly Cys Leu Leu Phe Asn Lys Pro
        355                 360                 365

Thr His Tyr Asn Asn Gly Asn Tyr Thr Leu Ile Ala Lys Asn Pro Leu
        370                 375                 380

Gly Thr Ala Asn Gln Thr Ile Asn Gly His Phe Leu Lys Glu Pro Phe
385                 390                 395                 400

Pro Glu Ser Thr Asp Asn Phe Ile Leu Phe Asp Glu Val Ser Pro Thr
            405                 410                 415

Pro Pro Ile Thr Val Thr His Lys Pro Glu Glu Asp Thr Phe Gly Val
            420                 425                 430

Ser Ile Ala Val Gly Leu Ala Ala Phe Ala Cys Val Leu Leu Val Val
        435                 440                 445

Leu Phe Val Met Ile Asn Lys Tyr Gly Arg Arg Ser Lys Phe Gly Met
        450                 455                 460

Lys Gly Pro Val Ala Val Ile Ser Gly Glu Glu Asp Ser Ala Ser Pro
465                 470                 475                 480

Leu His His Ile Asn His Gly Ile Thr Thr Pro Ser Ser Leu Asp Ala
            485                 490                 495

Gly Pro Asp Thr Val Val Ile Gly Met Thr Arg Ile Pro Val Ile Glu
            500                 505                 510

Asn Pro Gln Tyr Phe Arg Gln Gly His Asn Cys His Lys Pro Asp Thr
            515                 520                 525

Tyr Val Gln His Ile Lys Arg Arg Asp Ile Val Leu Lys Arg Glu Leu
        530                 535                 540

Gly Glu Gly Ala Phe Gly Lys Val Phe Leu Ala Glu Cys Tyr Asn Leu
545                 550                 555                 560
```

```
Ser Pro Thr Lys Asp Lys Met Leu Val Ala Val Lys Ala Leu Lys Asp
                565                 570                 575

Pro Thr Leu Ala Ala Arg Lys Asp Phe Gln Arg Glu Ala Glu Leu Leu
            580                 585                 590

Thr Asn Leu Gln His Glu His Ile Val Lys Phe Tyr Gly Val Cys Gly
        595                 600                 605

Asp Gly Asp Pro Leu Ile Met Val Phe Glu Tyr Met Lys His Gly Asp
    610                 615                 620

Leu Asn Lys Phe Leu Arg Ala His Gly Pro Asp Ala Met Ile Leu Val
625                 630                 635                 640

Asp Gly Gln Pro Arg Gln Ala Lys Gly Glu Leu Gly Leu Ser Gln Met
                645                 650                 655

Leu His Ile Ala Ser Gln Ile Ala Ser Gly Met Val Tyr Leu Ala Ser
            660                 665                 670

Gln His Phe Val His Arg Asp Leu Ala Thr Arg Asn Cys Leu Val Gly
        675                 680                 685

Ala Asn Leu Leu Val Lys Ile Gly Asp Phe Gly Met Ser Arg Asp Val
    690                 695                 700

Tyr Ser Thr Asp Tyr Tyr Arg Val Gly Gly His Thr Met Leu Pro Ile
705                 710                 715                 720

Arg Trp Met Pro Pro Glu Ser Ile Met Tyr Arg Lys Phe Thr Thr Glu
                725                 730                 735

Ser Asp Val Trp Ser Phe Gly Val Ile Leu Trp Glu Ile Phe Thr Tyr
            740                 745                 750

Gly Lys Gln Pro Trp Phe Gln Leu Ser Asn Thr Glu Val Ile Glu Cys
        755                 760                 765

Ile Thr Gln Gly Arg Val Leu Glu Arg Pro Arg Val Cys Pro Lys Glu
    770                 775                 780

Val Tyr Asp Val Met Leu Gly Cys Trp Gln Arg Glu Pro Gln Gln Arg
785                 790                 795                 800

Leu Asn Ile Lys Glu Ile Tyr Lys Ile Leu His Ala Leu Gly Lys Ala
                805                 810                 815

Thr Pro Ile Tyr Leu Asp Ile Leu Gly
            820                 825

<210> SEQ ID NO 111
<211> LENGTH: 831
<212> TYPE: PRT
<213> ORGANISM: Homo sapiens

<400> SEQUENCE: 111

Met Asp Val Ser Leu Cys Pro Ala Lys Cys Ser Phe Trp Arg Ile Phe
1               5                   10                  15

Leu Leu Gly Ser Val Trp Leu Asp Tyr Val Gly Ser Val Leu Ala Cys
            20                  25                  30

Pro Ala Asn Cys Val Cys Ser Lys Thr Glu Ile Asn Cys Arg Arg Pro
        35                  40                  45

Asp Asp Gly Asn Leu Phe Pro Leu Leu Glu Gly Gln Asp Ser Gly Asn
    50                  55                  60

Ser Asn Gly Asn Ala Ser Ile Asn Ile Thr Asp Ile Ser Arg Asn Ile
65                  70                  75                  80

Thr Ser Ile His Ile Glu Asn Trp Arg Ser Leu His Thr Leu Asn Ala
                85                  90                  95

Val Asp Met Glu Leu Tyr Thr Gly Leu Gln Lys Leu Thr Ile Lys Asn
            100                 105                 110
```

```
Ser Gly Leu Arg Ser Ile Gln Pro Arg Ala Phe Ala Lys Asn Pro His
        115                 120                 125

Leu Arg Tyr Ile Asn Leu Ser Ser Asn Arg Leu Thr Thr Leu Ser Trp
    130                 135                 140

Gln Leu Phe Gln Thr Leu Ser Leu Arg Glu Leu Gln Leu Glu Gln Asn
145                 150                 155                 160

Phe Phe Asn Cys Ser Cys Asp Ile Arg Trp Met Gln Leu Trp Gln Glu
                165                 170                 175

Gln Gly Glu Ala Lys Leu Asn Ser Gln Asn Leu Tyr Cys Ile Asn Ala
                180                 185                 190

Asp Gly Ser Gln Leu Pro Leu Phe Arg Met Asn Ile Ser Gln Cys Asp
                195                 200                 205

Leu Pro Glu Ile Ser Val Ser His Val Asn Leu Thr Val Arg Glu Gly
    210                 215                 220

Asp Asn Ala Val Ile Thr Cys Asn Gly Ser Gly Ser Pro Leu Pro Asp
225                 230                 235                 240

Val Asp Trp Ile Val Thr Gly Leu Gln Ser Ile Asn Thr His Gln Thr
                245                 250                 255

Asn Leu Asn Trp Thr Asn Val His Ala Ile Asn Leu Thr Leu Val Asn
                260                 265                 270

Val Thr Ser Glu Asp Asn Gly Phe Thr Leu Thr Cys Ile Ala Glu Asn
    275                 280                 285

Val Val Gly Met Ser Asn Ala Ser Val Ala Leu Thr Val Tyr Tyr Pro
    290                 295                 300

Pro Arg Val Val Ser Leu Glu Glu Pro Glu Leu Arg Leu Glu His Cys
305                 310                 315                 320

Ile Glu Phe Val Val Arg Gly Asn Pro Pro Thr Leu His Trp Leu
                325                 330                 335

His Asn Gly Gln Pro Leu Arg Glu Ser Lys Ile Ile His Val Glu Tyr
                340                 345                 350

Tyr Gln Glu Gly Glu Ile Ser Glu Gly Cys Leu Leu Phe Asn Lys Pro
                355                 360                 365

Thr His Tyr Asn Asn Gly Asn Tyr Thr Leu Ile Ala Lys Asn Pro Leu
    370                 375                 380

Gly Thr Ala Asn Gln Thr Ile Asn Gly His Phe Leu Lys Glu Pro Phe
385                 390                 395                 400

Pro Val Asp Glu Val Ser Pro Thr Pro Ile Thr Val Thr His Lys
                405                 410                 415

Pro Glu Glu Asp Thr Phe Gly Val Ser Ile Ala Val Gly Leu Ala Ala
                420                 425                 430

Phe Ala Cys Val Leu Leu Val Val Leu Phe Val Met Ile Asn Lys Tyr
                435                 440                 445

Gly Arg Arg Ser Lys Phe Gly Met Lys Gly Pro Val Ala Val Ile Ser
    450                 455                 460

Gly Glu Glu Asp Ser Ala Ser Pro Leu His His Ile Asn His Gly Ile
465                 470                 475                 480

Thr Thr Pro Ser Ser Leu Asp Ala Gly Pro Asp Thr Val Val Ile Gly
                485                 490                 495

Met Thr Arg Ile Pro Val Ile Glu Asn Pro Gln Tyr Phe Arg Gln Gly
                500                 505                 510

His Asn Cys His Lys Pro Asp Thr Tyr Val Gln His Ile Lys Arg Arg
                515                 520                 525
```

```
Asp Ile Val Leu Lys Arg Glu Leu Gly Glu Gly Ala Phe Gly Lys Val
    530                 535                 540

Phe Leu Ala Glu Cys Tyr Asn Leu Ser Pro Thr Lys Asp Lys Met Leu
545                 550                 555                 560

Val Ala Val Lys Ala Leu Lys Asp Pro Thr Leu Ala Ala Arg Lys Asp
                565                 570                 575

Phe Gln Arg Glu Ala Glu Leu Leu Thr Asn Leu Gln His Glu His Ile
            580                 585                 590

Val Lys Phe Tyr Gly Val Cys Gly Asp Gly Asp Pro Leu Ile Met Val
        595                 600                 605

Phe Glu Tyr Met Lys His Gly Asp Leu Asn Lys Phe Leu Arg Ala His
    610                 615                 620

Gly Pro Asp Ala Met Ile Leu Val Asp Gly Gln Pro Arg Gln Ala Lys
625                 630                 635                 640

Gly Glu Leu Gly Leu Ser Gln Met Leu His Ile Ala Ser Gln Ile Ala
                645                 650                 655

Ser Gly Met Val Tyr Leu Ala Ser Gln His Phe Val His Arg Asp Leu
            660                 665                 670

Ala Thr Arg Asn Cys Leu Val Gly Ala Asn Leu Leu Val Lys Ile Gly
        675                 680                 685

Asp Phe Gly Met Ser Arg Asp Val Tyr Ser Thr Asp Tyr Tyr Arg Leu
    690                 695                 700

Phe Asn Pro Ser Gly Asn Asp Phe Cys Ile Trp Cys Glu Val Gly Gly
705                 710                 715                 720

His Thr Met Leu Pro Ile Arg Trp Met Pro Pro Glu Ser Ile Met Tyr
                725                 730                 735

Arg Lys Phe Thr Thr Glu Ser Asp Val Trp Ser Phe Gly Val Ile Leu
            740                 745                 750

Trp Glu Ile Phe Thr Tyr Gly Lys Gln Pro Trp Phe Gln Leu Ser Asn
        755                 760                 765

Thr Glu Val Ile Glu Cys Ile Thr Gln Gly Arg Val Leu Glu Arg Pro
    770                 775                 780

Arg Val Cys Pro Lys Glu Val Tyr Asp Val Met Leu Gly Cys Trp Gln
785                 790                 795                 800

Arg Glu Pro Gln Gln Arg Leu Asn Ile Lys Glu Ile Tyr Lys Ile Leu
                805                 810                 815

His Ala Leu Gly Lys Ala Thr Pro Ile Tyr Leu Asp Ile Leu Gly
            820                 825                 830

<210> SEQ ID NO 112
<211> LENGTH: 817
<212> TYPE: PRT
<213> ORGANISM: Homo sapiens

<400> SEQUENCE: 112

Met Asp Val Ser Leu Cys Pro Ala Lys Cys Ser Phe Trp Arg Ile Phe
1               5                   10                  15

Leu Leu Gly Ser Val Trp Leu Asp Tyr Val Gly Ser Val Leu Ala Cys
            20                  25                  30

Pro Ala Asn Cys Val Cys Ser Lys Thr Glu Ile Asn Cys Arg Arg Pro
        35                  40                  45

Asp Asp Gly Asn Leu Phe Pro Leu Leu Glu Gly Gln Asp Ser Gly Asn
    50                  55                  60

Ser Asn Gly Asn Ala Ser Ile Asn Ile Thr Asp Ile Ser Arg Asn Ile
65                  70                  75                  80
```

```
Thr Ser Ile His Ile Glu Asn Trp Arg Ser Leu His Thr Leu Asn Ala
            85                  90                  95
Val Asp Met Glu Leu Tyr Thr Gly Leu Gln Lys Leu Thr Ile Lys Asn
            100                 105                 110
Ser Gly Leu Arg Ser Ile Gln Pro Arg Ala Phe Ala Lys Asn Pro His
            115                 120                 125
Leu Arg Tyr Ile Asn Leu Ser Ser Asn Arg Leu Thr Thr Leu Ser Trp
            130                 135                 140
Gln Leu Phe Gln Thr Leu Ser Leu Arg Glu Leu Gln Leu Glu Gln Asn
145                 150                 155                 160
Phe Phe Asn Cys Ser Cys Asp Ile Arg Trp Met Gln Leu Trp Gln Glu
                165                 170                 175
Gln Gly Glu Ala Lys Leu Asn Ser Gln Asn Leu Tyr Cys Ile Asn Ala
                180                 185                 190
Asp Gly Ser Gln Leu Pro Leu Phe Arg Met Asn Ile Ser Gln Cys Asp
            195                 200                 205
Leu Pro Glu Ile Ser Val Ser His Val Asn Leu Thr Val Arg Glu Gly
            210                 215                 220
Asp Asn Ala Val Ile Thr Cys Asn Gly Ser Gly Ser Pro Leu Pro Asp
225                 230                 235                 240
Val Asp Trp Ile Val Thr Gly Leu Gln Ser Ile Asn Thr His Gln Thr
            245                 250                 255
Asn Leu Asn Trp Thr Asn Val His Ala Ile Asn Leu Thr Leu Val Asn
            260                 265                 270
Val Thr Ser Glu Asp Asn Gly Phe Thr Leu Thr Cys Ile Ala Glu Asn
            275                 280                 285
Val Val Gly Met Ser Asn Ala Ser Val Ala Leu Thr Val Tyr Tyr Pro
            290                 295                 300
Pro Arg Val Val Ser Leu Glu Glu Pro Glu Leu Arg Leu Glu His Cys
305                 310                 315                 320
Ile Glu Phe Val Val Arg Gly Asn Pro Pro Thr Leu His Trp Leu
            325                 330                 335
His Asn Gly Gln Pro Leu Arg Glu Ser Lys Ile Ile His Val Glu Tyr
            340                 345                 350
Tyr Gln Glu Gly Glu Ile Ser Glu Gly Cys Leu Leu Phe Asn Lys Pro
            355                 360                 365
Thr His Tyr Asn Asn Gly Asn Tyr Thr Leu Ile Ala Lys Asn Pro Leu
            370                 375                 380
Gly Thr Ala Asn Gln Thr Ile Asn Gly His Phe Leu Lys Glu Pro Phe
385                 390                 395                 400
Pro Val Asp Glu Val Ser Pro Thr Pro Ile Thr Val Thr His Lys
            405                 410                 415
Pro Glu Glu Asp Thr Phe Gly Val Ser Ile Ala Val Gly Leu Ala Ala
            420                 425                 430
Phe Ala Cys Val Leu Leu Val Val Leu Phe Val Met Ile Asn Lys Tyr
            435                 440                 445
Gly Arg Arg Ser Lys Phe Gly Met Lys Gly Pro Val Ala Val Ile Ser
            450                 455                 460
Gly Glu Glu Asp Ser Ala Ser Pro Leu His His Ile Asn His Gly Ile
465                 470                 475                 480
Thr Thr Pro Ser Ser Leu Asp Ala Gly Pro Asp Thr Val Val Ile Gly
            485                 490                 495
```

```
Met Thr Arg Ile Pro Val Ile Glu Asn Pro Gln Tyr Phe Arg Gln Gly
            500                 505                 510

His Asn Cys His Lys Pro Asp Thr Tyr Val Gln His Ile Lys Arg Arg
        515                 520                 525

Asp Ile Val Leu Lys Arg Glu Leu Gly Glu Gly Ala Phe Gly Lys Val
    530                 535                 540

Phe Leu Ala Glu Cys Tyr Asn Leu Ser Pro Thr Lys Asp Lys Met Leu
545                 550                 555                 560

Val Ala Val Lys Ala Leu Lys Asp Pro Thr Leu Ala Ala Arg Lys Asp
                565                 570                 575

Phe Gln Arg Glu Ala Glu Leu Leu Thr Asn Leu Gln His Glu His Ile
            580                 585                 590

Val Lys Phe Tyr Gly Val Cys Gly Asp Gly Asp Pro Leu Ile Met Val
        595                 600                 605

Phe Glu Tyr Met Lys His Gly Asp Leu Asn Lys Phe Leu Arg Ala His
    610                 615                 620

Gly Pro Asp Ala Met Ile Leu Val Asp Gly Gln Pro Arg Gln Ala Lys
625                 630                 635                 640

Gly Glu Leu Gly Leu Ser Gln Met Leu His Ile Ala Ser Gln Ile Ala
                645                 650                 655

Ser Gly Met Val Tyr Leu Ala Ser Gln His Phe Val His Arg Asp Leu
            660                 665                 670

Ala Thr Arg Asn Cys Leu Val Gly Ala Asn Leu Leu Val Lys Ile Gly
        675                 680                 685

Asp Phe Gly Met Ser Arg Asp Val Tyr Ser Thr Asp Tyr Tyr Arg Val
    690                 695                 700

Gly Gly His Thr Met Leu Pro Ile Arg Trp Met Pro Pro Glu Ser Ile
705                 710                 715                 720

Met Tyr Arg Lys Phe Thr Thr Glu Ser Asp Val Trp Ser Phe Gly Val
                725                 730                 735

Ile Leu Trp Glu Ile Phe Thr Tyr Gly Lys Gln Pro Trp Phe Gln Leu
            740                 745                 750

Ser Asn Thr Glu Val Ile Glu Cys Ile Thr Gln Gly Arg Val Leu Glu
        755                 760                 765

Arg Pro Arg Val Cys Pro Lys Glu Val Tyr Asp Val Met Leu Gly Cys
    770                 775                 780

Trp Gln Arg Glu Pro Gln Gln Arg Leu Asn Ile Lys Glu Ile Tyr Lys
785                 790                 795                 800

Ile Leu His Ala Leu Gly Lys Ala Thr Pro Ile Tyr Leu Asp Ile Leu
                805                 810                 815

Gly

<210> SEQ ID NO 113
<211> LENGTH: 612
<212> TYPE: PRT
<213> ORGANISM: Homo sapiens

<400> SEQUENCE: 113

Met Asp Val Ser Leu Cys Pro Ala Lys Cys Ser Phe Trp Arg Ile Phe
1               5                   10                  15

Leu Leu Gly Ser Val Trp Leu Asp Tyr Val Gly Ser Val Leu Ala Cys
                20                  25                  30

Pro Ala Asn Cys Val Cys Ser Lys Thr Glu Ile Asn Cys Arg Arg Pro
            35                  40                  45
```

-continued

```
Asp Asp Gly Asn Leu Phe Pro Leu Leu Glu Gly Gln Asp Ser Gly Asn
    50                  55                  60
Ser Asn Gly Asn Ala Ser Ile Asn Ile Thr Asp Ile Ser Arg Asn Ile
 65                  70                  75                  80
Thr Ser Ile His Ile Glu Asn Trp Arg Ser Leu His Thr Leu Asn Ala
                 85                  90                  95
Val Asp Met Glu Leu Tyr Thr Gly Leu Gln Lys Leu Thr Ile Lys Asn
            100                 105                 110
Ser Gly Leu Arg Ser Ile Gln Pro Arg Ala Phe Ala Lys Asn Pro His
            115                 120                 125
Leu Arg Tyr Ile Asn Leu Ser Ser Asn Arg Leu Thr Thr Leu Ser Trp
        130                 135                 140
Gln Leu Phe Gln Thr Leu Ser Leu Arg Glu Leu Gln Leu Glu Gln Asn
145                 150                 155                 160
Phe Phe Asn Cys Ser Cys Asp Ile Arg Trp Met Gln Leu Trp Gln Glu
                165                 170                 175
Gln Gly Glu Ala Lys Leu Asn Ser Gln Asn Leu Tyr Cys Ile Asn Ala
            180                 185                 190
Asp Gly Ser Gln Leu Pro Leu Phe Arg Met Asn Ile Ser Gln Cys Asp
            195                 200                 205
Leu Pro Glu Ile Ser Val Ser His Val Asn Leu Thr Val Arg Glu Gly
        210                 215                 220
Asp Asn Ala Val Ile Thr Cys Asn Gly Ser Gly Ser Pro Leu Pro Asp
225                 230                 235                 240
Val Asp Trp Ile Val Thr Gly Leu Gln Ser Ile Asn Thr His Gln Thr
                245                 250                 255
Asn Leu Asn Trp Thr Asn Val His Ala Ile Asn Leu Thr Leu Val Asn
            260                 265                 270
Val Thr Ser Glu Asp Asn Gly Phe Thr Leu Thr Cys Ile Ala Glu Asn
            275                 280                 285
Val Val Gly Met Ser Asn Ala Ser Val Ala Leu Thr Val Tyr Tyr Pro
        290                 295                 300
Pro Arg Val Val Ser Leu Glu Glu Pro Glu Leu Arg Leu Glu His Cys
305                 310                 315                 320
Ile Glu Phe Val Val Arg Gly Asn Pro Pro Pro Thr Leu His Trp Leu
                325                 330                 335
His Asn Gly Gln Pro Leu Arg Glu Ser Lys Ile Ile His Val Glu Tyr
            340                 345                 350
Tyr Gln Glu Gly Glu Ile Ser Glu Gly Cys Leu Leu Phe Asn Lys Pro
            355                 360                 365
Thr His Tyr Asn Asn Gly Asn Tyr Thr Leu Ile Ala Lys Asn Pro Leu
        370                 375                 380
Gly Thr Ala Asn Gln Thr Ile Asn Gly His Phe Leu Lys Glu Pro Phe
385                 390                 395                 400
Pro Glu Ser Thr Asp Asn Phe Ile Leu Phe Asp Glu Val Ser Pro Thr
                405                 410                 415
Pro Pro Ile Thr Val Thr His Lys Pro Glu Glu Asp Thr Phe Gly Val
            420                 425                 430
Ser Ile Ala Val Gly Leu Ala Ala Phe Ala Cys Val Leu Leu Val Val
            435                 440                 445
Leu Phe Val Met Ile Asn Lys Tyr Gly Arg Arg Ser Lys Phe Gly Met
        450                 455                 460
Lys Gly Pro Val Ala Val Ile Ser Gly Glu Glu Asp Ser Ala Ser Pro
```

-continued

```
            465                 470                 475                 480
Leu His His Ile Asn His Gly Ile Thr Thr Pro Ser Ser Leu Asp Ala
                    485                 490                 495
Gly Pro Asp Thr Val Val Ile Gly Met Thr Arg Ile Pro Val Ile Glu
                500                 505                 510
Asn Pro Gln Tyr Phe Arg Gln Gly His Asn Cys His Lys Pro Asp Thr
            515                 520                 525
Trp Val Phe Ser Asn Ile Asp Asn His Gly Ile Leu Asn Leu Lys Asp
530                 535                 540
Asn Arg Asp His Leu Val Pro Ser Thr His Tyr Ile Tyr Glu Glu Pro
545                 550                 555                 560
Glu Val Gln Ser Gly Glu Val Ser Tyr Pro Arg Ser His Gly Phe Arg
                565                 570                 575
Glu Ile Met Leu Asn Pro Ile Ser Leu Pro Gly His Ser Lys Pro Leu
                580                 585                 590
Asn His Gly Ile Tyr Val Glu Asp Val Asn Val Tyr Phe Ser Lys Gly
            595                 600                 605
Arg His Gly Phe
    610

<210> SEQ ID NO 114
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
gguauaagug cacacugaau a                                              21

<210> SEQ ID NO 115
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
cacugaauag ucuaaucuac a                                              21

<210> SEQ ID NO 116
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 116
gagagucaaa caauguuaag g                                              21

<210> SEQ ID NO 117
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 117
```

```
gagaagaguu cuaugguuau c                                              21

<210> SEQ ID NO 118
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
gacaaagcag ugugcucuaa u                                              21

<210> SEQ ID NO 119
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
ggauguguuu guacuugcag a                                              21

<210> SEQ ID NO 120
<211> LENGTH: 838
<212> TYPE: PRT
<213> ORGANISM: Homo sapiens

<400> SEQUENCE: 120

Met Ser Ser Trp Ile Arg Trp His Gly Pro Ala Met Ala Arg Leu Trp
1               5                   10                  15

Gly Phe Cys Trp Leu Val Val Gly Phe Trp Arg Ala Ala Phe Ala Cys
            20                  25                  30

Pro Thr Ser Cys Lys Cys Ser Ala Ser Arg Ile Trp Cys Ser Asp Pro
        35                  40                  45

Ser Pro Gly Ile Val Ala Phe Pro Arg Leu Glu Pro Asn Ser Val Asp
    50                  55                  60

Pro Glu Asn Ile Thr Glu Ile Phe Ile Ala Asn Gln Lys Arg Leu Glu
65                  70                  75                  80

Ile Ile Asn Glu Asp Asp Val Glu Ala Tyr Val Gly Leu Arg Asn Leu
                85                  90                  95

Thr Ile Val Asp Ser Gly Leu Lys Phe Val Ala His Lys Ala Phe Leu
            100                 105                 110

Lys Asn Ser Asn Leu Gln His Ile Asn Phe Thr Arg Asn Lys Leu Thr
        115                 120                 125

Ser Leu Ser Arg Lys His Phe Arg His Leu Asp Leu Ser Glu Leu Ile
    130                 135                 140

Leu Val Gly Asn Pro Phe Thr Cys Ser Cys Asp Ile Met Trp Ile Lys
145                 150                 155                 160

Thr Leu Gln Glu Ala Lys Ser Ser Pro Asp Thr Gln Asp Leu Tyr Cys
                165                 170                 175

Leu Asn Glu Ser Ser Lys Asn Ile Pro Leu Ala Asn Leu Gln Ile Pro
            180                 185                 190

Asn Cys Gly Leu Pro Ser Ala Asn Leu Ala Ala Pro Asn Leu Thr Val
        195                 200                 205

Glu Glu Gly Lys Ser Ile Thr Leu Ser Cys Ser Val Ala Gly Asp Pro
    210                 215                 220

Val Pro Asn Met Tyr Trp Asp Val Gly Asn Leu Val Ser Lys His Met
```

-continued

```
                225                 230                 235                 240
Asn Glu Thr Ser His Thr Gln Gly Ser Leu Arg Ile Thr Asn Ile Ser
                    245                 250                 255

Ser Asp Asp Ser Gly Lys Gln Ile Ser Cys Val Ala Glu Asn Leu Val
                260                 265                 270

Gly Glu Asp Gln Asp Ser Val Asn Leu Thr Val His Phe Ala Pro Thr
                275                 280                 285

Ile Thr Phe Leu Glu Ser Pro Thr Ser Asp His His Trp Cys Ile Pro
290                 295                 300

Phe Thr Val Lys Gly Asn Pro Lys Pro Ala Leu Gln Trp Phe Tyr Asn
305                 310                 315                 320

Gly Ala Ile Leu Asn Glu Ser Lys Tyr Ile Cys Thr Lys Ile His Val
                325                 330                 335

Thr Asn His Thr Glu Tyr His Gly Cys Leu Gln Leu Asp Asn Pro Thr
                340                 345                 350

His Met Asn Asn Gly Asp Tyr Thr Leu Ile Ala Lys Asn Glu Tyr Gly
                355                 360                 365

Lys Asp Glu Lys Gln Ile Ser Ala His Phe Met Gly Trp Pro Gly Ile
                370                 375                 380

Asp Asp Gly Ala Asn Pro Asn Tyr Pro Asp Val Ile Tyr Glu Asp Tyr
385                 390                 395                 400

Gly Thr Ala Ala Asn Asp Ile Gly Asp Thr Thr Asn Arg Ser Asn Glu
                405                 410                 415

Ile Pro Ser Thr Asp Val Thr Asp Lys Thr Gly Arg Glu His Leu Ser
                420                 425                 430

Val Tyr Ala Val Val Val Ile Ala Ser Val Val Gly Phe Cys Leu Leu
                435                 440                 445

Val Met Leu Phe Leu Leu Lys Leu Ala Arg His Ser Lys Phe Gly Met
                450                 455                 460

Lys Asp Phe Ser Trp Phe Gly Phe Gly Lys Val Lys Ser Arg Gln Gly
465                 470                 475                 480

Val Gly Pro Ala Ser Val Ile Ser Asn Asp Asp Ser Ala Ser Pro
                485                 490                 495

Leu His His Ile Ser Asn Gly Ser Asn Thr Pro Ser Ser Glu Gly
                500                 505                 510

Gly Pro Asp Ala Val Ile Ile Gly Met Thr Lys Ile Pro Val Ile Glu
                515                 520                 525

Asn Pro Gln Tyr Phe Gly Ile Thr Asn Ser Gln Leu Lys Pro Asp Thr
                530                 535                 540

Phe Val Gln His Ile Lys Arg His Asn Ile Val Leu Lys Arg Glu Leu
545                 550                 555                 560

Gly Glu Gly Ala Phe Gly Lys Val Phe Leu Ala Glu Cys Tyr Asn Leu
                565                 570                 575

Cys Pro Glu Gln Asp Lys Ile Leu Val Ala Val Lys Thr Leu Lys Asp
                580                 585                 590

Ala Ser Asp Asn Ala Arg Lys Asp Phe His Arg Glu Ala Glu Leu Leu
                595                 600                 605

Thr Asn Leu Gln His Glu His Ile Val Lys Phe Tyr Gly Val Cys Val
                610                 615                 620

Glu Gly Asp Pro Leu Ile Met Val Phe Glu Tyr Met Lys His Gly Asp
625                 630                 635                 640

Leu Asn Lys Phe Leu Arg Ala His Gly Pro Asp Ala Val Leu Met Ala
                645                 650                 655
```

-continued

Glu Gly Asn Pro Pro Thr Glu Leu Thr Gln Ser Gln Met Leu His Ile
            660                 665                 670

Ala Gln Gln Ile Ala Ala Gly Met Val Tyr Leu Ala Ser Gln His Phe
        675                 680                 685

Val His Arg Asp Leu Ala Thr Arg Asn Cys Leu Val Gly Glu Asn Leu
    690                 695                 700

Leu Val Lys Ile Gly Asp Phe Gly Met Ser Arg Asp Val Tyr Ser Thr
705                 710                 715                 720

Asp Tyr Tyr Arg Val Gly Gly His Thr Met Leu Pro Ile Arg Trp Met
                725                 730                 735

Pro Pro Glu Ser Ile Met Tyr Arg Lys Phe Thr Thr Glu Ser Asp Val
            740                 745                 750

Trp Ser Leu Gly Val Val Leu Trp Glu Ile Phe Thr Tyr Gly Lys Gln
        755                 760                 765

Pro Trp Tyr Gln Leu Ser Asn Asn Glu Val Ile Glu Cys Ile Thr Gln
    770                 775                 780

Gly Arg Val Leu Gln Arg Pro Arg Thr Cys Pro Gln Glu Val Tyr Glu
785                 790                 795                 800

Leu Met Leu Gly Cys Trp Gln Arg Glu Pro His Met Arg Lys Asn Ile
                805                 810                 815

Lys Gly Ile His Thr Leu Leu Gln Asn Leu Ala Lys Ala Ser Pro Val
            820                 825                 830

Tyr Leu Asp Ile Leu Gly
            835

<210> SEQ ID NO 121
<211> LENGTH: 553
<212> TYPE: PRT
<213> ORGANISM: Homo sapiens

<400> SEQUENCE: 121

Met Ser Ser Trp Ile Arg Trp His Gly Pro Ala Met Ala Arg Leu Trp
1               5                   10                  15

Gly Phe Cys Trp Leu Val Val Gly Phe Trp Arg Ala Ala Phe Ala Cys
            20                  25                  30

Pro Thr Ser Cys Lys Cys Ser Ala Ser Arg Ile Trp Cys Ser Asp Pro
        35                  40                  45

Ser Pro Gly Ile Val Ala Phe Pro Arg Leu Glu Pro Asn Ser Val Asp
    50                  55                  60

Pro Glu Asn Ile Thr Glu Ile Phe Ile Ala Asn Gln Lys Arg Leu Glu
65                  70                  75                  80

Ile Ile Asn Glu Asp Asp Val Glu Ala Tyr Val Gly Leu Arg Asn Leu
                85                  90                  95

Thr Ile Val Asp Ser Gly Leu Lys Phe Val Ala His Lys Ala Phe Leu
            100                 105                 110

Lys Asn Ser Asn Leu Gln His Ile Asn Phe Thr Arg Asn Lys Leu Thr
        115                 120                 125

Ser Leu Ser Arg Lys His Phe Arg His Leu Asp Leu Ser Glu Leu Ile
    130                 135                 140

Leu Val Gly Asn Pro Phe Thr Cys Ser Cys Asp Ile Met Trp Ile Lys
145                 150                 155                 160

Thr Leu Gln Glu Ala Lys Ser Ser Pro Asp Thr Gln Asp Leu Tyr Cys
                165                 170                 175

Leu Asn Glu Ser Ser Lys Asn Ile Pro Leu Ala Asn Leu Gln Ile Pro

```
            180                 185                 190
Asn Cys Gly Leu Pro Ser Ala Asn Leu Ala Ala Pro Asn Leu Thr Val
        195                 200                 205

Glu Glu Gly Lys Ser Ile Thr Leu Ser Cys Ser Val Ala Gly Asp Pro
    210                 215                 220

Val Pro Asn Met Tyr Trp Asp Val Gly Asn Leu Val Ser Lys His Met
225                 230                 235                 240

Asn Glu Thr Ser His Thr Gln Gly Ser Leu Arg Ile Thr Asn Ile Ser
                245                 250                 255

Ser Asp Asp Ser Gly Lys Gln Ile Ser Cys Val Ala Glu Asn Leu Val
            260                 265                 270

Gly Glu Asp Gln Asp Ser Val Asn Leu Thr Val His Phe Ala Pro Thr
        275                 280                 285

Ile Thr Phe Leu Glu Ser Pro Thr Ser Asp His His Trp Cys Ile Pro
    290                 295                 300

Phe Thr Val Lys Gly Asn Pro Lys Pro Ala Leu Gln Trp Phe Tyr Asn
305                 310                 315                 320

Gly Ala Ile Leu Asn Glu Ser Lys Tyr Ile Cys Thr Lys Ile His Val
                325                 330                 335

Thr Asn His Thr Glu Tyr His Gly Cys Leu Gln Leu Asp Asn Pro Thr
            340                 345                 350

His Met Asn Asn Gly Asp Tyr Thr Leu Ile Ala Lys Asn Glu Tyr Gly
        355                 360                 365

Lys Asp Glu Lys Gln Ile Ser Ala His Phe Met Gly Trp Pro Gly Ile
    370                 375                 380

Asp Asp Gly Ala Asn Pro Asn Tyr Pro Asp Val Ile Tyr Glu Asp Tyr
385                 390                 395                 400

Gly Thr Ala Ala Asn Asp Ile Gly Asp Thr Thr Asn Arg Ser Asn Glu
                405                 410                 415

Ile Pro Ser Thr Asp Val Thr Asp Lys Thr Gly Arg Glu His Leu Ser
            420                 425                 430

Val Tyr Ala Val Val Val Ile Ala Ser Val Val Gly Phe Cys Leu Leu
        435                 440                 445

Val Met Leu Phe Leu Leu Lys Leu Ala Arg His Ser Lys Phe Gly Met
    450                 455                 460

Lys Asp Phe Ser Trp Phe Gly Phe Gly Lys Val Lys Ser Arg Gln Gly
465                 470                 475                 480

Val Gly Pro Ala Ser Val Ile Ser Asn Asp Asp Ser Ala Ser Pro
                485                 490                 495

Leu His His Ile Ser Asn Gly Ser Asn Thr Pro Ser Ser Glu Gly
            500                 505                 510

Gly Pro Asp Ala Val Ile Ile Gly Met Thr Lys Ile Pro Val Ile Glu
        515                 520                 525

Asn Pro Gln Tyr Phe Gly Ile Thr Asn Ser Gln Leu Lys Pro Asp Thr
    530                 535                 540

Trp Pro Arg Gly Ser Pro Lys Thr Ala
545                 550

<210> SEQ ID NO 122
<211> LENGTH: 537
<212> TYPE: PRT
<213> ORGANISM: Homo sapiens

<400> SEQUENCE: 122
```

```
Met Ser Ser Trp Ile Arg Trp His Gly Pro Ala Met Ala Arg Leu Trp
1               5                   10                  15

Gly Phe Cys Trp Leu Val Val Gly Phe Trp Arg Ala Ala Phe Ala Cys
            20                  25                  30

Pro Thr Ser Cys Lys Cys Ser Ala Ser Arg Ile Trp Cys Ser Asp Pro
            35                  40                  45

Ser Pro Gly Ile Val Ala Phe Pro Arg Leu Glu Pro Asn Ser Val Asp
    50                  55                  60

Pro Glu Asn Ile Thr Glu Ile Phe Ile Ala Asn Gln Lys Arg Leu Glu
65                  70                  75                  80

Ile Ile Asn Glu Asp Asp Val Glu Ala Tyr Val Gly Leu Arg Asn Leu
                85                  90                  95

Thr Ile Val Asp Ser Gly Leu Lys Phe Val Ala His Lys Ala Phe Leu
            100                 105                 110

Lys Asn Ser Asn Leu Gln His Ile Asn Phe Thr Arg Asn Lys Leu Thr
            115                 120                 125

Ser Leu Ser Arg Lys His Phe Arg His Leu Asp Leu Ser Glu Leu Ile
    130                 135                 140

Leu Val Gly Asn Pro Phe Thr Cys Ser Cys Asp Ile Met Trp Ile Lys
145                 150                 155                 160

Thr Leu Gln Glu Ala Lys Ser Ser Pro Asp Thr Gln Asp Leu Tyr Cys
            165                 170                 175

Leu Asn Glu Ser Ser Lys Asn Ile Pro Leu Ala Asn Leu Gln Ile Pro
            180                 185                 190

Asn Cys Gly Leu Pro Ser Ala Asn Leu Ala Ala Pro Asn Leu Thr Val
    195                 200                 205

Glu Glu Gly Lys Ser Ile Thr Leu Ser Cys Ser Val Ala Gly Asp Pro
210                 215                 220

Val Pro Asn Met Tyr Trp Asp Val Gly Asn Leu Val Ser Lys His Met
225                 230                 235                 240

Asn Glu Thr Ser His Thr Gln Gly Ser Leu Arg Ile Thr Asn Ile Ser
            245                 250                 255

Ser Asp Asp Ser Gly Lys Gln Ile Ser Cys Val Ala Glu Asn Leu Val
            260                 265                 270

Gly Glu Asp Gln Asp Ser Val Asn Leu Thr Val His Phe Ala Pro Thr
    275                 280                 285

Ile Thr Phe Leu Glu Ser Pro Thr Ser Asp His His Trp Cys Ile Pro
    290                 295                 300

Phe Thr Val Lys Gly Asn Pro Lys Pro Ala Leu Gln Trp Phe Tyr Asn
305                 310                 315                 320

Gly Ala Ile Leu Asn Glu Ser Lys Tyr Ile Cys Thr Lys Ile His Val
            325                 330                 335

Thr Asn His Thr Glu Tyr His Gly Cys Leu Gln Leu Asp Asn Pro Thr
            340                 345                 350

His Met Asn Asn Gly Asp Tyr Thr Leu Ile Ala Lys Asn Glu Tyr Gly
    355                 360                 365

Lys Asp Glu Lys Gln Ile Ser Ala His Phe Met Gly Trp Pro Gly Ile
    370                 375                 380

Asp Asp Gly Ala Asn Pro Asn Tyr Pro Asp Val Ile Tyr Glu Asp Tyr
385                 390                 395                 400

Gly Thr Ala Ala Asn Asp Ile Gly Asp Thr Thr Asn Arg Ser Asn Glu
            405                 410                 415

Ile Pro Ser Thr Asp Val Thr Asp Lys Thr Gly Arg Glu His Leu Ser
```

```
            420                 425                 430
Val Tyr Ala Val Val Ile Ala Ser Val Val Gly Phe Cys Leu Leu
            435                 440                 445

Val Met Leu Phe Leu Leu Lys Leu Ala Arg His Ser Lys Phe Gly Met
        450                 455                 460

Lys Gly Pro Ala Ser Val Ile Ser Asn Asp Asp Ser Ala Ser Pro
465                 470                 475                 480

Leu His His Ile Ser Asn Gly Ser Asn Thr Pro Ser Ser Glu Gly
                    485                 490                 495

Gly Pro Asp Ala Val Ile Ile Gly Met Thr Lys Ile Pro Val Ile Glu
                500                 505                 510

Asn Pro Gln Tyr Phe Gly Ile Thr Asn Ser Gln Leu Lys Pro Asp Thr
            515                 520                 525

Trp Pro Arg Gly Ser Pro Lys Thr Ala
        530                 535

<210> SEQ ID NO 123
<211> LENGTH: 464
<212> TYPE: PRT
<213> ORGANISM: Homo sapiens

<400> SEQUENCE: 123

Met Ser Ser Trp Ile Arg Trp His Gly Pro Ala Met Ala Arg Leu Trp
1               5                   10                  15

Gly Phe Cys Trp Leu Val Val Gly Phe Trp Arg Ala Ala Phe Ala Cys
                20                  25                  30

Pro Thr Ser Cys Lys Cys Ser Ala Ser Arg Ile Trp Cys Ser Asp Pro
            35                  40                  45

Ser Pro Gly Ile Val Ala Phe Pro Arg Leu Glu Pro Asn Ser Val Asp
        50                  55                  60

Pro Glu Asn Ile Thr Glu Ile Phe Ile Ala Asn Gln Lys Arg Leu Glu
65                  70                  75                  80

Ile Ile Asn Glu Asp Asp Val Glu Ala Tyr Val Gly Leu Arg Asn Leu
                85                  90                  95

Thr Ile Val Asp Ser Gly Leu Lys Phe Val Ala His Lys Ala Phe Leu
            100                 105                 110

Lys Asn Ser Asn Leu Gln His Ile Asn Phe Thr Arg Asn Lys Leu Thr
        115                 120                 125

Ser Leu Ser Arg Lys His Phe Arg His Leu Asp Leu Ser Glu Leu Ile
130                 135                 140

Leu Val Gly Asn Pro Phe Thr Cys Ser Cys Asp Ile Met Trp Ile Lys
145                 150                 155                 160

Thr Leu Gln Glu Ala Lys Ser Ser Pro Asp Thr Gln Asp Leu Tyr Cys
                165                 170                 175

Leu Asn Glu Ser Ser Lys Asn Ile Pro Leu Ala Asn Leu Gln Ile Pro
            180                 185                 190

Asn Cys Gly Leu Pro Ser Ala Asn Leu Ala Ala Pro Asn Leu Thr Val
        195                 200                 205

Glu Glu Gly Lys Ser Ile Thr Leu Ser Cys Ser Val Ala Gly Asp Pro
210                 215                 220

Val Pro Asn Met Tyr Trp Asp Val Gly Asn Leu Val Ser Lys His Met
225                 230                 235                 240

Asn Glu Thr Ser His Thr Gln Gly Ser Leu Arg Ile Thr Asn Ile Ser
                245                 250                 255
```

```
Ser Asp Asp Ser Gly Lys Gln Ile Ser Cys Val Ala Glu Asn Leu Val
            260                 265                 270

Gly Glu Asp Gln Asp Ser Val Asn Leu Thr Val His Tyr His His Trp
        275                 280                 285

Cys Ile Pro Phe Thr Val Lys Gly Asn Pro Lys Pro Ala Leu Gln Trp
        290                 295             300

Phe Tyr Asn Gly Ala Ile Leu Asn Glu Ser Lys Tyr Ile Cys Thr Lys
305                 310                 315                 320

Ile His Val Thr Asn His Thr Glu Tyr His Gly Cys Leu Gln Leu Asp
                325                 330                 335

Asn Pro Thr His Met Asn Asn Gly Asp Tyr Thr Leu Ile Ala Lys Asn
            340                 345                 350

Glu Tyr Gly Lys Asp Glu Lys Gln Ile Ser Ala His Phe Met Gly Trp
        355                 360                 365

Pro Gly Ile Asp Asp Gly Ala Asn Pro Asn Tyr Pro Asp Val Ile Tyr
        370                 375                 380

Glu Asp Tyr Gly Thr Ala Ala Asn Asp Ile Gly Asp Thr Thr Asn Arg
385                 390                 395                 400

Ser Asn Glu Ile Pro Ser Thr Asp Val Thr Asp Lys Thr Gly Arg Glu
            405                 410                 415

His Leu Ser Val Tyr Ala Val Val Val Ile Ala Ser Val Val Gly Phe
                420                 425                 430

Cys Leu Leu Val Met Leu Phe Leu Leu Lys Leu Ala Arg His Ser Lys
            435                 440                 445

Phe Gly Met Lys Gly Phe Val Leu Phe His Lys Ile Pro Leu Asp Gly
        450                 455                 460

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
gtccagagtg gggatgtgtc                                                  20

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
ccatggttaa gaggcttgga                                                  20
```